(12) United States Patent
Martinez-Hackert et al.

(10) Patent No.: US 10,323,074 B2
(45) Date of Patent: Jun. 18, 2019

(54) CRYPTIC POLYPEPTIDES AND USES THEREOF

(71) Applicant: Board of Trustees of Michigan State University, East Lansing, MI (US)

(72) Inventors: Erik Martinez-Hackert, Okemos, MI (US); Senem Aykul, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 15/839,372

(22) Filed: Dec. 12, 2017

(65) Prior Publication Data

US 2018/0170987 A1 Jun. 21, 2018

Related U.S. Application Data

(63) Continuation of application No. 15/547,258, filed as application No. PCT/US2016/015587 on Jan. 29, 2016.

(60) Provisional application No. 62/109,376, filed on Jan. 29, 2015.

(51) Int. Cl.

| | | |
|---|---|---|
| C07K 14/47 | (2006.01) |
| C07K 14/485 | (2006.01) |
| C07K 14/71 | (2006.01) |
| C07K 14/82 | (2006.01) |
| A61P 1/02 | (2006.01) |
| A61P 21/00 | (2006.01) |
| A61P 35/00 | (2006.01) |
| A61K 38/18 | (2006.01) |
| A61K 45/06 | (2006.01) |
| C12N 15/62 | (2006.01) |

(52) U.S. Cl.
CPC ........ *C07K 14/485* (2013.01); *A61K 38/1808* (2013.01); *A61K 45/06* (2013.01); *A61P 1/02* (2018.01); *A61P 21/00* (2018.01); *A61P 35/00* (2018.01); *C07K 14/47* (2013.01); *C07K 14/71* (2013.01); *C07K 14/82* (2013.01); *C07K 2319/02* (2013.01); *C07K 2319/30* (2013.01)

(58) Field of Classification Search
None
See application file for complete search history.

(56) References Cited

U.S. PATENT DOCUMENTS

| | | |
|---|---|---|
| 7,638,330 B2 | 12/2009 | Minchiotti et al. |
| 9,546,210 B2 | 1/2017 | Vale et al. |
| 2008/0159989 A1* | 7/2008 | Minchiotti ............ A61K 35/34 424/93.7 |

FOREIGN PATENT DOCUMENTS

| | | |
|---|---|---|
| EP | 2135952 A2 | 12/2009 |
| WO | WO-96/39420 A1 | 12/1996 |
| WO | WO 03/077939 A1 * | 9/2003 |
| WO | WO-2008028888 A2 | 3/2008 |

OTHER PUBLICATIONS

Tokuriki et al., 2009, Curr. Opin. Struc. Biol. 19:596-604.*
Bhattacharya et al., 2017, PLoS ONE 12(3): e0171355, https://doi.org/10.1371/journal.pone.0171355.*
Alaoui-Ismaili, 2009, Cytokine Growth Factor Rev. 20(5-6):501-7.*
Guo et al., 2004, PNAS USA 101(25):9205-10.*
Gray et al., "Cripto forms a complex with activin and type II activin receptors and can block activin signaling," PNAS, 100(9): 5193-5198 (2003).
International Search Report and Written Opinion for International Application No. PCT/US2016/015587 dated May 12, 2016.
Yeo et al., "Nodal signals to Smads through Cripto-dependent and Cripto-independent mechanisms," Mol Cell, 7(5): 949-957 (2001).

* cited by examiner

*Primary Examiner* — Elizabeth C. Kemmerer
(74) *Attorney, Agent, or Firm* — Foley Hoag LLP; DeAnn F. Smith; Allison Gilder

(57) ABSTRACT

The disclosure features, among other things, polypeptides comprising a Cryptic polypeptide, a functional fragment thereof, or variants of any of the foregoing. Also featured are nucleic acids encoding the polypeptides, methods for producing of the polypeptides, and a variety of diagnostic and therapeutic applications in which the polypeptides are useful. For example, the polypeptides can be used to treat a subject having a condition associated with bone loss.

22 Claims, 20 Drawing Sheets

Specification includes a Sequence Listing.

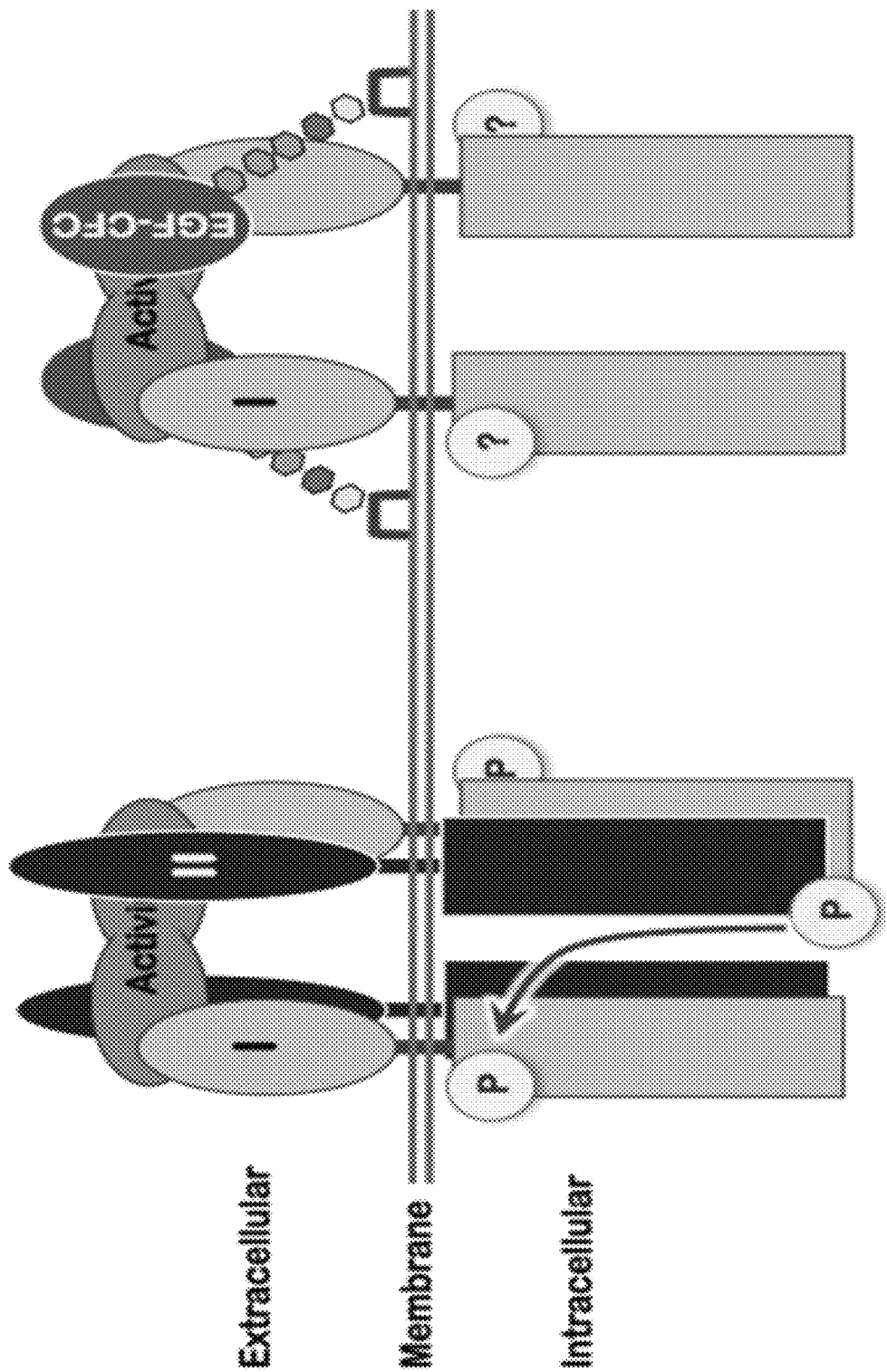

ΔCryptic

SEQUENCE LISTING

<160> NUMBER OF SEQ ID NOS: 26

<210> SEQ ID NO 1
<211> LENGTH: 223
<212> TYPE: PRT
<213> ORGANISM: Homo sapiens

<400> SEQUENCE: 1

Met Thr Trp Arg His His Val Arg Leu Leu Phe Thr Val Ser Leu Ala
1               5                   10                  15

Leu Gln Ile Ile Asn Leu Gly Asn Ser Tyr Gln Arg Glu Lys His Asn
                20                  25                  30

Gly Gly Arg Glu Glu Val Thr Lys Val Ala Thr Gln Lys His Arg Gln
            35                  40                  45

Ser Pro Leu Asn Trp Thr Ser Ser His Phe Gly Glu Val Thr Gly Ser
    50                  55                  60

Ala Glu Gly Trp Gly Pro Glu Pro Leu Pro Tyr Ser Arg Ala Phe
65                  70                  75                  80

Gly Glu Gly Ala Ser Ala Arg Pro Arg Cys Cys Arg Asn Gly Gly Thr
                85                  90                  95

Cys Val Leu Gly Ser Phe Cys Val Cys Pro Ala His Phe Thr Gly Arg
                100                 105                 110

Tyr Cys Glu His Asp Gln Arg Ser Glu Cys Gly Ala Leu Glu His
                115                 120                 125

Gly Ala Trp Thr Leu Arg Ala Cys His Leu Cys Arg Cys Ile Phe Gly
        130                 135                 140

Ala Leu His Cys Leu Pro Leu Gln Thr Pro Asp Arg Cys Asp Pro Lys
145                 150                 155                 160

Asp Phe Leu Ala Ser His Ala His Gly Pro Ser Ala Gly Ala Pro
                165                 170                 175

Ser Leu Leu Leu Leu Leu Pro Cys Ala Leu Leu His Arg Leu Leu Arg
                180                 185                 190

Pro Asp Ala Pro Ala His Pro Arg Ser Leu Val Pro Ser Val Leu Gln
                195                 200                 205

Arg Glu Arg Arg Pro Cys Gly Arg Pro Gly Leu Gly His Arg Leu
    210                 215                 220

<210> SEQ ID NO 2
<211> LENGTH: 198
<212> TYPE: PRT
<213> ORGANISM: Homo sapiens

<400> SEQUENCE: 2

Tyr Gln Arg Glu Lys His Asn Gly Gly Arg Glu Glu Val Thr Lys Val
1               5                   10                  15

Ala Thr Gln Lys His Arg Gln Ser Pro Leu Asn Trp Thr Ser Ser His
                20                  25                  30

Phe Gly Glu Val Thr Gly Ser Ala Glu Gly Trp Gly Pro Glu Glu Pro
            35                  40                  45

Leu Pro Tyr Ser Arg Ala Phe Gly Glu Gly Ala Ser Ala Arg Pro Arg
    50                  55                  60

Cys Cys Arg Asn Gly Gly Thr Cys Val Leu Gly Ser Phe Cys Val Cys
65                  70                  75                  80

Pro Ala His Phe Thr Gly Arg Tyr Cys Glu His Asp Gln Arg Arg Ser
                85                  90                  95

Glu Cys Gly Ala Leu Glu His Gly Ala Trp Thr Leu Arg Ala Cys His

```
            100                 105                 110
Leu Cys Arg Cys Ile Phe Gly Ala Leu His Cys Leu Pro Leu Gln Thr
        115                 120                 125

Pro Asp Arg Cys Asp Pro Lys Asp Phe Leu Ala Ser His Ala His Gly
    130                 135                 140

Pro Ser Ala Gly Gly Ala Pro Ser Leu Leu Leu Leu Pro Cys Ala
145                 150                 155                 160

Leu Leu His Arg Leu Leu Arg Pro Asp Ala Pro Ala His Pro Arg Ser
                165                 170                 175

Leu Val Pro Ser Val Leu Gln Arg Glu Arg Pro Cys Gly Arg Pro
            180                 185                 190

Gly Leu Gly His Arg Leu
        195

<210> SEQ ID NO 3
<211> LENGTH: 132
<212> TYPE: PRT
<213> ORGANISM: Homo sapiens

<400> SEQUENCE: 3

Tyr Gln Arg Glu Lys His Asn Gly Gly Arg Glu Glu Val Thr Lys Val
1               5                   10                  15

Ala Thr Gln Lys His Arg Gln Ser Pro Leu Asn Trp Thr Ser Ser His
            20                  25                  30

Phe Gly Glu Val Thr Gly Ser Ala Glu Gly Trp Gly Pro Glu Glu Pro
        35                  40                  45

Leu Pro Tyr Ser Arg Ala Phe Gly Glu Gly Ala Ser Ala Arg Pro Arg
    50                  55                  60

Cys Cys Arg Asn Gly Gly Thr Cys Val Leu Gly Ser Phe Cys Val Cys
65                  70                  75                  80

Pro Ala His Phe Thr Gly Arg Tyr Cys Glu His Asp Gln Arg Arg Ser
                85                  90                  95

Glu Cys Gly Ala Leu Glu His Gly Ala Trp Thr Leu Arg Ala Cys His
            100                 105                 110

Leu Cys Arg Cys Ile Phe Gly Ala Leu His Cys Leu Pro Leu Gln Thr
        115                 120                 125

Pro Asp Arg Cys
    130

<210> SEQ ID NO 4
<211> LENGTH: 62
<212> TYPE: PRT
<213> ORGANISM: Homo sapiens

<400> SEQUENCE: 4

Tyr Gln Arg Glu Lys His Asn Gly Gly Arg Glu Glu Val Thr Lys Val
1               5                   10                  15

Ala Thr Gln Lys His Arg Gln Ser Pro Leu Asn Trp Thr Ser Ser His
            20                  25                  30

Phe Gly Glu Val Thr Gly Ser Ala Glu Gly Trp Gly Pro Glu Glu Pro
        35                  40                  45

Leu Pro Tyr Ser Arg Ala Phe Gly Glu Gly Ala Ser Ala Arg
    50                  55                  60

<210> SEQ ID NO 5
<211> LENGTH: 32
<212> TYPE: PRT
```

```
<213> ORGANISM: Homo sapiens

<400> SEQUENCE: 5

Pro Arg Cys Cys Arg Asn Gly Gly Thr Cys Val Leu Gly Ser Phe Cys
1               5                   10                  15

Val Cys Pro Ala His Phe Thr Gly Arg Tyr Cys Glu His Asp Gln Arg
            20                  25                  30

<210> SEQ ID NO 6
<211> LENGTH: 48
<212> TYPE: PRT
<213> ORGANISM: Homo sapiens

<400> SEQUENCE: 6

Arg Ser Glu Cys Gly Ala Leu Glu His Gly Ala Trp Thr Leu Arg Ala
1               5                   10                  15

Cys His Leu Cys Arg Cys Ile Phe Gly Ala Leu His Cys Leu Pro Leu
            20                  25                  30

Gln Thr Pro Asp Arg Cys Asp Pro Lys Asp Phe Leu Ala Ser His Ala
        35                  40                  45

<210> SEQ ID NO 7
<211> LENGTH: 30
<212> TYPE: PRT
<213> ORGANISM: Homo sapiens

<400> SEQUENCE: 7

Cys Cys Arg Asn Gly Gly Thr Cys Val Leu Gly Ser Phe Cys Val Cys
1               5                   10                  15

Pro Ala His Phe Thr Gly Arg Tyr Cys Glu His Asp Gln Arg
            20                  25                  30

<210> SEQ ID NO 8
<211> LENGTH: 80
<212> TYPE: PRT
<213> ORGANISM: Homo sapiens

<400> SEQUENCE: 8

Pro Arg Cys Cys Arg Asn Gly Gly Thr Cys Val Leu Gly Ser Phe Cys
1               5                   10                  15

Val Cys Pro Ala His Phe Thr Gly Arg Tyr Cys Glu His Asp Gln Arg
            20                  25                  30

Arg Ser Glu Cys Gly Ala Leu Glu His Gly Ala Trp Thr Leu Arg Ala
            35                  40                  45

Cys His Leu Cys Arg Cys Ile Phe Gly Ala Leu His Cys Leu Pro Leu
        50                  55                  60

Gln Thr Pro Asp Arg Cys Asp Pro Lys Asp Phe Leu Ala Ser His Ala
65                  70                  75                  80

<210> SEQ ID NO 9
<211> LENGTH: 11
<212> TYPE: PRT
<213> ORGANISM: Homo sapiens

<400> SEQUENCE: 9

Asn Gly Gly Thr Cys Val Leu Gly Ser Phe Cys
1               5                   10

<210> SEQ ID NO 10
<211> LENGTH: 412
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 10

Met Thr Trp Arg His His Val Arg Leu Leu Phe Thr Val Ser Leu Ala
1               5                   10                  15

Leu Gln Ile Ile Asn Leu Gly Asn Ser Tyr Gln Arg Glu Lys His Asn
            20                  25                  30

Gly Gly Arg Glu Glu Val Thr Lys Val Ala Thr Gln Lys His Arg Gln
        35                  40                  45

Ser Pro Leu Asn Trp Thr Ser Ser His Phe Gly Glu Val Thr Gly Ser
    50                  55                  60

Ala Glu Gly Trp Gly Pro Glu Pro Leu Pro Tyr Ser Arg Ala Phe
65                  70                  75                  80

Gly Glu Gly Ala Ser Ala Arg Pro Arg Cys Cys Arg Asn Gly Gly Thr
                85                  90                  95

Cys Val Leu Gly Ser Phe Cys Val Cys Pro Ala His Phe Thr Gly Arg
                100                 105                 110

Tyr Cys Glu His Asp Gln Arg Ser Glu Cys Gly Ala Leu Glu His
                115                 120                 125

Gly Ala Trp Thr Leu Arg Ala Cys His Leu Cys Arg Cys Ile Phe Gly
        130                 135                 140

Ala Leu His Cys Leu Pro Leu Gln Thr Pro Asp Arg Cys Asp Pro Lys
145                 150                 155                 160

Glu Asn Leu Tyr Phe Gln Gly Gly Ser Gly Gly Ser Gly Gly Asp
                165                 170                 175

Tyr Lys Asp Asp Asp Asp Lys Ser Ser Asp Lys Thr His Thr Cys Pro
                180                 185                 190

Pro Cys Pro Ala Pro Glu Leu Leu Gly Gly Pro Ser Val Phe Leu Phe
            195                 200                 205

Pro Pro Lys Pro Lys Asp Thr Leu Met Ile Ser Arg Thr Pro Glu Val
        210                 215                 220

Thr Cys Val Val Val Asp Val Ser His Glu Asp Pro Glu Val Lys Phe
225                 230                 235                 240

Asn Trp Tyr Val Asp Gly Val Glu Val His Asn Ala Lys Thr Lys Pro
                245                 250                 255

Arg Glu Glu Gln Tyr Asn Ser Thr Tyr Arg Val Val Ser Val Leu Thr
                260                 265                 270

Val Leu His Gln Asp Trp Leu Asn Gly Lys Glu Tyr Lys Cys Lys Val
            275                 280                 285

Ser Asn Lys Ala Leu Pro Ala Pro Ile Glu Lys Thr Ile Ser Lys Ala
        290                 295                 300

Lys Gly Gln Pro Arg Glu Pro Gln Val Tyr Thr Leu Pro Pro Ser Arg
305                 310                 315                 320

Asp Glu Leu Thr Lys Asn Gln Val Ser Leu Thr Cys Leu Val Lys Gly
                325                 330                 335

Phe Tyr Pro Ser Asp Ile Ala Val Glu Trp Glu Ser Asn Gly Gln Pro
                340                 345                 350

Glu Asn Asn Tyr Lys Thr Thr Pro Pro Val Leu Asp Ser Asp Gly Ser
            355                 360                 365

Phe Phe Leu Tyr Ser Lys Leu Thr Val Asp Lys Ser Arg Trp Gln Gln
        370                 375                 380

```
Gly Asn Val Phe Ser Cys Ser Val Met His Glu Ala Leu His Asn His
385                 390                 395                 400

Tyr Thr Gln Lys Ser Leu Ser Leu Ser Pro Gly Lys
            405                 410
```

<210> SEQ ID NO 11
<211> LENGTH: 223
<212> TYPE: PRT
<213> ORGANISM: Pan troglodytes

<400> SEQUENCE: 11

```
Met Thr Trp Arg His His Val Arg Leu Leu Phe Thr Val Ser Leu Ala
1               5                   10                  15

Leu Gln Ile Ile Asn Leu Gly Asn Ser Tyr Gln Arg Glu Lys His Asn
            20                  25                  30

Gly Gly Arg Glu Glu Val Ile Lys Val Ala Thr Gln Lys His Gln Gln
        35                  40                  45

Ser Pro Leu Asn Trp Thr Ser Ser His Phe Gly Glu Val Thr Gly Ser
    50                  55                  60

Ala Glu Gly Trp Gly Pro Glu Pro Leu Thr Tyr Ser Trp Ala Phe
65                  70                  75                  80

Gly Glu Gly Ala Ser Ala Arg Pro Arg Cys Cys Arg Asn Gly Gly Thr
                85                  90                  95

Cys Val Leu Gly Ser Phe Cys Val Cys Pro Ala His Phe Thr Gly Arg
            100                 105                 110

Tyr Cys Glu His Asp Gln Arg Ser Glu Cys Gly Ala Leu Glu His
        115                 120                 125

Gly Ala Trp Thr Leu Arg Ala Cys His Leu Cys Arg Cys Ile Phe Gly
    130                 135                 140

Ala Leu His Cys Leu Pro Leu Gln Thr Pro Asp Arg Cys Asp Pro Lys
145                 150                 155                 160

Asp Phe Leu Ala Ser His Ala His Gly Pro Ser Ala Gly Gly Ala Pro
                165                 170                 175

Ser Leu Leu Leu Leu Leu Pro Cys Ala Leu Leu His Arg Leu Leu Arg
            180                 185                 190

Pro Asp Ala Pro Ala His Pro Arg Ser Leu Val Pro Ser Val Leu Gln
        195                 200                 205

Arg Glu Arg Arg Pro Cys Gly Arg Pro Gly Leu Gly His Arg Leu
    210                 215                 220
```

<210> SEQ ID NO 12
<211> LENGTH: 201
<212> TYPE: PRT
<213> ORGANISM: Mus musculus

<400> SEQUENCE: 12

```
Met Arg Ala Asn Ser Pro Thr Gln Gly Ile Ser Leu Lys Met His Gln
1               5                   10                  15

Ala Arg Pro Leu Phe Leu Val Thr Val Ala Leu Gln Leu Ile Gly Leu
            20                  25                  30

Gly Tyr Ser Tyr Gln Ser Glu Gly Asp Gly Ala Arg Glu Val Ser Asn
        35                  40                  45

Ile Leu Ser Pro Val Ile Pro Gly Thr Thr Leu Asp Arg Thr Leu Ser
    50                  55                  60

Asn Ser Ser Arg Lys Asn Asp Ile Pro Glu Gly Ala Arg Leu Trp Asp
65                  70                  75                  80
```

-continued

```
Ser Leu Pro Asp Ser Ser Thr Leu Gly Glu Ser Ala Val Pro Val Ser
             85                  90                  95

Arg Cys Cys His Asn Gly Gly Thr Cys Val Leu Gly Ser Phe Cys Val
            100                 105                 110

Cys Pro Ala Tyr Phe Thr Gly Arg Tyr Cys Glu His Asp Gln Arg Arg
            115                 120                 125

Arg Asp Cys Gly Ala Leu Gly His Gly Ala Trp Thr Leu His Ser Cys
        130                 135                 140

Arg Leu Cys Arg Cys Ile Phe Ser Ala Leu Tyr Cys Leu Pro His Gln
145                 150                 155                 160

Thr Phe Ser His Cys Asp Leu Lys Ser Phe Leu Ser Ser Gly Ala Arg
                165                 170                 175

Gly Ser Glu Cys Ser Ile Pro Ser Leu Leu Leu Val Leu Cys Leu
            180                 185                 190

Leu Leu Gln Gly Val Ala Gly Lys Gly
            195                 200
```

<210> SEQ ID NO 13
<211> LENGTH: 426
<212> TYPE: PRT
<213> ORGANISM: Homo sapiens

<400> SEQUENCE: 13

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255
```

```
Leu Gly Lys Lys Lys Lys Glu Glu Gly Glu Gly Lys Lys Lys
            260                 265                 270

Gly Gly Gly Glu Gly Gly Ala Gly Ala Asp Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
        355                 360                 365

His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
                420                 425

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Tyr Lys Asp Asp Asp Asp Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

His His His His His His
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Pro Tyr Asp Val Pro Asp Tyr Ala
1               5

<210> SEQ ID NO 17
<211> LENGTH: 225
```

```
<212> TYPE: PRT
<213> ORGANISM: Homo sapiens
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 17

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Asn Leu Tyr Phe Gln Gly Gly Ser Gly Gly Ser Gly Gly Asp
1               5                   10                  15

Tyr Lys Asp Asp Asp Asp
            20
```

<210> SEQ ID NO 19
<211> LENGTH: 160
<212> TYPE: PRT
<213> ORGANISM: Homo sapiens

<400> SEQUENCE: 19

```
Met Thr Trp Arg His His Val Arg Leu Leu Phe Thr Val Ser Leu Ala
1               5                   10                  15

Leu Gln Ile Ile Asn Leu Gly Asn Ser Tyr Gln Arg Glu Lys His Asn
            20                  25                  30

Gly Gly Arg Glu Glu Val Thr Lys Val Ala Thr Gln Lys His Arg Gln
        35                  40                  45

Ser Pro Leu Asn Trp Thr Ser Ser His Phe Gly Glu Val Thr Gly Ser
    50                  55                  60

Ala Glu Gly Trp Gly Pro Glu Pro Leu Pro Tyr Ser Arg Ala Phe
65                  70                  75                  80

Gly Glu Gly Ala Ser Ala Arg Pro Arg Cys Cys Arg Asn Gly Gly Thr
                85                  90                  95

Cys Val Leu Gly Ser Phe Cys Val Cys Pro Ala His Phe Thr Gly Arg
            100                 105                 110

Tyr Cys Glu His Asp Gln Arg Ser Glu Cys Gly Ala Leu Glu His
        115                 120                 125

Gly Ala Trp Thr Leu Arg Ala Cys His Leu Cys Arg Cys Ile Phe Gly
    130                 135                 140

Ala Leu His Cys Leu Pro Leu Gln Thr Pro Asp Arg Cys Asp Pro Lys
145                 150                 155                 160
```

<210> SEQ ID NO 20
<211> LENGTH: 135
<212> TYPE: PRT
<213> ORGANISM: Homo sapiens

<400> SEQUENCE: 20

```
Tyr Gln Arg Glu Lys His Asn Gly Gly Arg Glu Glu Val Thr Lys Val
1               5                   10                  15

Ala Thr Gln Lys His Arg Gln Ser Pro Leu Asn Trp Thr Ser Ser His
            20                  25                  30

Phe Gly Glu Val Thr Gly Ser Ala Glu Gly Trp Gly Pro Glu Glu Pro
        35                  40                  45

Leu Pro Tyr Ser Arg Ala Phe Gly Glu Gly Ala Ser Ala Arg Pro Arg
    50                  55                  60

Cys Cys Arg Asn Gly Gly Thr Cys Val Leu Gly Ser Phe Cys Val Cys
65                  70                  75                  80

Pro Ala His Phe Thr Gly Arg Tyr Cys Glu His Asp Gln Arg Ser
                85                  90                  95

Glu Cys Gly Ala Leu Glu His Gly Ala Trp Thr Leu Arg Ala Cys His
            100                 105                 110

Leu Cys Arg Cys Ile Phe Gly Ala Leu His Cys Leu Pro Leu Gln Thr
        115                 120                 125

Pro Asp Arg Cys Asp Pro Lys
    130                 135
```

<210> SEQ ID NO 21
<211> LENGTH: 230
<212> TYPE: PRT
<213> ORGANISM: Homo sapiens

<400> SEQUENCE: 21

Lys Ser Ser Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 22
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Tyr Gln Arg Glu Lys His Asn Gly Gly Arg Glu Glu Val Thr Lys Val
1               5                   10                  15

Ala Thr Gln Lys His Arg Gln Ser Pro Leu Asn Trp Thr Ser Ser His
            20                  25                  30

Phe Gly Glu Val Thr Gly Ser Ala Glu Gly Trp Gly Pro Glu Glu Pro
        35                  40                  45

Leu Pro Tyr Ser Arg Ala Phe Gly Glu Gly Ala Ser Ala Arg Pro Arg
    50                  55                  60

Cys Cys Arg Asn Gly Gly Thr Cys Val Leu Gly Ser Phe Cys Val Cys
65                  70                  75                  80

Pro Ala His Phe Thr Gly Arg Tyr Cys Glu His Asp Gln Arg Arg Ser
                85                  90                  95

Glu Cys Gly Ala Leu Glu His Gly Ala Trp Thr Leu Arg Ala Cys His
            100                 105                 110

```
Leu Cys Arg Cys Ile Phe Gly Ala Leu His Cys Leu Pro Leu Gln Thr
            115                 120                 125

Pro Asp Arg Cys Asp Pro Lys Glu Asn Leu Tyr Phe Gln Gly Gly Gly
        130                 135                 140

Ser Gly Gly Ser Gly Gly Asp Tyr Lys Asp Asp Asp Asp Lys Ser Ser
145                 150                 155                 160

Asp Lys Thr His Thr Cys Pro Pro Cys Pro Ala Pro Glu Leu Leu Gly
            165                 170                 175

Gly Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
        195                 200                 205

Glu Asp Pro Glu Val Lys Phe Asn Trp Tyr Val Asp Gly Val Glu Val
210                 215                 220

His Asn Ala Lys Thr Lys Pro Arg Glu Glu Gln Tyr Asn Ser Thr Tyr
225                 230                 235                 240

Arg Val Val Ser Val Leu Thr Val Leu His Gln Asp Trp Leu Asn Gly
            245                 250                 255

Lys Glu Tyr Lys Cys Lys Val Ser Asn Lys Ala Leu Pro Ala Pro Ile
            260                 265                 270

Glu Lys Thr Ile Ser Lys Ala Lys Gly Gln Pro Arg Glu Pro Gln Val
        275                 280                 285

Tyr Thr Leu Pro Pro Ser Arg Asp Glu Leu Thr Lys Asn Gln Val Ser
        290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
            325                 330                 335

Val Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
        355                 360                 365

His Glu Ala Leu His Asn His Tyr Thr Gln Lys Ser Leu Ser Leu Ser
370                 375                 380

Pro Gly Lys
385

<210> SEQ ID NO 23
<211> LENGTH: 148
<212> TYPE: PRT
<213> ORGANISM: Homo sapiens

<400> SEQUENCE: 23

Tyr Gln Arg Glu Lys His Asn Gly Gly Arg Glu Glu Val Thr Lys Val
1               5                   10                  15

Ala Thr Gln Lys His Arg Gln Ser Pro Leu Asn Trp Thr Ser Ser His
            20                  25                  30

Phe Gly Glu Val Thr Gly Ser Ala Glu Gly Trp Gly Pro Glu Glu Pro
        35                  40                  45

Leu Pro Tyr Ser Arg Ala Phe Gly Glu Gly Ala Ser Ala Arg Pro Arg
    50                  55                  60

Cys Cys Arg Asn Gly Gly Thr Cys Val Leu Gly Ser Phe Cys Val Cys
65                  70                  75                  80

Pro Ala His Phe Thr Gly Arg Tyr Cys Glu His Asp Gln Arg Arg Ser
            85                  90                  95
```

Glu Cys Gly Ala Leu Glu His Gly Ala Trp Thr Leu Arg Ala Cys His
                100                 105                 110

Leu Cys Arg Cys Ile Phe Gly Ala Leu His Cys Leu Pro Leu Gln Thr
            115                 120                 125

Pro Asp Arg Cys Asp Pro Lys Asp Phe Leu Ala Ser His Ala His Gly
    130                 135                 140

Pro Ser Ala Gly
145

<210> SEQ ID NO 24
<211> LENGTH: 146
<212> TYPE: PRT
<213> ORGANISM: Mus sp.

<400> SEQUENCE: 24

Tyr Gln Ser Glu Gly Asp Gly Ala Arg Glu Val Ser Asn Ile Leu Ser
1               5                   10                  15

Pro Val Ile Pro Gly Thr Thr Leu Asp Arg Thr Leu Ser Asn Ser Ser
            20                  25                  30

Arg Lys Asn Asp Ile Pro Glu Gly Ala Arg Leu Trp Asp Ser Leu Pro
        35                  40                  45

Asp Ser Ser Thr Leu Gly Glu Ser Ala Val Pro Val Ser Arg Cys Cys
    50                  55                  60

His Asn Gly Gly Thr Cys Val Leu Gly Ser Phe Cys Val Cys Pro Ala
65                  70                  75                  80

Tyr Phe Thr Gly Arg Tyr Cys Glu His Asp Gln Arg Arg Arg Asp Cys
                85                  90                  95

Gly Ala Leu Gly His Gly Ala Trp Thr Leu His Ser Cys Arg Leu Cys
                100                 105                 110

Arg Cys Ile Phe Ser Ala Leu Tyr Cys Leu Pro His Gln Thr Phe Ser
            115                 120                 125

His Cys Asp Leu Lys Ser Phe Leu Ser Ser Gly Ala Arg Gly Ser Arg
    130                 135                 140

Glu Cys
145

<210> SEQ ID NO 25
<211> LENGTH: 139
<212> TYPE: PRT
<213> ORGANISM: Homo sapiens

<400> SEQUENCE: 25

Leu Gly His Gln Glu Phe Ala Arg Pro Ser Arg Gly Tyr Leu Ala Phe
1               5                   10                  15

Arg Asp Asp Ser Ile Trp Pro Gln Glu Pro Ala Ile Arg Pro Arg
            20                  25                  30

Ser Ser Gln Arg Val Pro Pro Met Gly Ile Gln His Ser Lys Glu Leu
        35                  40                  45

Asn Arg Thr Cys Cys Leu Asn Gly Gly Thr Cys Met Leu Gly Ser Phe
    50                  55                  60

Cys Ala Cys Pro Pro Ser Phe Tyr Gly Arg Asn Cys Glu His Asp Val
65                  70                  75                  80

Arg Lys Glu Asn Cys Gly Ser Val Pro His Asp Thr Trp Leu Pro Lys
                85                  90                  95

Lys Cys Ser Leu Cys Lys Cys Trp His Gly Gln Leu Arg Cys Phe Pro
                100                 105                 110

```
Gln Ala Phe Leu Pro Gly Cys Asp Gly Leu Val Met Asp Glu His Leu
        115                 120                 125

Val Ala Ser Arg Thr Pro Glu Leu Pro Pro Ser
    130                 135

<210> SEQ ID NO 26
<211> LENGTH: 137
<212> TYPE: PRT
<213> ORGANISM: Mus sp.

<400> SEQUENCE: 26

Ala Phe Glu Phe Gly Pro Val Ala Gly Arg Asp Leu Ala Ile Arg Asp
1               5                   10                  15

Asn Ser Ile Trp Asp Gln Lys Glu Pro Ala Val Arg Asp Arg Ser Phe
            20                  25                  30

Gln Phe Val Pro Ser Val Gly Ile Gln Asn Ser Lys Ser Leu Asn Lys
        35                  40                  45

Thr Cys Cys Leu Asn Gly Gly Thr Cys Ile Leu Gly Ser Phe Cys Ala
    50                  55                  60

Cys Pro Pro Ser Phe Tyr Gly Arg Asn Cys Glu His Asp Val Arg Lys
65                  70                  75                  80

Glu His Cys Gly Ser Ile Leu His Gly Thr Trp Leu Pro Lys Lys Cys
            85                  90                  95

Ser Leu Cys Arg Cys Trp His Gly Gln Leu His Cys Leu Pro Gln Thr
            100                 105                 110

Phe Leu Pro Gly Cys Asp Gly His Val Met Asp Gln Asp Leu Lys Ala
        115                 120                 125

Ser Arg Thr Pro Cys Gln Thr Pro Ser
    130                 135
```

CRYPTIC POLYPEPTIDES AND USES THEREOF

RELATED APPLICATIONS

This application is a Continuation of U.S. application Ser. No. 15/547,258, filed on Jul. 28, 2017, which is a 371 National Stage Application of PCT/US16/015587, filed on Jan. 29, 2016, which claims priority to U.S. Provisional Application 62/109,376 filed on Jan. 29, 2015; the entire contents of these applications are incorporated herein by reference in their entirety.

SEQUENCE LISTING

The instant application contains a Sequence Listing which has been filed electronically in ASCII format and is hereby incorporated by reference in its entirety. Said ASCII copy, created on Jan. 8, 2019, is named MSS-00802_SL.txt and is 35,346 bytes in size.

BACKGROUND

Bone loss is a serious clinical problem that is most commonly diagnosed in post-menopausal woman, but that can occur in all populations at all ages. Marx (2004) *Science* 305:1420-1422 and Lotinun et al. (2012) *Curr Mol Pharmacol* 5:195-204. Diseases, such as cancer, diabetes, inflammatory bowel disease, as well as inflammatory diseases requiring steroid treatments, can suppress bone formation and lead to increased fracture risk. Fractures associated with bone loss are a leading cause of hospitalization, disability, and premature mortality in the elderly, affecting over 2 million Americans and leading to 500,000 hospitalizations and placing of 180,000 individuals into nursing homes every year. Dempster (2011) *Am J Manag Care* 17(Suppl 6):S164-S169 and Dawson-Hughes et al. (2012) *Osteoporos Int* 23:811-820. U.S. medical costs associated with osteoporotic fractures were nearly $17 billion in 2005 and are estimated to accumulate to over $474 billion in 20 years. Blume and Curtis (2011) *Osteoporo Int* 22:1835-1844. Beyond increasing fracture risk, the skeleton serves a broad array of physiologic functions, and thus bone loss may directly affect glucose and insulin metabolism, organ and vascular repair, as well as immune system function. Ferron et al. (2010) *Cell* 142:296-308; Clemens and Karsenty (2011) *J Bone Miner Res* 26:677-680; Cappariello et al. (2014) *Arch Biochem Biophys* 558:70-78; and Charles and Nakamura (2014) *Curr Osteoporos Rep* 12:1-8.

Because of the magnitude of the problem, biotechnology and pharmaceutical companies have searched for therapeutics that slow, stop, or reverse bone loss. Regrettably, only one class of approved agents restores bone mass, and all approved agents have important limitations and side effects that impact their efficacy and long-term administration. Thus, there remains an urgent need for novel therapeutics that are well tolerated and effectively stimulate bone formation to restore bone mass.

SUMMARY

The disclosure is based, at least in part, on the discovery that Cryptic protein can bind to Activin A and Activin B and inhibit the ability of Activins A and B not only to bind to their cognate cellular receptor(s), but also to signal through those receptor(s). Inhibition of Activin A has been shown to promote bone formation in vivo, and, thus, Cryptic and polypeptides comprising Cryptic (or variants and functional fragments thereof) are useful in a variety of therapeutic applications for increasing bone formation, bone mass, bone density, bone strength, and the like. For example, the polypeptides described herein are useful for treating subjects suffering from a condition associated with bone loss, such as osteoporosis or Paget's disease. Moreover, the inventors have determined that while Cryptic binds with high affinity to Activin A, Cryptic binds with lower affinity to the transforming growth factor beta superfamily proteins GDF-11 or myostatin (GDF-8) (Table 1). Inhibition of myostatin signaling in vivo has been shown to promote muscle mass, whereas inhibition of GDF-11 promotes erythropoiesis. Thus, while the disclosure is not bound by any particular theory or mechanism of action, the Cryptic polypeptides described herein are useful for treating bone disorders and have a reduced secondary effect (or no secondary effect) on muscle growth and/or erythropoiesis as compared to other Activin A inhibitors, such as soluble Activin RIIA and Activin RIIB molecules.

Accordingly, in one aspect, the disclosure features a polypeptide comprising a Cryptic protein, a functional fragment thereof, or a variant thereof. In some embodiments, the Cryptic protein is a mammalian protein (or the functional fragment or variant is derived from the mammalian Cryptic protein). In some embodiments, the Cryptic protein is a human protein (or the functional fragment or variant is derived from the human Cryptic protein). In another aspect, the disclosure features a polypeptide comprising: (i) the amino acid sequence depicted in any one of SEQ ID NOs:1 to 9, 19, or 20; (ii) a variant of the amino acid sequence depicted in any one of SEQ ID NOs: 1 to 9, 19, or 20 having not more than 40 (e.g., not more than 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1) amino acid substitutions, deletions, insertions, or a combination of any of the foregoing; or (iii) an amino acid sequence that is at least 70 (e.g., at least 75, 80, 85, 90, 95, or 99) % identical to any one of the amino acid sequences depicted in SEQ ID NOs: 1 to 9, 19, or 20.

In some embodiments, the polypeptide comprises the amino acid sequence depicted in SEQ ID NO:7, 8, or 9. In some embodiments, the polypeptide comprises an amino acid sequence that is at least 95% identical to any one of the amino acid sequences depicted in SEQ ID NOs: 1 to 9, 19 or 20. In some embodiments, the polypeptide comprises, or consists of, the amino acid sequence depicted in SEQ ID NO:10. In some embodiments, the polypeptide comprises the amino acid sequence depicted in SEQ ID NO: 19 or 20.

In some embodiments, the polypeptide comprises an amino acid sequence that comprises any one of SEQ ID NOs: 4-9, wherein the amino acid sequence is at least 70 (e.g., at least 75, 80, 85, 90, 95, or 99) % identical to the amino acid sequence depicted in SEQ ID NO: 1 or 2.

In some embodiments, the polypeptide binds to human Activin A with a $K_D$ of less than $1 \times 10^{-9}$ M, less than $1 \times 10^{-10}$ M, less than $1 \times 10^{-11}$ M, or less than $1 \times 10^{-12}$ M. In some embodiments, the polypeptide binds to human Activin A with a $K_D$ of between about 200 picomolar to about 1 picomolar (e.g., between about 200 picomolar and about 100 picomolar, between about 100 picomolar and about 50 picomolar, between about 50 picomolar and about 1 picomolar, between about 150 picomolar and 1 about picomolar). In some embodiments, the polypeptide binds to human Activin A with a $K_D$ of between about 500 picomolar and about 50 picomolar.

In some embodiments, the polypeptide has at least 5 (e.g., at least 10, 15, 20, 25, 30, 35, 40, 45, 50, 55, 60, 65, 70, 75, 80, 85, 90, 95, or 99) % of the ability of wild-type human Cryptic to inhibit human Activin A-dependent cell signaling in vitro. In some embodiments, the polypeptide has a higher affinity for human Activin A or inhibits Activin A to a higher degree than does wild-type human Cryptic (e.g., assayed as part of a fusion protein with IgG1 Fc).

In some embodiments, the polypeptide binds to human Activin B with a $K_D$ of less than $1\times10^{-9}$ M or less than, or equal to, $5\times10^{-10}$ M. In some embodiments, the polypeptide binds to human Activin B with a $K_D$ of between about 500 picomolar to about 1 nanomolar (e.g., between about 300 picomolar to about 1 nanomolar, about 200 picomolar to about 700 picomolar, or about 250 picomolar to about 800 picomolar).

In some embodiments, the polypeptide has at least 5 (e.g., at least 10, 15, 20, 25, 30, 35, 40, 45, 50, 55, 60, 65, 70, 75, 80, 85, 90, 95, or 99) % of the ability of wild-type human Cryptic to inhibit human Activin B-dependent cell signaling in vitro. In some embodiments, the polypeptide has a higher affinity for human Activin B or inhibits Activin B to a higher degree than does wild-type human Cryptic (e.g., assayed as part of a fusion protein with IgG1 Fc).

In some embodiments, the polypeptide comprises a heterologous moiety that increases the serum half-life of the polypeptide in a subject. The heterologous moiety can, in some embodiments, comprise all or part of an albumin protein. In some embodiments, the heterologous moiety comprises an immunoglobulin Fc constant region (e.g., SEQ ID NO:17 or 21). For example, in some embodiments, the polypeptide comprises the amino acid sequence depicted in SEQ ID NO:1, 2, 19, or 20, and the amino acid sequence of an Fc constant region (e.g., SEQ ID NO: 17 or 21). In some embodiments, the polypeptide comprises the amino acid sequence depicted in any one of SEQ ID NOs:4 to 9, and the amino acid sequence of an Fc constant region.

In some embodiments, a linker (e.g., one or more amino acids) can separate the Cryptic, variant, or functional fragment thereof from the heterologous moiety. In some embodiments, the linker can have the amino acid sequence depicted in SEQ ID NO:18. In some embodiments, as described below, the linker can contain a protease cleavage site, such as the cleavage site for TEV protease.

In some embodiments, the polypeptide does not include a linker sequence.

In some embodiments, the polypeptide is a fusion protein. In some embodiments, the fusion protein comprises the amino acid sequence depicted in SEQ ID NO:10.

In some embodiments, the heterologous moiety comprises polyethylene glycol (PEG).

In some embodiments, the polypeptide comprises a heterologous moiety that targets the polypeptide to bone. The heterologous moiety that targets the polypeptide to bone can comprise, e.g., the formula: $X_n$, wherein X is a canonical or noncanonical amino acid that has a negative charge at physiological pH and n is an integer from 1 to 40. X can be, e.g., aspartic acid or glutamic acid. n can be an integer between 1 and 30, e.g., 10 and 16, 2 and 20, 1 and 20, 5 and 20, 3 and 20, 5 and 15, 10 and 15, 10 and 20, 10 and 30, 10 and 25, or 10 and 30. In some embodiments, n is at least 4, 5, 6, 7, 8, 9, 10, 11, 12, 13, 14, or 15. In some embodiments, n is less than 25, 24, 23, 22, 21, 20, 19, 18, 17, 16, 15, 14, 13, 12, 11, or 10.

In some embodiments, the heterologous moiety is a detectable label.

In some embodiments, the polypeptide can be a monomer. In some embodiments, the polypeptide can, in the presence of a second copy of the polypeptide, form a dimer or multimer. For example, in embodiments in which the polypeptide is a fusion protein comprising all or part of a Cryptic polypeptide fused to an IgG Fc region, the polypeptide can dimerize by way of the Fc region. In some embodiments, the polypeptide comprises a dimerization or multimerization domain, e.g., an Fc region or any other polypeptide (or functional portion thereof) capable of dimerizing.

In another aspect, the disclosure features a pharmaceutical composition comprising any one or more of the polypeptides described herein and a pharmaceutically-acceptable carrier, excipient, or diluent.

In another aspect, the disclosure features a pre-filled syringe comprising one or more of the polypeptides described herein.

In another aspect, the disclosure features a kit comprising a pharmaceutical unit dosage form of one or more of the polypeptides described herein, a means for administering the one or more polypeptides to a subject, and, optionally, instructions for administration, e.g., self-administration.

In another aspect, the disclosure features a nucleic acid comprising a nucleotide sequence encoding any one of the polypeptides described herein. Also featured is a vector, e.g., an expression vector, comprising the nucleic acid.

In another aspect, the disclosure features a host cell comprising the vector or expression vector. The host cell can be eukaryotic (e.g., yeast, insect, mammalian, or plant) or prokaryotic. In some embodiments, the host cell is a rodent cell (CHO cell) or a non-human primate cell (COS cell). In some embodiments, the host cell is an NS0 cell.

In another aspect, the disclosure features a method for producing a polypeptide. The method comprises culturing the host cell (above) under conditions suitable for expression of the polypeptide encoded by the nucleic acid to thereby produce the polypeptide. The method can further include isolating the polypeptide from the host cell or media in which the host cell was cultured. Also featured herein is a polypeptide produced using such a method.

In yet another aspect, the disclosure features any one of the polypeptides described herein for use in the treatment of a condition associated with bone loss, lack of proper bone growth, lack of bone density, lack of bone strength, and the like. In some embodiments, the polypeptides have a reduced or negligible secondary effect on muscle growth and/or erythropoeisis (e.g., the polypeptides used at therapeutic levels for treating the condition associated with bone loss do not appreciably increase muscle mass). The disclosure also features any one or more of the polypeptides described herein for use in increasing bone growth, bone strength, or bone density in a subject (e.g., a human).

In another aspect, the disclosure features a method for increasing bone growth, bone strength, or bone density in a subject (e.g., a human). The method comprises administering to the subject in need thereof any one of the polypeptides described herein in an amount sufficient to increase bone growth, bone strength, or bone density in the subject. The subject can have a condition associated with bone loss, e.g., osteoporosis, Paget's disease, rheumatoid arthritis, a periodontal disease (e.g., gingivitis or periodontitis), bone fracture, bone deficiency, metastatic bone disease, osteoarthritis, primary or secondary hyperparathyroidism, or osteolytic bone disease. The condition can also be any of those described herein or known in the art.

In some embodiments of any of the methods or uses described herein, following administration, the composition improves a bone parameter, such as one selected from the group consisting of bone volume density, total bone surface, bone surface density, trabecular number, trabecular thickness, trabecular spacing, and total volume. In some embodiments, any of the methods and uses described herein can further comprise monitoring the subject for an improvement in any one of a number of bone parameters, such as: bone volume density, total bone surface, bone surface density, trabecular number, trabecular thickness, trabecular spacing, or total volume.

In some embodiments of the treatment of bone disorders, polypeptides that home to bone (e.g., have bone-targeting moieties) are administered to the subject.

In some embodiments, the polypeptide is administered to the subject intravenously. In some embodiments, the polypeptide is administered to the subject subcutaneously.

In some embodiments of any of the methods or uses described herein, the subject is one who has failed another treatment for a condition associated with bone loss. The treatment can be a bisphosphonate or another Activin A inhibitor (e.g., an Activin RIIA-IgG Fc fusion or an Activin RIIB-IgG Fc fusion).

In some embodiments, any of the methods or uses described herein can also comprise administering to the subject at least one additional therapeutic agent that promotes bone growth or inhibits bone resorption.

In yet another aspect, the disclosure features a method for increasing muscle mass or muscle strength in a subject in need thereof, which method comprises administering to the subject one or more of any of the polypeptides described herein in an amount sufficient to increase muscle mass or muscle strength in the subject. In some embodiments, the subject is one having a muscle disorder (e.g., a muscle wasting disorder).

In yet another aspect, the disclosure features a method for treating a subject having a muscle-wasting disorder or muscle atrophy. The method comprises administering to the subject one or more of any of the polypeptides described herein in an amount sufficient to treat the muscle-wasting disorder or muscle atrophy.

In some embodiments, the muscle-wasting condition is, or is associated with, Duchenne muscular dystrophy (DMD), multiple types of limb girdle MD (LGMD), other congenital MDs (CMD), sarcopenia, cancer cachexia, or Diabetes mellitus.

In another aspect, the disclosure features a method for treating a musculoskeletal disorder in a subject. The method includes administering to the subject one or more of any of the polypeptides described herein in an amount sufficient to treat the musculoskeletal disorder. In some embodiments, the musculoskeletal disorder is osteoporosis, osteopenia, sarcopenia, arthritis, tissue atrophy, periodontal disease, wound healing, or bone loss due to, e.g., malignancy, endocrine disorders, arthritis, immobility, or disuse.

In yet another aspect, the disclosure features a method for treating a metabolic condition, which method comprises administering to the subject one or more of any of the polypeptides described herein in an amount sufficient to treat the metabolic disorder. The metabolic disorder can be, e.g., type 2 diabetes, noninsulin-dependent diabetes mellitus, hyperglycemia, and obesity.

In another aspect, the disclosure features a method for treating a subject having an immune disorder (e.g., an inflammatory disease or autoimmune disorder). The method comprises administering to the subject one or more of any of the polypeptides described herein in an amount sufficient to treat the immune disorder. In some embodiments, the immune disorder is one associated with aberrant host defense response. In some embodiments, the immune disorder can be, e.g.: (a) acute injury of tissues inflicted by infection, toxic substances or trauma, wound healing pursuant to surgery, severe burns or other tissue injury, meningitis, appendicitis, renal tubular necrosis, traumatic brain injury and sepsis; (b) autoimmune diseases including, but not limited to, rheumatoid arthritis, multiple sclerosis, inflammatory bowel disease, vasculitis, anti-phospholipid syndrome, scleroderma, systemic lupus erythematosous and osteoarthritis; and (c) respiratory diseases including, but not limited to pneumonia, sarcoidosis, bronchiolitis obliterans, pulmonary hypertension, pneumonia, acute respiratory distress syndrome, chronic obstructive pulmonary disease (COPD), acute responses against infectious agents such as pathogenic viruses including, but not limited to, influenza A viruses H5N1 and H1N1, coronaviruses SARS, and human rhinoviruses C and D.

In yet another aspect, the disclosure features a method for treating a subject having a cancer. The method comprises administering to the subject one or more of any of the polypeptides described herein in an amount sufficient to treat the cancer. In some embodiments, the cancer comprises cancer cells that express one or more receptors for Activin A or Activin B. In some embodiments, the proliferation and/or viability of the cancer cells is positively regulated by Activin A or Activin B. In some embodiments, the methods described herein can include requesting the results of a test to determine whether cancer cells of the cancer express one or more of the receptors or are responsive to Activin A or Activin B. In some embodiments, the methods can include performing the test to determine whether cancer cells of the cancer express one or more of the receptors or are responsive to Activin A or Activin B.

In some embodiments, the cancer is a lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer.

In yet another aspect, the disclosure features any one of the polypeptides described herein for use in the treatment of a subject (e.g., a human) afflicted with muscle atrophy, a muscle wasting condition, a metabolic disorder (such as any of those described herein), an immune disorder, or a musculoskeletal disorder.

"Polypeptide," "peptide," and "protein" are used interchangeably and mean any peptide-linked chain of amino acids, regardless of length or post-translational modification.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating a condition associated with bone loss, will be apparent from the following description, the examples, and from the claims.

BRIEF DESCRIPTION OF THE SEQUENCES

SEQ ID NO:1 depicts an exemplary amino acid sequence for human Cryptic.

SEQ ID NO:2 depicts an exemplary amino acid sequence for human Cryptic without the sequence of its signal peptide.

SEQ ID NO:3 depicts an exemplary amino acid sequence for human Cryptic without the sequence of its signal peptide or C-terminal GPI anchor sequence.

SEQ ID NO:4 depicts an exemplary amino acid sequence for the low homology domain of human Cryptic.

SEQ ID NO:5 depicts an exemplary amino acid sequence for the Epidermal Growth Factor (EGF) domain of human Cryptic.

SEQ ID NO:6 depicts an exemplary amino acid sequence for the Cripto-FRL-1-Crypctic (CFC) domain of human Cryptic.

SEQ ID NO:7 depicts an exemplary amino acid sequence for a fragment of a human Cryptic polypeptide.

SEQ ID NO:8 depicts an exemplary amino acid sequence of a fragment of human Cryptic containing the EGF and CFC domains.

SEQ ID NO:9 depicts an exemplary amino acid sequence for a fragment of a human Cryptic polypeptide.

SEQ ID NO:10 depicts the amino acid sequence for an exemplary fusion polypeptide described herein.

SEQ ID NO:11 depicts an exemplary amino acid sequence of a Cryptic polypeptide expressed in Rhesus macaque.

SEQ ID NO:12 depicts an exemplary amino acid sequence of a Cryptic polypeptide expressed in mouse.

SEQ ID NO:13 depicts an exemplary amino acid sequence for the human inhibin beta A chain.

SEQ ID NO:14 depicts an exemplary amino acid sequence for the FLAG epitope tag.

SEQ ID NO:15 depicts an exemplary amino acid sequence for a polyhistidine epitope tag.

SEQ ID NO:16 depicts an exemplary amino acid sequence for an influenza hemagglutinin epitope tag.

SEQ ID NO:17 depicts an exemplary amino acid sequence for a human IgG Fc constant region.

SEQ ID NOs:18 depicts an amino acid sequence for an exemplary linker peptide.

SEQ ID NOs:19 and 20 depict amino acid sequences for an exemplary fragments of human Cryptic.

SEQ ID NO:21 depicts an amino acid sequence of a human IgG1 Fc region.

SEQ ID NO:22 depicts the amino acid sequence of an exemplary Cryptic-Fc fusion protein.

BRIEF DESCRIPTION OF THE DRAWINGS

FIG. 2 depicts the results of ligand binding experiments, and consists of six panels (FIG. 2A) Binding of Activin A to Cryptic; (FIG. 2B) Binding of Activin B to Cryptic; (FIG. 2C) Binding of GDF-8 to Cryptic; and (FIG. 2D) Binding of GDF-11 to Cryptic. (FIG. 2A-FIG. 2D) Cryptic-Fc was immobilized on the sensor chip and various concentrations of ligand as shown were injected. Curve fit of kinetic analysis is shown as orange lines. FIG. 2E depicts the superposition of ligand binding to Cryptic. FIG. 2F depicts the superposition of ligand binding to Cripto-1. (FIG. 2E-FIG. 2F) Cryptic-Fc and Cripto-1-Fc were captured on the sensor chip and all ligands as shown were injected at a concentration of 80 nM. Tested ligands included Activin A, Activin B, GDF-8, GDF-11, Nodal, BMP-9, BMP-2, BMP-4, TGFß-1, GDF-1, GDF-3. Commercially purchased Nodal, GDF-11 and GDF-3 are produced by refolding from *E. coli* and might not be adequately functional. For example, Nodal shows significant lot variability.

FIG. 3 depicts the results of receptor interaction experiments and consists of four panels FIG. 3A to FIG. 3D.

FIG. 4 depicts the results of competitive inhibition studies and consists of eight panels FIG. 4A to FIG. 4H. (FIG. 4A-FIG. 4B) ACTRIIA-Fc or ACTRIIB-Fc were captured on the sensor chip and 1 nM Activin A preincubated with 0 nM, 0.5, nM, 5 nM, 10 nM or 40 nM Fc-free Cryptic was injected. (FIG. 4C-FIG. 4F) ACTRIIA-Fc or ACTRIIB-Fc were captured on the sensor chip and 10 nM Activin B or GDF-8 preincubated with 0 nM, 5 nM, 50 nM 100 nM, 400 nM, 800 nM, or 1600 nM Fc-free Cryptic was injected.

FIG. 5 depicts the results of in vitro studies related to Cryptic-mediated regulation of Activin signaling, and consists of six panels FIG. 5A to FIG. 5F.

FIG. 6 depicts molecular models in four panels FIG. 6A to FIG. 6D. FIG. 6C is a surface model of TGF-ß family signaling. Simultaneous binding of Ligand to both type I and type II receptors initiates a phosphorylation cascade that leads to translocation of phosphorylated R-SMAD (light green) transcription factors to the nucleus and expression of target genes. FIG. 6D is a cell surface model of Cripto-1/Cryptic function. Cripto-1 and Cryptic prevent binding of type II receptors to the ligand, blocking the canonical TGF-β family signaling-cascade.

DETAILED DESCRIPTION

Figure 1A:
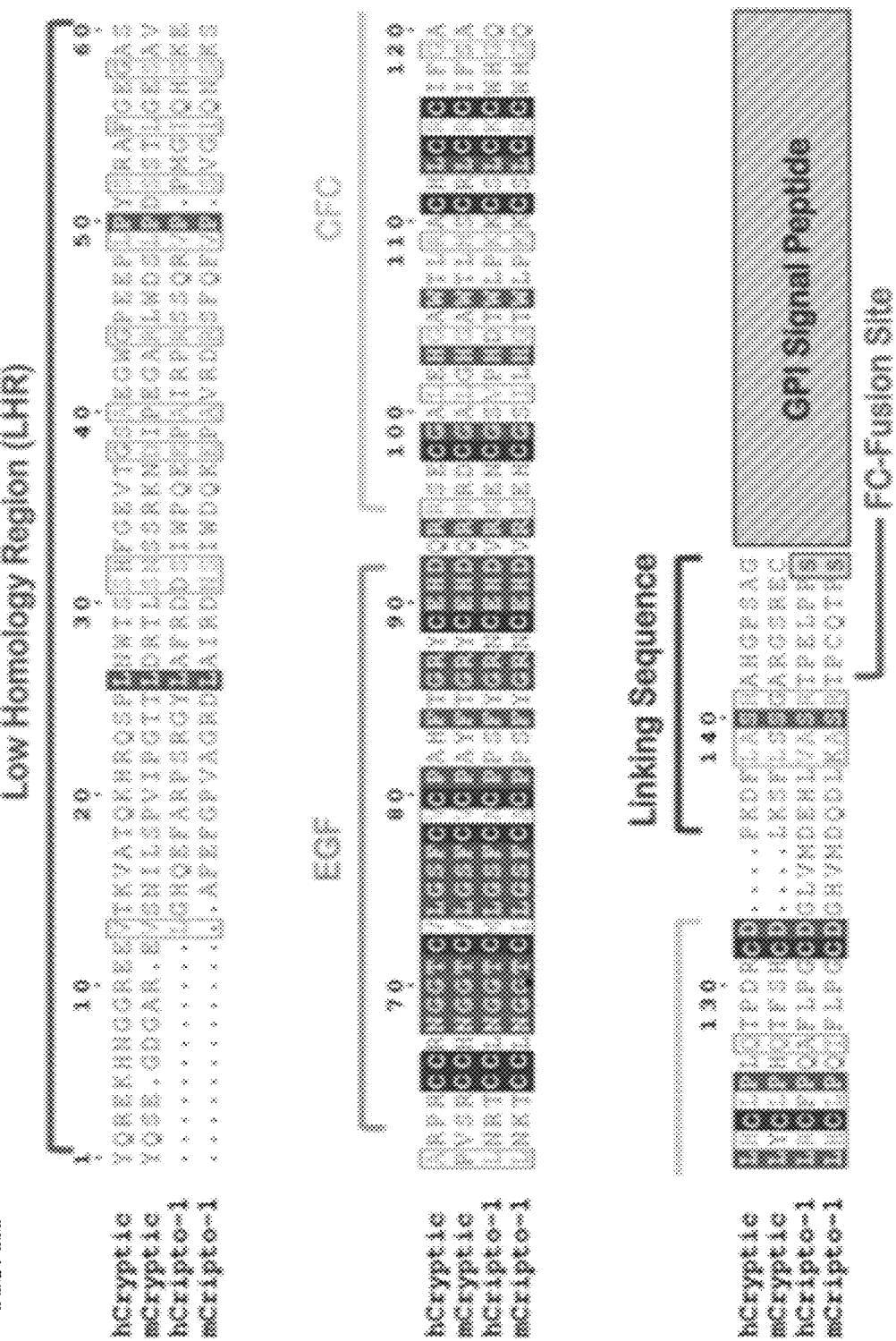
FIG. 1A discloses SEQ ID NOS 23-26, respectively, in order of appearance. Panel B depicts the domain organization of Cryptic and Cripto-1 constructs, which are colored as in A. Both molecules were fused to human Igg1-Fc via a 22 amino acid linker at the 'FC-Fusion site'. Panel C of FIG. 1 related to Cryptic-Fc and Cripto-1-Fc expressed in CHO cells. Both molecules migrate as a single, well-defined peak in a size exclusion chromatographic column. The molecular weight of each protein corresponds to the dimeric species. Non-reducing and reducing SDS-PAGE gels show the disulfide linked dimeric species and the reduced, monomeric species, respectively. Dimerization occurs via cysteines in the Fc region.

The disclosure relates to, among other things, polypeptides, nucleic acids encoding the polypeptides, production of the polypeptides, and use of the polypeptides in various applications, such as diagnostic and therapeutic methods. For example, the polypeptides are useful for treating a subject having a condition associated with bone loss, a cancer, a metabolic disorder (e.g., a disorder associated with insufficient insulin production), an immune disorder, a muscle wasting condition, or a musculoskeletal disorder. While in no way intended to be limiting, exemplary polypeptides, compositions containing the polypeptides (e.g., pharmaceutical compositions and formulations), and methods for making and using any of the foregoing are elaborated on below.

Polypeptides

The polypeptides described herein include a Cryptic polypeptide (e.g., a vertebrate Cryptic polypeptide), a functional fragment thereof, or a variant of the polypeptide or fragment. In some embodiments, a polypeptide described herein includes all or part of a human Cryptic polypeptide, e.g., one comprising the amino acid sequence:

(SEQ ID NO: 1)
MTWRHHVRLLFTVSLALQI INLGNSYQREKHNGGREEVTKVATQKHRQSP

LNWTSSHFGEVTGSAEGWGPEEPLPYSRAFGEGASARPRCCRNGGTCVLG

SFCVCPAHFTGRYCEHDQRRSECGALEHGAWTLRACHLCRCIFGALHCLP

LQTPDRCDPKDFLASHAHGPSAGGAPSLLLLLPCALLHRLLRPDAPAHPR

SLVPSVLQRERRPCGRPGLGHRL (UniProt Id. No. P0CG37).

In some embodiments, a polypeptide described herein includes all or part of a Cryptic polypeptide from any vertebrate, e.g., a reptile, a bird, or a mammal (e.g., a non-human mammal, such as a non-human primate (e.g., Rhesus macaque or Cynomolgus macaque)). Skilled artisans would appreciate that such sequences are known in the art or easily obtainable using routine experimentation (see, e.g., Sambrook et al. (infra)). In some embodiments, the polypeptide comprises all or part of a Cryptic polypeptide from Pan troglodytes, e.g., having the following amino acid sequence:

(SEQ ID NO: 11)
MTWRHHVRLLFTVSLALQI INLGNSYQREKHNGGREEVIKVATQKHQQSP

LNWTSSHFGEVTGSAEGWGPEEPLTYSWAFGEGASARPRCCRNGGTCVLG

SFCVCPAHFTGRYCEHDQRRSECGALEHGAWTLRACHLCRCIFGALHCLP

LQTPDRCDPKDFLASHAHGPSAGGAPSLLLLLPCALLHRLLRPDAPAHPR

SLVPSVLQRERRPCGRPGLGHRL (UniProt Id. No. H2QIQ5).

In some embodiments, a polypeptide described herein includes all or part of a rodent Cryptic polypeptide. For example, the polypeptide can include all or part of a murine Cryptic polypeptide, e.g., having the following amino acid sequence:

(SEQ ID NO: 12)
MRANSPTQGISLKMHQARPLFLVTVALQLIGLGYSYQSEGDGAREVSNI

LSPVIPGTTLDRTLSNSSRKNDIPEGARLWDSLPDSSTLGESAVPVSRC

CHNGGTCVLGSFCVCPAYFTGRYCEHDQRRRDCGALGHGAWTLHSCRLC

RCIFSALYCLPHQTFSHCDLKSFLSSGARGSECSIPSLLLLVLCLLLQG

VAGKG (UniProt Id. No. P97766);

In some embodiments, a polypeptide described herein comprises the following amino acid sequence: YQREKHNGGREEVTKVATQKHRQSPLNWTSSHFGEVTGSAEGWGPEEPLPYSRAF GEGASARPRCCRNGGTCVLGSFCVCPAHFTGRYCEHDQRRSECGALEHGAWTLRA CHLCRCIFGALHCLPLQTPDRCDPKDFLASHAHGPSAGGAPSLLLLLPCALLHRLLR PDAPAHPRSLVPSVLQRERRPCGRPGLGHRL (SEQ ID NO:2), which corresponds to the amino acid sequence of a human Cryptic polypeptide lacking the amino-terminal leader sequence. In some embodiments, a polypeptide described herein comprises the following amino acid sequence: YQREKHNGGREEVTKVATQKHRQSPLNWTSSHFGEVTGSAEGWGPEEPLPYSRAF GEGASARPRCCRNGGTCVLGSFCVCPAHFTGRYCEHDQRRSECGALEHGAWTLRA CHLCRCIFGALHCLPLQTPDRC (SEQ ID NO:3), which corresponds to the amino acid sequence of a human Cryptic polypeptide without the amino-terminal leader sequence or the carboxy-terminal pro-peptide domain.

In some embodiments, a polypeptide described herein comprises the following amino acid sequence: YQREKHNGGREEVTKVATQKHRQSPLNWTSSHFGEVTGSAEGWGPEEPLPYSRAF GEGASAR (SEQ ID NO:4), which corresponds to the low homology domain of a human Cryptic polypeptide. In some embodiments, a polypeptide described herein comprises the EGF domain of a Cryptic polypeptide, e.g., the EGF domain of a human Cryptic polypeptide, e.g., comprising the following amino acid sequence: PRCCRNGGTCVLGSFCVCPAHFTGRYCEHDQR (SEQ ID NO:5), which corresponds to the EGF domain of a human Cryptic polypeptide. In some embodiments, a polypeptide described herein comprises the Cripto-FRL-1-Cryptic (CFC) domain of a Cryptic polypeptide, e.g., the CFC domain of a human Cryptic polypeptide, e.g., comprising the following amino acid sequence:

(SEQ ID NO: 6)
RSECGALEHGAWTLRACHLCRCIFGALHCLPLQTPDRCDPKDFLASHA.

In some embodiments, a polypeptide described herein comprises one or more of the following amino acid sequences: CCRNGGTCVLGSFCVCPAHFTGRYCEHDQR (SEQ ID NO:7), PRCCRNGGTCVLGSFCVCPAHFTGRYCEHDQRRSECGALEHGAWTLRACHLCRCI FGALHCLPLQTPDRCDPKDFLASHA (SEQ ID NO:8), or NGGTCVLGSFC (SEQ ID NO:9). A diagram of exemplary fragments of Cryptic are set forth in FIG. 8A-8E.

In some embodiments, a polypeptide described herein comprises one or both of the following sequences: MTWRHHVRLL FTVSLALQII NLGNSYQREK HNGGREEVTK VATQKHRQSP LNWTSSHFGE VTGSAEGWGP EEPLPYSRAF GEGASARPRC CRNGGTCVLG SFCVCPAHFT GRYCEHDQRR SECGALEHGA WTLRACHLCR CIFGALHCLP LQTPDRCDPK (SEQ ID NO:19) or YQREK HNGGREEVTK VATQKHRQSP LNWTSSHFGE VTGSAEGWGP EEPLPYSRAF GEGASARPRC CRNGGTCVLG SFCVCPAHFT GRYCEHDQRR SECGALEHGA WTLRACHLCR CIFGALHCLP LQTPDRCDPK (SEQ ID NO:20).

Also featured herein are polypeptides comprising variant Cryptic polypeptides, or fragments of the variant Cryptic polypeptides. Such variants comprise one or more amino acid substitutions, insertions, or deletions, relative to the wild-type Cryptic polypeptides from which they were derived. In some embodiments, a variant polypeptide comprises at least two (e.g., at least three, four, five, six, seven, eight, nine, 10, 15, 20, 25, 30, 35, 40, 45, 50, 55, 60, 65, 70, 75, 80, 85, 90, 95, 100, or more than 100) amino acid substitutions, deletions, or insertions, relative to the wild-type Cryptic polypeptide from which it was derived (e.g., a wild-type human Cryptic polypeptide comprising the amino acid sequence depicted in SEQ ID NO:2 or 3). In some embodiments, a variant polypeptide comprises no more than 20 (e.g., no more than 19, 18, 17, 16, 15, 14, 13, 12, 11, 10, 9, 8, 7, 6, 5, 4, 3, or 2) amino acid substitutions, deletions, or insertions, relative to the wild-type Cryptic polypeptide from which it was derived (e.g., a wild-type human Cryptic polypeptide comprising the amino acid sequence depicted in SEQ ID NO:2 or 3). The substitutions can be conservative, non-conservative, or a mixture of both.

As used herein, the term "conservative substitution" refers to the replacement of an amino acid present in the native sequence in a given polypeptide with a naturally or non-naturally occurring amino acid having similar steric properties. Where the side-chain of the native amino acid to be replaced is either polar or hydrophobic, the conservative substitution should be with a naturally occurring amino acid, a non-naturally occurring amino acid that is also polar or hydrophobic, and, optionally, with the same or similar steric properties as the side-chain of the replaced amino acid. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. One letter amino acid abbreviations are as follows: alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W), tyrosine (Y); and valine (V).

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted.

In some embodiments, a polypeptide described herein comprises a variant Cryptic polypeptide having an amino acid sequence that is at least 70 (e.g., at least 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to the wild-type Cryptic polypeptide from which it was derived.

For example, in some embodiments, a variant polypeptide described herein, or a fragment thereof, has an amino acid sequence that is at least 80 (e.g., at least 81, 82, 83, 84, 85, 86, 87, 88, 89, 90, 91, 92, 93, 94, 95, 96, 97, 98, or 99) % identical to any one of the amino acid sequences depicted in SEQ ID NOs: 1 to 12.

In some embodiments, a polypeptide described herein comprises an amino acid sequence that comprises any one (or more) of the following amino acid sequences: YQREKHNGGREEVTKVATQKHRQSPLNWTSSHFGEVTGSAEGWGPEEPLPYSRAF GEGASAR (SEQ ID NO:4), PRCCRNGGTCVLGSFCVCPAHFTGRYCEHDQR (SEQ ID NO:5), RSECGALEHGAWTLRACHLCRCIFGALHCLPLQTPDRCDPKDFLASHA (SEQ ID NO:6), CCRNGGTCVLGSFCVCPAHFTGRYCEHDQR (SEQ ID NO:7), PRCCRNGGTCVLGSFCVCPAHFTGRYCEHDQRRSECGALEHGAWTLRACHLCRCI FGALHCLPLQTPDRCDPKDFLASHA (SEQ ID NO:8), or NGGTCVLGSFC (SEQ ID NO:9), wherein the amino acid sequence of the polypeptide is otherwise at least 70 (e.g., at least 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to the amino acid sequence depicted in SEQ ID NO: 1 or 2.

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software, such as BLAST software or ClustalW2. Appropriate parameters for measuring alignment, including any algorithms needed to achieve maximal alignment over the full-length of the sequences being compared can be determined by known methods.

In some embodiments, a polypeptide described herein includes a functional fragment of a Cryptic polypeptide or a variant Cryptic polypeptide. Such functional fragments, as well as variant polypeptides, retain at least 5 (e.g., at least 10, 15, 20, 25, 30, 35, 40, 45, 50, 55, 60, 65, 70, 75, 80, 85, 90, 95, or 100) % of the activity of the corresponding mature Cryptic polypeptide from which the variant or fragment was derived. For example, in some embodiments variants or functional fragments described herein retain at least 5 (e.g., at least 10, 15, 20, 25, 30, 35, 40, 45, 50, 55, 60, 65, 70, 75, 80, 85, 90, 95, or 100) % of the affinity of the mature, wild-type Cryptic polypeptide from which the variant or functional fragment was derived for Activin A and/or Activin B.

The polypeptides described herein can specifically bind to Activin A (e.g., human Activin A). The terms "specific binding," "specifically binds," and like grammatical terms, as used herein, refer to two molecules forming a complex that is relatively stable under physiologic conditions. Typically, binding is considered specific when the association constant ($k_a$) is higher than $10^6$ $M^{-1}s^{-1}$. Thus, a polypeptide described herein can specifically bind to Activin A with a $k_a$ of at least (or greater than) $10^6$ (e.g., at least or greater than $10^7$, $10^8$, $10^9$, $10^{10}$, $10^{11}$, $10^{12}$, $10^{13}$, $10^{14}$, or $10^{15}$ or higher) $M^{-1}s^{-1}$. In some embodiments, a polypeptide described herein has a dissociation constant ($k_d$) of less than or equal to $10^{-3}$ (e.g., $8 \times 10^{-4}$, $5 \times 10^{-4}$, $2 \times 10^{-4}$, $10^{-4}$, or $10^{-5}$) $s^{-1}$.

In some embodiments, a polypeptide described herein binds to Activin A (e.g., human Activin A) with a $K_D$ of less than $10^{-8}$, $10^{-9}$, $10^{-10}$, $10^{-11}$, $10^{-12}$ M, or $10^{-13}$ M. The equilibrium constant $K_D$ is the ratio of the kinetic rate constants—$k_d/k_a$. In some embodiments, a polypeptide described herein binds to Activin A with a $K_D$ of less than $1 \times 10^{-9}$ M. In some embodiments, a polypeptide described herein binds to Activin A with a $K_D$ of less than 100 picomolar, less than 50 picomolar, less than 25 picomolar, less than 10 picomolar, or less than 5 picomolar. In some embodiments, the polypeptide binds to Activin A with a $K_D$ that is between about 1 picomolar and about 100 picomolar, e.g., about 1 to about 5 picomolar, about 1 to about 10 picomolar, about 1 to about 20 picomolar, or about 1 to about 50 picomolar.

In some embodiments, a polypeptide described herein binds to Activin B (e.g., human Activin B) with a $K_D$ of less than $10^{-8}$, $10^{-9}$, or $5 \times 10^{-10}$ M. In some embodiments, a polypeptide described herein binds to Activin B with a $K_D$ of less than $1 \times 10^{-9}$ M. In some embodiments, a polypeptide described herein binds to Activin B with a $K_D$ of less than 500 picomolar.

Methods for determining whether a polypeptide binds to a target antigen and/or the affinity for a polypeptide to a target antigen are known in the art. For example, the binding of one polypeptide to a target polypeptide can be detected and/or quantified using a variety of techniques such as, but not limited to, Western blot, dot blot, plasmon surface resonance method (e.g., BIAcore system; Pharmacia Biosensor AB, Uppsala, Sweden and Piscataway, N.J.), or enzyme-linked immunosorbent assays (ELISA). Exemplary methods for evaluating the interaction of an agent and Activin A are described in, e.g., Li et al. (2010) *J Biol Chem* 285(47):36645-36655; Harrington et al. (2006) *EMBO J* 25:1035-1045; and Fischer et al. (2003) *J Endocrinol* 176: 61-68, the disclosures of each of which are incorporated herein by reference in their entirety.

The amino acid sequences for mature Activin A from several species (including human) are well known in the art. Human Activin A, for example, is a homodimer of two 13 kDa inhibin βA subunits, which is not active until the amino-terminal propeptide is cleaved from each of the subunits. An exemplary amino acid sequence for the human inhibin beta A chain is as follows:

(SEQ ID NO: 13)
MPLLWLRGFLLASCWIIVRSSPTPGSEGHSAAPDCPSCALAALPKDVPNS

QPEMVEAVKKHILNMLHLKKRPDVTQPVPKAALLNAIRKLHVGKVGENGY

VEIEDDIGRRAEMNELMEQTSEIITFAESGTARKTLHFEISKEGSDLSVV

ERAEVWLFLKVPKANRTRTKVTIRLFQQQKHPQGSLDTGEEAEEVGLKGE

RSELLLSEKVVDARKSTWHVFPVSSSIQRLLDQGKSSLDVRIACEQCQES

GASLVLLGKKKKKEEEGEGKKKGGGEGGAGADEEKEQSHRPFLMLQARQS

EDHPHRRRRRGLECDGKVNICCKKQFFVSFKDIGWNDWIIAPSGYHANYC

EGECPSHIAGTSGSSLSFHSTVINHYRMRGHSPFANLKSCCVPTKLRPMS

MLYYDDGQNIIKKDIQNMIVEECGCS
(UniProt Id. No. P08476).

Amino acids corresponding to the signal peptide are bolded and those corresponding to the propeptide are underlined.

Activin A has been described in the art and Activin A protein, which may be used in any of the methods described herein, is commercially available from a number of sources, such as affymetrix eBioscience (San Diego, Calif.) and R&D Systems (Minneapolis, Minn.).

In some embodiments, variants or functional fragments described herein retain at least 5 (e.g., at least 10, 15, 20, 25, 30, 35, 40, 45, 50, 55, 60, 65, 70, 75, 80, 85, 90, 95, or 100) % of the ability of the mature, wild-type Cryptic polypeptide from which the variant or functional fragment was derived to inhibit the binding of Activin A to its cognate cellular surface receptor(s) and/or the ability of Activin A to induce intracellular signaling through at least one of the cognate cell surface receptors for Activin A. Cell-based methods for evaluating Activin A signaling (or inhibition thereof) are known in the art and are described in, e.g., Harrington et al., supra, Schmierer et al. (2003) *J Biol Chem* 278:21197-21203; Chantry et al. (2010) *J Bone Mineral Res* 25(12): 2633-2646; and U.S. Patent Application Publication No. 20120141469. For example, cultured osteoblasts can be contacted with Activin A in the presence or absence of a Cryptic polypeptide or a variant or functional fragment thereof. The extent of osteoblast mineralization can be measured. In addition, the effect of a test inhibitor (e.g., a variant or functional fragment of Cryptic described herein) of Activin A on osteoclast number or activity can also be measured, e.g., as described in Chantry et al. (supra).

In some embodiments, variants or functional fragments described herein retain at least 5 (e.g., at least 10, 15, 20, 25, 30, 35, 40, 45, 50, 55, 60, 65, 70, 75, 80, 85, 90, 95, or 100) % of the ability of the mature, wild-type Cryptic polypeptide from which the variant or functional fragment was derived to inhibit the binding of Activin B to its cognate cellular surface receptor(s) and/or the ability of Activin B to induce intracellular signaling through at least one of the cognate cell surface receptors for Activin B. Cell-based methods for evaluating Activin B signaling (or inhibition thereof) are known in the art and are described in, e.g., Tsuchida et al. (2004) *Mol Cell Endocrinol* 220(1-2):59-65; Wacker et al. (2014) *PLoS One* 9(10):e111276; Frandsen et al. (2007) *Biochem Biophys Res Commun* 362(3):568-574; and U.S. Pat. No. 5,071,834.

As used herein, the term "inhibiting" and grammatical equivalents thereof refer to a decrease, limiting, and/or blocking of a particular action, function, or interaction. In one embodiment, the term refers to reducing the level of a given output or parameter to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The invention does not require, and is not limited to, methods that wholly eliminate the output or parameter.

In some embodiments, variants or functional fragments described herein retain at least 5 (e.g., at least 10, 15, 20, 25, 30, 35, 40, 45, 50, 55, 60, 65, 70, 75, 80, 85, 90, 95, or 100) % of the affinity of the mature, wild-type Cryptic polypeptide from which the variant or functional fragment was derived to inhibit the interaction of Activin A and/or Activin B with one of its cognate cellular receptors (e.g., ActRIIA or ActRIIB).

As used herein, the term "interaction", when referring to an interaction between two molecules, refers to the physical contact (e.g., binding) of the molecules with one another. Generally, such an interaction results in an activity (which produces a biological effect) of one or both of said molecules. To inhibit such an interaction results in the disruption of the activity of one or more molecules involved in the interaction. Inhibition can, but need not, be complete.

Functionally active variants or fragments can be obtained by screening polypeptides recombinantly produced (see below). In addition, fragments can be chemically synthesized using techniques well known in the art, such as solid phase f-Moc or t-Boc chemistry. The fragments can be produced (recombinantly or by chemical synthesis) and tested to identify those peptidyl fragments that can function as antagonists (inhibitors) of Activin A protein or signaling mediated by Activin A (and/or Activin B protein or signaling mediated by Activin B). Functionally active variants of a polypeptide can also be obtained by screening libraries of modified polypeptides recombinantly produced from the corresponding mutagenized nucleic acids encoding a Cryptic polypeptide. The variants can be produced and tested to identify those that can function as antagonists (inhibitors) of Activin A protein (or Activin B) or signaling mediated by Activin A (or Activin B).

A combinatorial library may be produced by way of a degenerate library of genes encoding a library of polypeptides which each include at least a portion of Cryptic polypeptide sequences. For instance, a mixture of synthetic oligonucleotides can be enzymatically ligated into gene sequences such that the degenerate set of potential Cryptic polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang (1983) *Tetrahedron* 39:3; Itakura et al. (1984) *Annu Rev Biochem* 53:323; Itakura et al. (1984) *Science* 198:1056; and Ike et al. (1983) *Nucleic Acid Res* 11:477). Such techniques have been employed in the directed evolution of other proteins (see, for example, Scott et al. (1990) *Science* 249:386-390; Roberts et al. (1992) *Proc Natl Acad Sci USA* 89:2429-2433; Devlin et al. (1990) *Science* 249: 404-406; Cwirla et al. (1990) *Proc Natl Acad Sci USA* 87: 6378-6382; as well as U.S. Pat. Nos. 5,223,409; 5,198,346; and 5,096, 815).

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of Cryptic polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In some embodiments, a polypeptide described herein can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK (SEQ ID NO:14)), polyhistidine (6-His; HHHHHH (SEQ ID NO:15), hemagglutinin (HA; YPYDVPDYA (SEQ ID NO:16)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of a protein agent. Alternatively, the radioactive label can be included as part of a larger molecule (e.g., $^{125}I$ in meta-[$^{125}I$]iodophenyl-N-hydroxysuccinimide ([$^{125}I$]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the agents can be modified, e.g., with a moiety that improves the stabilization and/or retention of the antibodies in circulation, e.g., in blood, serum, or other tissues. For example, an agent comprising a Cryptic polypeptide, or variant or functional fragment thereof, can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387(1-21):110-119). The stabilization moiety can improve the stability, or retention of, the polypeptide by at least 1.5 (e.g., at least 2, 5, 10, 15, 20, 25, 30, 40, or 50 or more) fold.

In some embodiments, the polypeptides described herein may contain a bone targeting agent. Agents which have an affinity for bone or an ability to home to bone are known in the art. As used herein, a "bone targeting agent" refers to a chemical structure or ligand that has a high affinity for calcium ions in hydroxyapatite, the major constituent of bone. Polypeptides can be targeted, in an embodiment, to calcium deposits in regions of the body other than bone, such as calcium deposits in the arteries, heart, kidney, or gall bladder. However, the bone targeting agent ideally selectively binds to bone tissue. A bone targeting agent is attracted to the bone tissue of the subject, preferably binds to the bone with a higher affinity than non-bone tissues, and remains bound for a certain length of time thereby delivering the composition to a bone environment. In other words, the bone targeting agent preferably binds to bone tissue with at least 2-fold greater affinity (e.g., at least 3-fold, at least 5-fold, at least 10-fold, or at least 25-fold greater affinity) than to a non-bone tissue. The bone targeting agent preferably reversibly binds to bone tissue, meaning that the bone targeting agent is eventually released from bone and expelled from the body.

In some embodiments, the bone targeting agent desirably is selected from the group consisting of a phosphate, a phosphonate, a bisphosphonate, a hydroxybisphosphonate, an aminomethylenephosphonic acid, an acidic peptide, or a combination thereof. The bone targeting agent can carry one, two, three, or more of these groups. For example, the bone targeting agent can be a phosphonate, meaning that the bone targeting agent may comprise one phosphonate, two phosphonates, or three or more phosphonates. One suitable bone targeting agent for use in the invention is EDTMP (ethylene diamine-N,N,N',N'-tetrakis(methylenephosphonic acid), currently FDA approved (Quadramet™) as the radioactive $^{153}Sm$ complex for delivering a selective radiation dose to bone metastases for pain palliation. EDTMP is a phosphonate that contains four phosphonic acid groups, and is therefore a tetraphosphonate. Compounds, such as $^{153}Sm$-EDTMP are selectively localized in bone where tumors are present versus normal bone in a ratio of more than 10:1.

In some embodiments, the bone targeting agent is a polyphosphonic acid. Polyphosphonic acid has been demonstrated to successfully target biologically-active molecules to bone tissue. For example, conjugation (via isothiocyanato chemistry) of polyaminophosphonic acids, such as ABDTMP, to growth factors (to stimulate bone formation) successfully resulted in the targeting of the growth factors to the bones of rats (see, for example, International Patent Application Publication WO 94/00145). Similarly, bone targeting agents have been coupled to proteins. For example bisphosphonates that were conjugated to human serum albumin successfully delivered the protein to bone in vitro (*Biotechnol Prog* 16:258 (2000)) and in vivo (*Biotechnol Prog* 16:1116 (2000)). The utility of bone targeting agents extends beyond delivery of proteins to bone and includes, for instance, small therapeutic molecules. A conjugate comprising a bone targeting bisphosphonate and an alkylating agent, such as BAD has been generated (see, for example, Wingen et al. (1986) *J Cancer Res Clin Oncol* 111:209).

In some embodiments, the bone targeting agent comprises the formula: $X_n$, wherein X is a canonical or noncanonical amino acid that has a negative charge at physiological pH and n is an integer from 1 to 25. In some embodiments, X is aspartic acid or glutamic acid. In some embodiments, n is an integer between 5 and 15. In some embodiments, n is an integer between 10 and 16. In some embodiments, n is at least 4 (e.g., at least 5, 6, 7, 8, 9, 10, 11, 12, 13, 14, 15, 16, 17, 18, 19, or 20). In some embodiments, n is less than 20 (e.g., less than 19, 18, 17, 16, or 15).

In other embodiments, the bone targeting agent is (aspartic acid)$_n$ or (glutamic acid)$_n$. The acid-rich peptide sequence of the glycoprotein osteonectin, which is found in abundance in bone and dentin, has a strong affinity to hydroxyapatite (Fujisawa et al. (1996) *Biochimica et Biophysica Acta* 53:1292). Thus, peptide ligands comprising acidic amino acids are suitable candidates for bone targeting agents. Indeed, (Glu)$_{10}$, when attached to biotin, successfully recruited labeled streptavidin to hydroxyapatite (described further in International Patent Application Publication No. WO 98/35703). It is believed that the (Asp)$_6$ tether to bone is metabolized during the bone resorption process mediated by osteoclasts. Therefore, the acidic peptide ligand provides not only a means of recruiting compounds to bone, but also provides a mechanism of slowly releasing compounds to bone cells and surrounding tissue.

Other examples of bone targeting agents include, but are not limited to amino- and hydroxy-alkyl phosphonic and diphosphonic acids; hydroxybisphosphonic acids including alendronate, pamidronate, 4-aminobutylphosphonic acid, 1-hydroxyethane-1,1-diphosphonic acid, and aminomethylenebisphosphonic acid; phosphates such as phytic acid; and aminomethylenephosphonic acids such as N,N-bis(methylphosphono)-4-amino-benzoic acid and nitrilotri(methylphosphonic acid).

In some embodiments, e.g., embodiments in which the bone-targeting agent is a protein, the agent can be part of the polypeptides described herein as a fusion protein (see below).

Fusion Proteins

In some embodiments, the polypeptides can be fusion proteins having at least a portion of the Cryptic polypeptides (also variants or functional fragments of the Cryptic peptides) and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. As another example, a fusion domain may be selected so as to facilitate detection of the polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some embodiments, the fusion proteins comprise a linker moiety of one or more amino acids separating the Cryptic polypeptide (variant or functional fragment) portion and the heterologous portion (e.g., the Fc region or albumin molecule). In some embodiments, the linker moiety comprises the amino acid sequence depicted in SEQ ID NO:18 (ENLYFQGGGSGGSGGDYKDDDD). In some embodiments, the linker region comprises a polyglycine sequence or poly (GS) sequence. In some cases, the fusion domains have a protease cleavage site, such as for Factor Xa, Thrombin, or Tobacco Etch Virus (TEV) protease, which allows the relevant protease to partially digest the fusion proteins and thereby liberate the recombinant proteins therefrom. The liberated proteins can then be isolated from the fusion domain by subsequent chromatographic separation. In some embodiments, an Cryptic polypeptide can be fused with a domain that stabilizes the Cryptic polypeptide in vivo (a "stabilizer" domain). By "stabilizing" is meant anything that increases serum half-life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth, as desired).

In some embodiments, the fusion protein can comprise a Cryptic polypeptide (or a variant or functional fragment thereof) fused to an Fc domain. In some embodiments, the Fc domain can comprise or consist of the following amino acid sequence:

```
                                          (SEQ ID NO: 17)
THTCPPCPAPELLGGPSVFLFPPKPKDTLMISRTPEVTCVVVD(A)VSHE

DPEVKFNWYVDGVEVHNAKTKPREEQYNSTYRVVSVLTVLHQDWLNGKEY

KCK(A)VSNKALPVPIEKTISKAKGQPREPQVYTLPPSREEMTKNQVSLT

CLVKGFYPSDIAVEWESNGQPENNYKTTPPVLDSDGPFFLYSKLTVDKSR

WQQGNVFSCSVMHEALHN(A)HYTQKSLSLSPGK.
```

In some embodiments, the Fc domain can comprise or consist of the following amino acid sequence:

```
                                          (SEQ ID NO: 21)
   KSSDKTHTCP  PCPAPELLGG  PSVFLFPPKP  KDTLMISRTP

EVTCVVVDVS  HEDPEVKFNW  YVDGVEVHNA  KTKPREEQYN

STYRVVSVLT  VLHQDWLNGK  EYKCKVSNKA  LPAPIEKTIS

KAKGQPREPQ  VYTLPPSRDE  LTKNQVSLTC  LVKGFYPSDI

AVEWESNGQP  ENNYKTTPPV  LDSDGSFFLY  SKLTVDKSRW

QQGNVFSCSV  MHEALHNHYT  QKSLSLSPGK.
```

In some embodiments, the fusion protein comprises the following amino acid sequence:

(SEQ ID NO: 10)
MTWRHHVRLL FTVSLSLQII NLGNSYQREK HNGGREEVTK

VATQKHRQSP LNWTSSHFGE VTGSAEGWGP EEPLPYSRAF

GEGASARPRC CRNGGTCVLG SFCVCPAHFT GRYCEHDQRR

SECGALEHGA WTLRACHLCR CIFGALHCLP LQTPDRCDPK

ENLYFQGGGSGGSGGDYKDDDD <u>KSSDKTHTCP PCPAPELLGG</u>

<u>PSVFLFPPKP KDTLMISRTP EVTCVVVDVS HEDPEVKFNW</u>

<u>YVDGVEVHNA KTKPREEQYN STYRVVSVLT VLHQDWLNGK</u>

<u>EYKCKVSNKA LPAPIEKTIS KAKGQPREPQ VYTLPPSRDE</u>

<u>LTKNQVSLTC LVKGFYPSDI AVEWESNGQP ENNYKTTPPV</u>

<u>LDSDGSFFLY SKLTVDKSRW QQGNVFSCSV MHEALHNHYT</u>

<u>QKSLSLSPGK</u>.

The linker sequence is in bold, whereas the Fc region of the fusion protein is underlined. The remaining sequence corresponds to a fragment of human Cryptic.

In some embodiments, the fusion protein comprises the following amino acid sequence:

(SEQ ID NO: 22)
YQREK HNGGREEVTK VATQKHRQSP LNWTSSHFGE VTGSAEGWGP

EEPLPYSRAF GEGASARPRC CRNGGTCVLG SFCVCPAHFT

GRYCEHDQRR SECGALEHGA WTLRACHLCR CIFGALHCLP

LQTPDRCDPK ENLYFQGGGSGGSGGDYKDDDD <u>KSSDKTHTCP</u>

<u>PCPAPELLGG PSVFLFPPKP KDTLMISRTP EVTCVVVDVS</u>

<u>HEDPEVKFNW YVDGVEVHNA KTKPREEQYN STYRVVSVLT</u>

<u>VLHQDWLNGK EYKCKVSNKA LPAPIEKTIS KAKGQPREPQ</u>

<u>VYTLPPSRDE LTKNQVSLTC LVKGFYPSDI AVEWESNGQP</u>

<u>ENNYKTTPPV LDSDGSFFLY SKLTVDKSRW QQGNVFSCSV</u>

<u>MHEALHNHYT QKSLSLSPGK</u>.

The linker sequence is in bold, whereas the Fc region of the fusion protein is underlined. The remaining sequence is a fragment of human Cryptic.

It may be useful, in some circumstances, to modify the immunoglobulin heavy chain constant region, for example, by mutation, deletion or other changes mediated by genetic engineering or other approaches, so that certain activities, such as complement fixation or stimulation of antibody-dependent cell-mediated cytotoxicity (ADCC) are reduced or eliminated, while preferably preserving the Fc regions' ability to bind an Fc receptor (e.g., FcRn).

In some embodiments, the Fc region (including those of an antibody or antigen-binding fragment described herein) can be an altered Fc constant region having reduced (or no) effector function relative to its corresponding unaltered constant region. Effector functions involving the Fc constant region may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent. For example, an altered Fc constant region that displays modulated ADCC and/or CDC activity may exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the Fc constant region. An altered Fc region described herein may exhibit reduced or no measurable ADCC and/or CDC activity.

In certain embodiments, the altered constant region has at least one amino acid substitution, insertion, and/or deletion, compared to a native sequence constant region or to the unaltered constant region, e.g. from about one to about one hundred amino acid substitutions, insertions, and/or deletions in a native sequence constant region or in the constant region of the parent polypeptide. In some embodiments, the altered constant region herein will possess at least about 70% homology (similarity) or identity with the unaltered constant region and in some instances at least about 75% and in other instances at least about 80% homology or identity therewith, and in other embodiments at least about 85%, 90% or 95% homology or identity therewith. The altered constant region may also contain one or more amino acid deletions or insertions. Additionally, the altered constant region may contain one or more amino acid substitutions, deletions, or insertions that results in altered post-translational modifications, including, for example, an altered glycosylation pattern (e.g., the addition of one or more sugar components, the loss of one or more sugar components, or a change in composition of one or more sugar components relative to the unaltered constant region).

Altered Fc constant regions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g., glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, 2$^{nd}$ Edition," Cold Spring Harbor Laboratory Press, Cold Spring Harbor, N.Y.; PCT publication no. WO 06/53301; and U.S. Pat. No. 7,704,497, the disclosures of each of which are incorporated herein by reference in their entirety.

Altered Fc constant regions having reduced effector function may be produced by introducing other types of changes in the amino acid sequence of certain regions of the antibody. Such amino acid sequence changes include but are not limited to the Ala-Ala mutation described in, e.g., PCT Publication nos. WO 94/28027 and WO 98/47531; and Xu et al. (2000) *Cell Immunol* 200:16-26. According to these embodiments, the Fc constant region comprises a substitution to an alanine at position 234 or a mutation to an alanine at position 235. Additionally, the altered constant region may contain a double mutation: a mutation to an alanine at position 234 and a second mutation to an alanine at position 235. In one embodiment, the Fc constant region comprises an IgG4 framework, wherein the Ala-Ala mutation would describe a mutation(s) from phenylalanine to alanine at position 234 and/or a mutation from leucine to alanine at position 235. In another embodiment, the Fc constant region comprises an IgG1 framework, wherein the Ala-Ala mutation would describe a mutation(s) from leucine to alanine at position 234 and/or a mutation from leucine to alanine at position 235. An Fc constant region may alternatively or additionally carry other mutations, including the point mutation K322A in the CH2 domain (Hezareh et al. (2001) *J Virol* 75:12161-12168).

Additional substitutions that, when introduced into a heavy chain constant region, result in decreased effector function are set forth in, e.g., Shields et al. (2001) *J Biol Chem* 276(9):6591-6604. See particularly Table 1 ("Binding of human IgG1 variants to human FcRn and FcγR) of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al. (supra)) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669 (supra).

Changes within the hinge region also affect effector functions. For example, deletion of the hinge region may reduce affinity for Fc receptors and may reduce complement activation (Klein et al. (1981) *Proc Natl Acad Sci USA* 78: 524-528). The present disclosure therefore also relates to antibodies with alterations in the hinge region.

In some embodiments, an altered Fc constant region (e.g., an altered human Fc constant region) can bind to neonatal Fc receptor (FcRn) with greater affinity than that of the native Fc constant region from which the altered or variant Fc constant region was derived. For example, the Fc constant region can comprise one or more (e.g., two, three, four, five, six, seven, or eight or more) amino acid substitutions relative to the native human Fc constant region from which the variant human Fc constant region was derived. The substitutions can increase the binding affinity of an IgG antibody containing the variant Fc constant region to FcRn at pH 6.0, while maintaining the pH dependence of the interaction. See, e.g., Hinton et al. (2004) *J Biol Chem* 279:6213-6216 and Datta-Mannan et al. (2007) *Drug Metab Dispos* 35:1-9. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., Datta-Mannan et al. (2007) *J Biol Chem* 282(3): 1709-1717; International Publication No. WO 98/23289; International Publication No. WO 97/34631; and U.S. Pat. No. 6,277,375, the disclosures of each of which are incorporated herein by reference in their entirety.

Substitutions that enhance the binding affinity of an antibody Fc constant region for FcRn are known in the art and include, e.g., (1) the M252Y/S254T/TT256E triple substitution described by Dall'Acqua et al. (2006) *J Biol Chem* 281: 23514-23524; (2) the M428L or T250Q/M428L substitutions described in Hinton et al. (2004) *J Biol Chem* 279:6213-6216 and Hinton et al. (2006) *J Immunol* 176: 346-356; and (3) the N434A or T307/E380A/N434A substitutions described in Petkova et al. (2006) *Int Immunol* 18(12):1759-69. The additional substitution pairings: P257I/Q311I, P257I/N434H, and D376V/N434H are described in, e.g., Datta-Mannan et al. (2007) *J Biol Chem* 282(3):1709-1717, the disclosure of which is incorporated herein by reference in its entirety.

In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376.

In some embodiments, the altered or variant Fc constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine, or histidine for aspartic acid at position 312; lysine, or arginine for leucine at position 314; alanine, or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid, or histidine for glycine at position 385; proline for glutamine at position 386; glutamic acid for proline at position 387; alanine, or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

It is understood that different elements of the fusion proteins may be arranged in any manner that is consistent with the desired functionality. For example, a Cryptic polypeptide may be placed C-terminal to a heterologous domain, or, alternatively, a heterologous domain may be placed C-terminal to a Cryptic polypeptide. The Cryptic polypeptide domain and the heterologous domain need not be adjacent in a fusion protein, and additional domains or amino acid sequences may be included C- or N-terminal to either domain or between the domains.

Polypeptide Expression

A recombinant polypeptide (e.g., fragments or fusion proteins) can be produced using a variety of techniques known in the art of molecular biology and protein chemistry. For example, a nucleic acid encoding a fusion protein can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of recombinant polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as *bovine* papillomavirus (Sarver et al. (1982) *Proc Natl Acad Sci USA*, 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include CaPO$_4$ precipitation, liposome fusion, cationic liposomes, electroporation, viral infection, dextran-mediated transfection, polybrene-mediated transfection, protoplast fusion, and direct microinjection.

Appropriate host cells for the expression of recombinant proteins include yeast, bacteria, insect, plant, and mammalian cells (e.g., rodent cell lines, such as Chinese Hamster Ovary (CHO) cells). Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, a recombinant protein can be expressed in, and purified from, transgenic animals (e.g., transgenic mammals). For example, a recombinant protein can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

A polypeptide can be produced from the cells by culturing a host cell transformed with the expression vector containing nucleic acid encoding the polypeptide, under conditions, and for an amount of time, sufficient to allow expression of the proteins. Such conditions for protein expression will vary with the choice of the expression vector and the host cell, and will be easily ascertained by one skilled in the art through routine experimentation. For example, proteins expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. A fusion protein described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the recombinant proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a prokaryotic or eukaryotic cell expressing the proteins. Typically, a polypeptide is purified when it constitutes at least 60 (e.g., at least 65, 70, 75, 80, 85, 90, 92, 95, 97, or 99) %, by weight, of the total protein in a sample.

The recombinant proteins can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, 3$^{rd}$ edition," Springer-Verlag, New York City, N.Y. The degree of purification necessary will vary depending on the desired use. In some instances, no purification of the expressed proteins will be necessary.

Methods for determining the yield or purity of a purified protein are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

In some embodiments, endotoxin can be removed from the protein preparations. Methods for removing endotoxin from a protein sample are known in the art and exemplified in the working examples. For example, endotoxin can be removed from a protein sample using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), Mira-CLEAN® Endotoxin Removal Kit (Mirus), or Acrodisc™—Mustang® E membrane (Pall Corporation).

Methods for detecting and/or measuring the amount of endotoxin present in a sample (both before and after purification) are known in the art and commercial kits are available. For example, the concentration of endotoxin in a protein sample can be determined using the QCL-1000 Chromogenic kit (BioWhittaker), the limulus amebocyte lysate (LAL)-based kits such as the Pyrotell®, Pyrotell®-T, Pyrochrome®, Chromo-LAL, and CSE kits available from the Associates of Cape Cod Incorporated.

Pharmaceutical Compositions and Formulations

The compositions described herein can be formulated as a pharmaceutical solution, e.g., for administration to a subject for enhancing an immune response to an antigen. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see e.g., Berge et al. (1977) *J Pharm Sci* 66:1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filtered sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions described herein are administered in an aqueous solution by parenteral injection. The disclosure features pharmaceutical compositions comprising an effective amount of the agent (or more than one agent) and optionally include pharmaceutically acceptable diluents, preservatives, solubilizers, emulsifiers, adjuvants and/or carriers. Such compositions include sterile water, buffered saline (e.g., Tris-HCl, acetate, phosphate), pH and ionic strength; and optionally, additives such as detergents and solubilizing agents (e.g., TWEEN® 20, TWEEN 80, Polysorbate 80), anti-oxidants (e.g., ascorbic acid, sodium metabisulfite), and preservatives (e.g., thimersol, benzyl alcohol) and bulking substances (e.g., lactose, mannitol). The formulations may be sterilized, e.g., using filtration, incorporating sterilizing agents into the compositions, by irradiating the compositions, or by heating the compositions.

As described above, relatively high concentration compositions can be made. For example, the compositions can be formulated at a concentration of between about 10 mg/mL to 100 mg/mL (e.g., between about 9 mg/mL and 90 mg/mL; between about 9 mg/mL and 50 mg/mL; between about 10 mg/mL and 50 mg/mL; between about 15 mg/mL and 50 mg/mL; between about 15 mg/mL and 110 mg/mL; between about 15 mg/mL and 100 mg/mL; between about 20 mg/mL and 100 mg/mL; between about 20 mg/mL and 80 mg/mL; between about 25 mg/mL and 100 mg/mL; between about 25 mg/mL and 85 mg/mL; between about 20 mg/mL and 50 mg/mL; between about 25 mg/mL and 50 mg/mL; between about 30 mg/mL and 100 mg/mL; between about 30 mg/mL and 50 mg/mL; between about 40 mg/mL and 100 mg/mL; between about 50 mg/mL and 100 mg/mL; or between about 20 mg/mL and 50 mg/mL). In some embodiments, compositions can be formulated at a concentration of greater than 5 mg/mL and less than 50 mg/mL. Methods for formulating a protein in an aqueous solution are known in the art and are described in, e.g., U.S. Pat. No. 7,390,786; McNally and Hastedt (2007), "Protein Formulation and Delivery," Second Edition, Drugs and the Pharmaceutical Sciences, Volume 175, CRC Press; and Banga (1995), "Therapeutic peptides and proteins: formulation, processing, and delivery systems," CRC Press. In some embodiments, the aqueous solution has a neutral pH, e.g., a pH between, e.g., 6.5 and 8 (e.g., between and inclusive of 7 and 8). In some embodiments, the aqueous solution has a pH of about 6.6, 6.7, 6.8, 6.9, 7, 7.1, 7.2, 7.3, 7.4, 7.5, 7.6, 7.7, 7.8, 7.9, or 8.0. In some embodiments, the aqueous solution has a pH of greater than (or equal to) 6 (e.g., greater than or equal to 6.1, 6.2, 6.3, 6.4, 6.5, 6.6, 6.7, 6.8, 6.9, 7, 7.1, 7.2, 7.3, 7.4, 7.5, 7.6, 7.7, 7.8, or 7.9), but less than pH 8.

As used herein, "about" and like grammatical terms refers to an acceptable degree of error for the quantity measured given the nature or precision of the measurements. Exemplary degrees of error include up to 20% (e.g., no more than 19, 18, 17, 16, 15, 14, 12, 11, 10, 9, 8, 7, 6, 5, 4, 3, 2, 1, or less than 1%). In some embodiments, e.g., in biological systems, about includes values that are within an order of magnitude, e.g., within 4-fold, 3-fold, or 2-fold. In some embodiments, "about" refers to a value no more than 100% of the stated reference value.

Nucleic acids encoding a therapeutic polypeptide can be incorporated into a gene construct to be used as a part of a gene therapy protocol to deliver nucleic acids that can be used to express and produce agents within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO04/060407) carried out in vivo. Examples of suitable retroviruses include pLJ, pZIP, pWE and pEM which are known to those skilled in the art (see, e.g., Eglitis et al. (1985) Science 230:1395-1398; Danos and Mulligan (1988) Proc Natl Acad Sci USA 85:6460-6464; Wilson et al. (1988) Proc Natl Acad Sci USA 85:3014-3018; Armentano et al. (1990) Proc. Natl. Acad. Sci. USA 87:6141-6145; Huber et al. (1991) Proc Natl Acad Sci USA 88:8039-8043; Ferry et al. (1991) Proc Natl Acad Sci USA 88:8377-8381; Chowdhury et al. (1991) Science 254:1802-1805; van Beusechem et al. (1992) Proc Natl Acad Sci USA 89:7640-7644; Kay et al. (1992) Human Gene Therapy 3:641-647; Dai et al. (1992) Proc Natl Acad Sci USA 89:10892-10895; Hwu et al. (1993) J Immunol 150:4104-4115; U.S. Pat. Nos. 4,868,116 and 4,980,286; PCT Publication Nos. WO89/07136, WO89/02468, WO89/05345, and WO92/07573). Another viral gene delivery system utilizes adenovirus-derived vectors (see, e.g., Berkner et al. (1988) BioTechniques 6:616; Rosenfeld et al. (1991) Science 252:431-434; and Rosenfeld et al. (1992) Cell 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) Am J Respir Cell Mol Biol 7:349-356; Samulski et al. (1989) J Virol 63:3822-3828; and McLaughlin et al. (1989) J Virol 62:1963-1973.

In some embodiments, compositions can be formulated with one or more additional therapeutic agents, e.g., additional agents for increasing bone formation, bone density, or bone mass.

When compositions are to be used in combination with a second active agent, the compositions can be coformulated with the second agent or the compositions can be formulated separately from the second agent formulation. For example, the respective pharmaceutical compositions can be mixed, e.g., just prior to administration, and administered together or can be administered separately, e.g., at the same or different times (see below).

Kits

The disclosure also pertains to packaged pharmaceutical compositions or kits for administering any one or more of the polypeptides described herein, e.g., for the treatment of a condition associated with bone loss or any other condition described herein (e.g., a cancer, a metabolic disorder, a muscle wasting disorder, a musculoskeletal disorder, or an immune disorder). In some embodiments, the kit comprises one or more of the polypeptides described herein and instructions for administration of polypeptide(s) for treatment of the condition. The instructions may describe how, e.g., subcutaneously or intravenously, and when, e.g., at week 0, week 2, week 4, etc., the different doses of the one or more polypeptides shall be administered to a subject for treatment.

Another aspect of the invention pertains to kits containing a pharmaceutical composition comprising one or more of the polypeptides described herein and a pharmaceutically acceptable carrier, and one or more pharmaceutical compositions each comprising an additional therapeutic agent useful for treating a condition associated with bone loss, and a pharmaceutically acceptable carrier. Alternatively, the kit comprises a single pharmaceutical composition comprising one or more of the polypeptides described herein, one or more drugs useful for treating a subject in need thereof (e.g., a subject having a condition associated with bone loss), and a pharmaceutically acceptable carrier. The instructions may describe how, e.g., subcutaneously, and when, e.g., at week 0, week 2, week 4, etc., the different doses of the one or more polypeptides and/or the additional therapeutic agent shall be administered to a subject for treatment. The kit may contain instructions for dosing of the pharmaceutical compositions for the treatment of a condition described herein, e.g., a condition associated with bone loss.

In some embodiments, the kit comprises one or more reagents and/or instructions for testing for an improvement in at least one indicia of bone growth, bone density, bone strength, bone formation, etc.

Therapeutic Applications

The polypeptides described herein can be used in a number of therapeutic applications. For example, the polypeptides can increase bone formation, bone mass, bone density, bone strength, and the like. As such, the polypeptides are useful in a variety of therapeutic applications, e.g., for treating or preventing a disease or condition associated with bone loss, insufficiency, or damage. For example, the Cryptic polypeptides described herein are useful for treating subjects suffering from a condition associated with bone loss, such as osteoporosis or Paget's disease. In some embodiments, the disclosure provides methods of treating or preventing bone damage in an individual in need thereof through administering to the individual a therapeutically effective amount of a polypeptide described herein. In some embodiments, the disclosure provides methods of promoting bone growth or mineralization in an individual in need thereof through administering to the individual a therapeutically effective amount of a polypeptide described herein. These methods are preferably aimed at therapeutic and prophylactic treatments of animals, and more preferably, humans. In some embodiments, the disclosure provides for the use of a polypeptide described herein for the treatment of disorders associated with low bone density or decreased bone strength.

The compositions described herein can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount", in an in vivo setting, means a dosage sufficient to treat, inhibit, or alleviate one or more symptoms of the disorder being treated or to otherwise provide a desired pharmacologic and/or physiologic effect (e.g., treat a condition associated with bone loss). The precise dosage will vary according to a variety of factors such as subject-dependent variables (e.g., age, immune system health, etc.), the disease, and the treatment being effected. Therapeutically effective amounts of the agents disclosed herein treat, ameliorate one or more symptoms, or prevent (e.g., delay the onset or reduce the severity of onset of symptoms) a condition described herein, such as condition associated with bone loss.

Suitable human doses of any of the antibodies or fragments thereof described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such compositions can be determined by known pharmaceutical procedures in cell cultures or experimental animals (e.g., animal models of bone disorders). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Agents that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the polypeptides that include the ED50 with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the IC50 (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration is desired, cell culture or animal modeling can be used to determine a dose required to achieve a therapeutically effective concentration within the local site.

In some embodiments of any of the methods described herein, an agent can be administered to a mammal in conjunction with one or more additional therapeutic agents (e.g., therapeutic agents for treating bone diseases).

As used herein, a subject is preferably a human, but can also be a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is a domesticated animal or a farm animal. In some embodiments, the mammal is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (e.g., treatment with one or more of the polypeptides described herein). In some embodiments, that subject is one who is diagnosed as having a condition described herein, such as a condition associated with bone loss.

The term "preventing" is art-recognized, and when used in relation to a condition, is well understood in the art, and includes administration of a composition which reduces the frequency of, or delays the onset of, symptoms of a medical condition in a subject relative to a subject which does not receive the composition.

Also provided herein are methods for inducing bone and/or cartilage formation, preventing bone loss, increasing bone mineralization or preventing the demineralization of bone. For example, the polypeptides described herein can be used to treat osteoporosis and to mend bone fractures and cartilage defects in humans and other animals. The polypeptides may be useful in patients that are diagnosed with subclinical low bone density as a protective measure against the development of osteoporosis.

In some embodiments, one or more of the polypeptides described herein are useful for healing bone fractures and cartilage defects in humans and other animals. In some embodiments, the polypeptides described herein can be used in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. In some embodiments, one or more of the polypeptides can be used to treat osteoporosis.

Conditions associated with bone loss include, without limitation, osteoporosis (including secondary osteoporosis), hyperparathyroidism, Cushing's disease, Paget's disease, thyrotoxicosis, chronic diarrheal state or malabsorption, renal tubular acidosis, or anorexia nervosa. Osteoporosis may be caused by, or associated with, various factors. Being female, particularly a post-menopausal female, having a low body weight, and leading a sedentary lifestyle are all risk factors for osteoporosis (loss of bone mineral density, leading to fracture risk). Persons having any of the following profiles may be candidates for treatment with one or more of the polypeptides described herein: a post-menopausal woman and not taking estrogen or other hormone replacement therapy; a person with a personal or maternal history of hip fracture or smoking; a post-menopausal woman who is tall (over 5 feet 7 inches) or thin (less than 125 pounds); a man with clinical conditions associated with bone loss; a person using medications that are known to cause bone loss, including corticosteroids such as Prednisone™, various antiseizure medications such as Dilantin™ and certain barbiturates, or high-dose thyroid replacement drugs; a person having type 1 diabetes, liver disease, kidney disease or a family history of osteoporosis; a person having high bone turnover (e.g., excessive collagen in urine samples); a person with a thyroid condition, such as hyperthyroidism; a person who has experienced a fracture after only mild trauma; a person who has had x-ray evidence of vertebral fracture or other signs of osteoporosis.

As noted above, osteoporosis can also result as a condition associated with another disorder or from the use of certain medications. Osteoporosis resulting from drugs or another medical condition is known as secondary osteoporosis. In a condition known as Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenyloin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Bone loss resulting from cancer therapy is widely recognized and termed cancer therapy induced bone loss (CTIBL). Bone metastases can create cavities in the bone that may be corrected by treatment with one or more of the polypeptides described herein. Thus, polypeptides described herein are also useful for treating bone loss associated with cancer.

In some embodiments, the polypeptides can be used to increase muscle mass or strength in a subject in need thereof. For example, the polypeptides are useful for treating a subject having a muscle wasting disorder. In some embodiments, the subject (e.g., a human) to be treated has a muscle wasting disorder or suffers from muscle atrophy. A muscle wasting disorder, as used herein, encompasses disorders or conditions in which muscle wasting is one of the primary symptoms, such as muscular dystrophy, spinal cord injury, neurodegenerative diseases, anorexia, sarcopenia, cachexia, muscular atrophy due to immobilization, prolonged bed rest, or weightlessness, and the like, as well as disorders in which an abnormally high fat-to-muscle ratio is implicated in a disease or pre-disease state, e.g., Type II diabetes or Syndrome X.

Atrophy of skeletal muscle occurs in muscles of adult animals as a result of lack of use, aging, starvation, and as a consequence of a variety of diseases, disorders, and conditions such as sepsis, muscular dystrophy, AIDS, aging, and cancer. The loss of muscle is generally characterized by decreases in protein content, force production, fatigue resistance, and muscle fiber diameter. These decreases can be attributed to both a decrease in protein synthesis and an increase in protein degradation. Muscle wasting and related conditions to which the compositions and methods of the invention are directed include any condition in which enhanced muscle growth, or diminishment of muscle wasting, produces a therapeutically or otherwise desirable result. Conditions include muscular dystrophy, sarcopenia, cachexia, diabetes mellitus, and the improvement of muscle mass where such improvement is ethical and desirable, e.g., in food animals.

One class of muscle wasting disorders, as mentioned above, are the muscular dystrophies. These are a heterogeneous group of neuromuscular disorders, which include the most common type, Duchenne muscular dystrophy (DMD), multiple types of limb girdle MD (LGMD) and other congenital MDs (CMD). Progressive muscle damage and muscle loss, tissue inflammation and replacement of healthy muscle with fibrous and fatty tissues result in muscle wasting in muscular dystrophy. Extreme muscle loss is one of the most prominent signs of the disease, and leads to complications and symptoms, including death.

Sarcopenia is the age-related loss of muscle mass, strength and function. It begins in the fourth decade of life and accelerates after the age of approximately 75 years. Many factors, including physical inactivity, motor-unit remodeling, decreased hormone levels, and decreased protein synthesis, may all contribute to sarcopenia. With the exception of physical inactivity, all of these may be subject to genetic control where gene modulation may be useful. For example, the rate of muscle protein synthesis and protein breakdown affects sarcopenia. The balance of protein synthesis and breakdown determines the protein content in the body. Research has consistently reported that muscle protein synthesis rates are lower in older adults when compared to younger adults. A decrease in muscle protein catabolism, effected by, e.g., gene modulation, could result in slowing or reversal of the loss of muscle mass.

Cachexia is a condition associated with a variety of serious diseases, including cancer, AIDS, septicemia and congestive heart failure. Its major effect is massive loss of both adipose tissue and skeletal muscle, which is not caused by malnutrition. Cachexia contributes to nearly one-third-of all cancer deaths. In a process that is not yet well understood, cytokines and tumor factors mediate wasting by suppressing muscle gene products. Cachectic factors have been shown to be selective in targeting the myosin heavy chain. Cachexia involves a complex disruption of several systems that also leads to anemia, insulin resistance, immunosuppression, and activation of an acute-phase response. The resulting progressive weakness can make patients with cancer more susceptible to the toxic effects of radiation and chemotherapy; many such patients die from cachexia-related syndromes, rather than from their tumors.

As noted above, the polypeptides described herein bind to and inhibit the activity of Activin A and Activin B. Activins has been shown to regulate insulin production by pancreatic islets. Tsuchida et al. (2004) *Mol Cell Endocrinol* 220(1-20):59-65 and Wu et al. (2014) *Diabetologia* 57(1):148-156. Thus, while the disclosure is not bound by any particular theory or mechanism of action, the polypeptides described herein can also be useful for treating a metabolic disorder, such as a disorder associated with insufficient insulin production. The metabolic disorder can be, e.g., type 2 diabetes, noninsulin-dependent diabetes mellitus, hyperglycemia, and obesity.

In another aspect, the disclosure features a method for treating a subject having an immune disorder (e.g., an inflammatory disease or autoimmune disorder). The method comprises administering to the subject one or more of any of the polypeptides described herein in an amount sufficient to treat the immune disorder. In some embodiments, the immune disorder is one associated with aberrant host defense response. In some embodiments, the immune disorder can be, e.g.: (a) acute injury of tissues inflicted by infection, toxic substances or trauma, wound healing pursuant to surgery, severe burns or other tissue injury, meningitis, appendicitis, renal tubular necrosis, traumatic brain injury and sepsis; (b) autoimmune diseases including, but not limited to, rheumatoid arthritis, multiple sclerosis, inflammatory bowel disease, vasculitis, anti-phospholipid syndrome, scleroderma, systemic lupus erythematosous and osteoarthritis; and (c) respiratory diseases including, but not limited to pneumonia, sarcoidosis, bronchiolitis obliterans, pulmonary hypertension, pneumonia, acute respiratory distress syndrome, chronic obstructive pulmonary disease (COPD), acute responses against infectious agents such as pathogenic viruses including, but not limited to, influenza A viruses H5N1 and H1N1, coronaviruses SARS, and human rhinoviruses C and D. See, e.g., European patent application publication no. 2594280.

The polypeptides are also useful for treating a subject afflicted with a proliferative disorder, such as a cancer. In some embodiments, the mammal is one who has, is suspected of having, or is at risk for developing a cancer or an infection. Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., neuroblastoma), melanoma, thyroid cancer, ovarian cancer, testicular cancer, prostate cancer, cervical cancer, vaginal cancer, or bladder cancer. Hematological cancers (liquid tumors) include, e.g., leukemias (e.g., chronic lymphocytic leukemia such as B cell or T cell type chronic lymphocytic leukemia) and multiple myeloma. Bone cancers include, without limitation, osteosarcoma and osteocarcinomas.

In some embodiments, the cancer comprises cancer cells that express one or more receptors for Activin A and/or Activin B. In some embodiments, the cancer comprises cancer cells whose proliferation (e.g., rate or magnitude of proliferation) and/or viability is positively affected by Activin A or Activin B. See, e.g., Togashi et al. (2015) *Cancer Lett* 356(2 Pt B):819-827; Marino et al. (2014) *Mol Hum Reprod* 20(12):1223-1237; Kang et al. (2009) *J Bone Miner Res* 24(7):1180-1193; Hoda et al. (2012) *Br J Cancer* 107:1978-1986; and Wildi et al. (2001) *Gut* 49(3):409-417. Methods for detecting the presence or expression level of activin receptors by cancer cells are known in the art and described in, e.g., Wildi et al., supra.

Gene expression can be detected as, e.g., protein or mRNA expression of a protein of interest. That is, the presence or expression level (amount) of a protein can be determined by detecting and/or measuring the level of mRNA or protein expression.

A variety of suitable methods can be employed to detect and/or measure the level of mRNA expression of a protein. For example, mRNA expression can be determined using Northern blot or dot blot analysis, reverse transcriptase-PCR (RT-PCR; e.g., quantitative RT-PCR), in situ hybridization (e.g., quantitative in situ hybridization) or nucleic acid array (e.g., oligonucleotide arrays or gene chips) analysis. Details of such methods are described below and in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; Gibson et al. (1999) *Genome Res* 6(10):995-1001; and Zhang et al. (2005) *Environ Sci Technol* 39(8):2777-2785; U.S. Patent Application Publication No. 2004086915; European Patent No. 0543942; and U.S. Pat. No. 7,101,663; the disclosures of each of which are incorporated herein by reference in their entirety.

In one example, the presence or amount of one or more discrete mRNA populations in a biological sample can be determined by isolating total mRNA from the biological sample (see, e.g., Sambrook et al. (supra) and U.S. Pat. No. 6,812,341) and subjecting the isolated mRNA to agarose gel electrophoresis to separate the mRNA by size. The size-separated mRNAs are then transferred (e.g., by diffusion) to a solid support such as a nitrocellulose membrane. The presence or amount of one or more mRNA populations in the biological sample can then be determined using one or more detectably-labeled polynucleotide probes, complementary to the mRNA sequence of interest, which bind to and thus render detectable their corresponding mRNA populations. Detectable labels include, e.g., fluorescent (e.g., fluorescein, fluorescein isothiocyanate, rhodamine, dichlorotriazinylamine fluorescein, dansyl chloride, allophycocyanin (APC), or phycoerythrin), luminescent (e.g., europium, terbium, Qdot™ nanoparticles supplied by the Quantum Dot Corporation, Palo Alto, Calif.), radiological (e.g., 125I, 131I, 35S, 32P, 33P, or 3H), and enzymatic (horseradish peroxidase, alkaline phosphatase, beta-galactosidase, or acetylcholinesterase) labels.

In another example, the presence or amount of discrete populations of mRNA in a biological sample can be determined using nucleic acid (or oligonucleotide) arrays. For example, isolated mRNA from a biological sample can be amplified using RT-PCR with random hexamer or oligo(dT)-primer mediated first strand synthesis. The RT-PCR step can be used to detectably-label the amplicons, or, optionally, the amplicons can be detectably labeled subsequent to the RT-PCR step. For example, the detectable label can be enzymatically (e.g., by nick translation or a kinase such as T4 polynucleotide kinase) or chemically conjugated to the amplicons using any of a variety of suitable techniques (see, e.g., Sambrook et al., supra). The detectably-labeled amplicons are then contacted to a plurality of polynucleotide probe sets, each set containing one or more of a polynucleotide (e.g., an oligonucleotide) probe specific for (and capable of binding to) a corresponding amplicon, and where the plurality contains many probe sets each corresponding to a different amplicon. Generally, the probe sets are bound to a solid support and the position of each probe set is predetermined on the solid support. The binding of a detectably-labeled amplicon to a corresponding probe of a probe set indicates the presence or amount of a target mRNA in the biological sample. Additional methods for detecting mRNA expression using nucleic acid arrays are described in, e.g., U.S. Pat. Nos. 5,445,934; 6,027,880; 6,057,100; 6,156,501; 6,261,776; and 6,576,424; the disclosures of each of which are incorporated herein by reference in their entirety.

Methods of detecting and/or for quantifying a detectable label depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

RNA can be extracted from the tissue sample by a variety of methods, e.g., the guanidium thiocyanate lysis followed by CsCl centrifugation (Chirgwin et al. 1979, Biochemistry 18:5294-5299). RNA from single cells can be obtained as described in methods for preparing cDNA libraries from single cells, such as those described in Dulac (1998) Curr Top Dev Biol 36:245 and Jena et al. (1996) J Immunol Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In certain embodiments, the biological sample contains polypeptide molecules from the test subject. Alternatively, the biological sample can contain mRNA molecules from the test subject or genomic DNA molecules from the test subject.

In other embodiments, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

The expression of a fusion protein can also be determined by detecting and/or measuring expression of a protein (e.g., a fusion protein). Methods of determining protein expression generally involve the use of antibodies specific for the target protein of interest. For example, methods of determining protein expression include, but are not limited to, western blot or dot blot analysis, immunohistochemistry (e.g., quantitative immunohistochemistry), immunocytochemistry, enzyme-linked immunosorbent assay (ELISA), enzyme-linked immunosorbent spot (ELISPOT; Coligan et al., eds. (1995) Current Protocols in Immunology. Wiley, N.Y.), or antibody array analysis (see, e.g., U.S. Patent Application Publication Nos. 20030013208 and 2004171068, the disclosures of each of which are incorporated herein by reference in their entirety). Further description of many of the methods above and additional methods for detecting protein expression can be found in, e.g., Sambrook et al. (supra).

In one example, the presence or amount of protein expression can be determined using a western blotting technique. For example, a lysate can be prepared from a biological sample, or the biological sample itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In another example, an immunoassay can be used for detecting and/or measuring the protein expression of a protein. As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, sepharose, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here as above, the presence or amount of bound detectably-labeled antibody indicates the presence or amount of protein in the biological sample.

Methods for generating antibodies or antibody fragments specific for a protein can be generated by immunization, e.g., using an animal, or by in vitro methods such as phage display. A polypeptide that includes all or part of a target protein can be used to generate an antibody or antibody fragment. The antibody can be a monoclonal antibody or a preparation of polyclonal antibodies.

Methods for detecting or measuring gene expression can optionally be performed in formats that allow for rapid preparation, processing, and analysis of multiple samples. This can be, for example, in multi-welled assay plates (e.g., 96 wells or 386 wells) or arrays (e.g., nucleic acid chips or protein chips). Stock solutions for various reagents can be provided manually or robotically, and subsequent sample preparation (e.g., RT-PCR, labeling, or cell fixation), pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting the presence or level of a target protein in a cell) can utilize ArrayScan® VTI HCS Reader or KineticScan® HCS Reader technology (Cellomics Inc., Pittsburg, Pa.).

As used herein, a subject "at risk for developing" a cancer is a subject having one or more (e.g., two, three, four, five, six, seven, or eight or more) risk factors for developing a cancer. For example, a subject at risk of developing a cancer may have a predisposition to develop a cancer (i.e., a genetic predisposition to develop a cancer such as a mutation in a tumor suppressor gene (e.g., mutation in BRCA1, p53, RB, or APC) or has been exposed to conditions that can result in the condition. Thus, a subject can be one "at risk of developing a cancer when the subject has been exposed to mutagenic or carcinogenic levels of certain compounds (e.g., carcinogenic compounds in cigarette smoke such as acrolein, arsenic, benzene, benz[a]anthracene, benzo[a]pyrene, polonium-210 (Radon), urethane, or vinyl chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., glioblastoma such as glioblastoma multiforme), melanoma, thyroid cancer, ovarian cancer, testicular cancer, prostate cancer, cervical cancer, vaginal cancer, or bladder cancer.

A subject "suspected of having" a cancer or an infection is one having one or more symptoms of the cancer or infection. It should be understood that mammal at risk for developing, or suspected of having, a cancer or an infection does not include all mammals within the species of interest.

In some embodiments, the polypeptides described herein can be administered as part of a broader therapeutic regimen inclusive of one or more additional therapies for an indication of interest. That is, a polypeptide described herein may be conjointly administered with other pharmaceutical agents. Conjoint administration may be accomplished by administration of a single co-formulation, by simultaneous administration or by administration at separate times.

In some embodiments, the polypeptides described herein may be particularly advantageous if administered with other bone-active agents. A patient may benefit from conjointly receiving one or more of the polypeptides described herein and taking calcium supplements, vitamin D, appropriate exercise and/or, in some cases, other medication. Examples of other medications include, bisphosphonates (e.g., alendronate, ibandronate and risedronate), calcitonin, estrogens, parathyroid hormone and raloxifene (see above).

In some embodiments, the polypeptides described herein can be administered with one or more anti-cancer therapies. Suitable anti-cancer therapies include, e.g., chemotherapeutic agents, ionizing radiation, immunotherapy agents, or hyperthermotherapy. Chemotherapeutic agents include, but are not limited to, aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, taxol, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into groups, including, for example, the following: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disrupters such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF)-inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disrupters.

The term "immunotherapeutic agent" can include any molecule, peptide, antibody or other agent which can stimulate a host immune system to generate an immune response to a tumor or cancer in the subject. Various immunotherapeutic agents are useful in the compositions are known in the art and include, e.g., PD-1 and/or PD-1L inhibitors, CD200 inhibitors, CTLA4 inhibitors, and the like. Exemplary PD-1/PD-L1 inhibitors (e.g., anti-PD-1 and/or anti-PD-L1 antibodies) are known in the art and described in, e.g., International Patent Application Publication Nos. WO 2010036959 and WO 2013/079174, as well as U.S. Pat. Nos. 8,552,154 and 7,521,051, the disclosures of each of which as they relate to the antibody descriptions are incorporated herein by reference in their entirety. Exemplary CD200 inhibitors are also known in the art and described in, e.g., International Patent Application Publication No. WO 2007084321. Suitable anti-CTLA4 antagonist agents are described in International Patent Application Publication Nos. WO 2001/014424 and WO 2004/035607; U.S. Patent Application Publication No. 2005/0201994; and European Patent No. EP 1212422. Additional CTLA-4 antibodies are described in U.S. Pat. Nos. 5,811,097, 5,855,887, 6,051,227, and 6,984,720;

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In some embodiments, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In some embodiments, hyperthermia, a procedure in which body tissue is exposed to high temperatures (up to 106° F.) is used to treat the cancer or is selected as a therapy for the subject. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In some embodiments, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about three centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In some embodiments, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser: This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser: light from this laser can penetrate deeper into tissue than light from the other types of lasers, and it can cause blood to clot quickly. It can be carried through optical fibers to less accessible parts of the body. This type of laser is sometimes used to treat throat cancers. Argon laser: this laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The following examples are intended to illustrate, not to limit, this disclosure.

EXAMPLES

Example 1. Materials and Methods

TGF-β Family Ligands.

Recombinant Activin A, Activin B, Nodal (3218-ND-025/CF), GDF-1 (6937-GD-010/CF), GDF-3 (958-G3-010), GDF-8, GDF-11 (1958-GD-010/CF), TGF-ß-1, BMP-2 (355-BM-010/CF), BMP-4 (314-BP-010/CF), and BMP-9 (3209-BP-010/CF) were obtained from R&D Biosystem. Nodal, GDF-3 and GDF-11 are produced in E. coli whereas all other ligands, were expressed using mammalian cells. (In some instances, different lots of material produced in E. coli had different activity.)

Expression Plasmids.

Synthetic human ACTRIIA-hIgG-Fc, ACTRIIB-hIgG-Fc, ALK4-hIgg-Fc, and Cryptic-hIgG-Fc genes were obtained from Life Technologies (GeneArt®). Fusion constructs included extracellular domains (ECD) of human ACTRIIA (amino acids 1-120), ACTRIIB (amino acids 1-120), ALK4 (amino acids 1-110), and Cryptic (amino acids 1-155). Functional domains were linked to human IgG1 Fc (SEQ ID NO: 21) via a 22 amino acid long linker (SEQ ID NO:18) containing a TEV cleavage site, a glycine/serine rich region, and a FLAG-tag. Cripto-1 and BMPRII were cloned from cDNA obtained from Thermo Scientific. An amplicon encompassing Cripto1 (1-161) and BMPRII (1-120) was fused to hIgG1-Fc domain using PCR.

Protein Purification.

ACTRIIA-Fc, ACTRIIB-Fc, ALK4-Fc, BMPRII-Fc, Cryptic-Fc, and Cripto-1-Fc, as well as Activin A, Activin B, GDF-8, TGF-ß-1 were purified from condition medium (CHO cell culture) using Protein A capture. Proteins were eluted with 100 mM Glycine pH 3.0 and immediately neutralized with 2 M Tris, pH 9.0. Immobilized Metal Affinity Chromatography was used to capture Nodal from conditioned medium. Proteins were further purified or analyzed by size exclusion chromatography to ascertain monodispersity. Purified proteins were dialyzed into phosphate-buffered saline, pH 7.5 and stored at −20° C. or −80° C. The purity of the proteins was checked with SDS-PAGE or Western Blot under reducing and non-reducing conditions. For inhibition assays, the Fc portion from Fc fusion proteins was removed using Tobacco Etch Virus (TEV) protease followed by Protein A affinity and size exclusion chromatography.

Cell Lines.

A204 cells (HTB-82) and HOS cells (CRL-1543) were obtained from ATCC. Cells were maintained according to ATCC (American Type Culture Collection) culture conditions (RPMI medium supplemented with 10% FBS, 0.2 units/ml bovine insulin (SigmaAldrich, 11070-73-8) and 1% penicillin/streptomycin (P/S) mixture). For osteoblast studies, HOS cells were maintained in alpha-MEM with 10% FBS and 1% P/S. Cells were grown at 37° C. under humidified, 5% $CO_2$ atmosphere. Freshly thawed cells were passaged at least three times before performing assays.

Immunoblotting.

$2.0 \times 10^5$ cells were plated in 24-well plates and grown to 80% confluence in complete medium, washed with 1×PBS, starved overnight and grown for additional 24 hour in serum free medium with or without 39 nM Activin A or Activin B. Cells were treated with 17.8 or 178 nM Cryptic-1-Fc or ACTRIIA-Fc. Protein lysate was prepared by using ice-cold RIPA lysis buffer (150 mM NaCl, 1% NP40, 0.1% sodium dodecyl sulfate (SDS), 0.5% sodium deoxycholate, 50 mM Tris pH 8.0, 1× 'Recom ProteaseArrest' protease inhibitor cocktail (G-Biosciences, 786-436) and 2× 'PhosphataseArrest' phosphastase inhibitor cocktail (G-Biosciences, 786-450)). Cell lysates were stored at −80° C. Protein concentration of lysates was determined using Bradford. For Western blotting, equal amounts of protein were separated on 'AnykD' SDS-polyacrylamide gels (Bio-Rad, 456-9035) under reducing conditions and transferred to Hybond-P membranes (GE Healthcare, RPN2020F). Membranes were blocked with 5% BSA and incubated with primary anti-phospho-Smad2 (Cell Signaling, 3108S), anti-Smad2 (Cell Signaling, 5339S) or anti-Actin (Cell Signaling, 3108S) antibodies at 1:1000 dilution, followed by incubation with Horseradish peroxidase conjugated secondary antibody at 1:2000 dilution. WesternBright ECL HRP substrate was used for detection (Advansta, K-12043-D20). Western blots were visualized by exposing the gel to autoradiography film (Denville, E3018). Immunoblots were quantified using ImageJ software.

Surface Plasmon Resonance.

Receptor-ligand binding affinities were determined by SPR using the Biacore 2000. Anti-human IgG (Fc) antibody was immobilized onto four channels of a CM5 chip using amine coupling chemistry. Purified Cripto-1-Fc, Cryptic-Fc, ACTRIIA-Fc, ACTRIIB-Fc, BMPRII-Fc or ALK4-Fc were captured on the experimental flow channels. A reference channel was monitored to account for nonspecific binding, drift, and bulk shifts. For kinetic analysis of ligand binding, a concentration series of ligands (Nodal, Activin A, Activin B, GDF-1, GDF-3, GDF-8, GDF-11, TGF-ß-1, BMP-4, BMP-2 and BMP-9) was injected over experimental and control flow channels at 50 µl/min flow rate. For analysis of Cripto-1 or Cryptic binding to receptors, Fc-free Cripto-1 or Cryptic at a concentration of 5 µM was injected over experimental and control flow channels at 50 µl/min flow rate. For kinetic analysis of ligand binding in the presence of Cripto-1 or Cryptic, a concentration series of ligands (Nodal, Activin A) combined with excess Cripto-1 or Cryptic (200 nM) was injected over experimental and control flow channels at 50 µl/min flow rate. For inhibition analysis 1 nM Nodal, Activin A or Activin B was combined with 0 nM, 0.5, 5, 10, 40, 50, 100 or 400 nM Fc-free Cripto-1 or Cryptic. The pre-assembled ligand-Cryptic complexes were injected over experimental and control flow channels at 50 µl/min flow rate. After each binding cycle, the antibody surface was regenerated to base line. All experiments were carried out at 25° C. HBS-EPS buffer (0.01 M HEPES, 0.5 M NaCl, 3 mM EDTA, 0.005% (v/v) Tween 20, pH 7.4) containing 0.1% BSA was used as running buffer. *E. coli* Nodal containing samples were kept without BSA, as the presence of BSA causes rapid inactivation of recombinant Nodal. Sensograms were analyzed by double referencing. To obtain kinetic rate constants, the processed data was fitted to 1:1 Langmuir interaction model with mass transport limitation using Scrubber, Clamp or BiaEvaluation software. The equilibrium binding constant $K_d$ was determined by calculating the ratio of binding rate constants $k_d/k_a$. Results are summarized in Table 1 (below).

Reporter Assays.

About 50,000 A204 cells (ATCC) in complete medium (McCoy's 5A medium (Invitrogen) supplemented with 10% fetal calf serum) were seeded in each well of a 96-well plate and grown overnight. The next day, a solution containing 200 ng pNL[NlucP/SBE/Hygro] Vector (experimental luciferase reporter plasmid, firefly luciferase, Promega), 2 ng pNL[NLucP/minP/Hygro] Vector (control luciferase reporter plasmid, renilla luciferase, Promega), 24 µl lipofectamine 2000 (Life Technologies), and 960 µl McCoy's 5A medium (Life Technologies) was prepared and incubated at room temperature for 30 minutes. After incubation, 3840 µl McCoy's 5A medium was added to the transfection solution, cells were washed with 1× PBS, and 50 µl transfection solution was added to each well. Transfection reagent containing medium was removed the following day, cells were washed with 1×PBS, and medium was replaced with serum free McCoy's 5A medium containing test proteins. After 16 h incubation at 37° C., luciferase activity was detected with the Dual-Glo Luciferase Assay System (Promega). Chemiluminescence was measured using an Infinite M200 plate reader. Relative luciferase units were calculated by dividing firefly luciferase units (FLU) with renilla luciferase units (RLU).

Osteoblast Mineralization Analyses.

HOS cells were plated at 100,000 cells per well of a 12 well plate. Upon reaching confluency, medium was supplemented with 2 mM phosphate and 25 µg/ml ascorbic acid. Cells were treated with each feeding (every 2-3 days) for 2 weeks with vehicle, 20 µg/ml Cryptic or 50 ng/ml Activin A alone or together. Cells were rinsed with PBS and fixed in 10% formalin for 30 minutes at room temperature. Cells were incubated for 1 hour with freshly made 20 mM alizarin red staining solution, rinsed and digitally photographed. Stain was removed with 10% cetylpyridinium chloride and quantitated at 570 nm wavelength.

Statistics.

Cell-based assays were performed in quadruplicates and were repeated at least two different times. Statistical significance was determined using a two-tailed T-test. P values <than 0.05 were considered statistically significant.

Example 2. Cryptic and Cripto-1 Expression and Purification

Figure 1B:
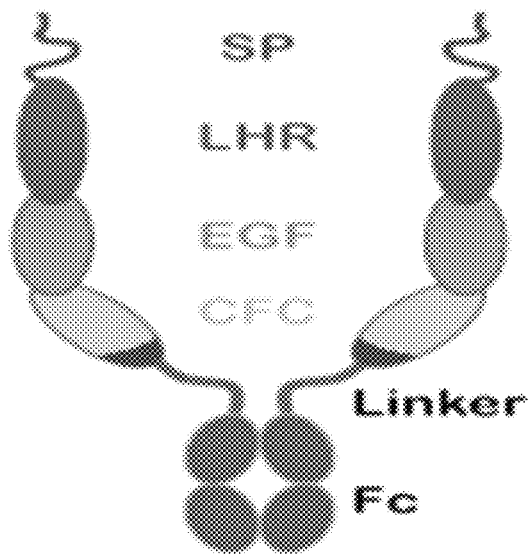
FIG. 1 consists of three panels: panel (A), panel (B), and panel (C), which depict construct design and fusion protein purification. In panel A, a multiple sequence alignment of human and mouse Cryptic and Cripto-1 is shown. Both molecules have a signal peptide for secretion (not shown in the alignment), a Low Homology domain (teal), an EGF-like domain (orange), a CFC-domain (grey), and a GPI signal peptide (represented by the purple box). The Cripto-1 GPI signal peptide is cleaved after Ser169 (residues in yellow box). Cryptic of primate origin has a large, noncanonical GPI signal peptide and its GPI modified amino acid is not known. For expression constructs, Cripto-1 and Cryptic were truncated at the 'FC-Fusion site' (light blue).
Figure 1C:
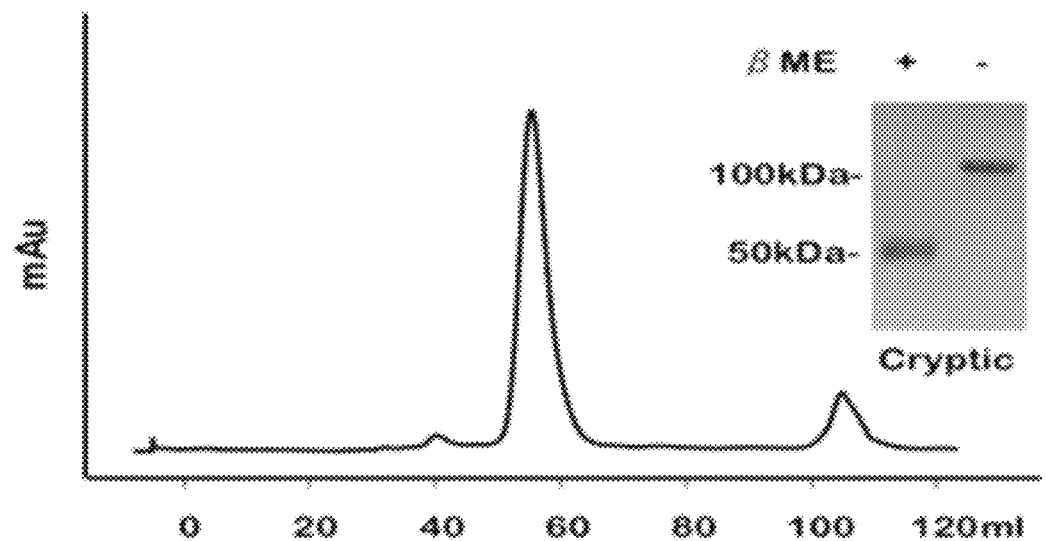

Cryptic and Cripto-1 are secreted proteins that are attached to the membrane via a Glycosylphosphatidylinositol (GPI) anchor (FIG. 1A). A soluble form of human Cryptic and Cripto-1 were expressed in Chinese Hamster Ovary (CHO) cells stably transfected with a nucleic acid encoding the soluble forms. The soluble forms included the extracellular domain of the protein and the Fc portion from human IgG1, linked to each other via a 22-amino acid linker containing a Tobacco Etch Mosaic Virus (TEV) cleave site (FIG. 1B). For Cryptic, a construct was created that included the N-terminal signal peptide and ended at alanine 167. For Cripto-1, the signal peptide of Cryptic was used and ended the construct at threonine 163, analogous to Cryptic residue alanine 167 (FIG. 1A). Cryptic-Fc and Cripto-1-Fc proteins were purified from conditioned medium by Protein A affinity chromatography, followed by size exclusion chromatography. Approximately 100 mg of purified Cryptic-Fc and 30 mg of Cripto-1-Fc per liter was obtained of culture cells. Preparative size-exclusion chromatography (SEC) showed that Cryptic could be obtained in an aggregate free form (FIG. 1C). Coomassie-stained SDS-PAGE gels of the purified proteins showed bands of approximately 50 kDa under reducing and approximately 100 kDa under non-reducing conditions, as expected (FIG. 1C).

Example 3. Cryptic and Cripto-1 Bind Distinct Ligands

Figure 2A:
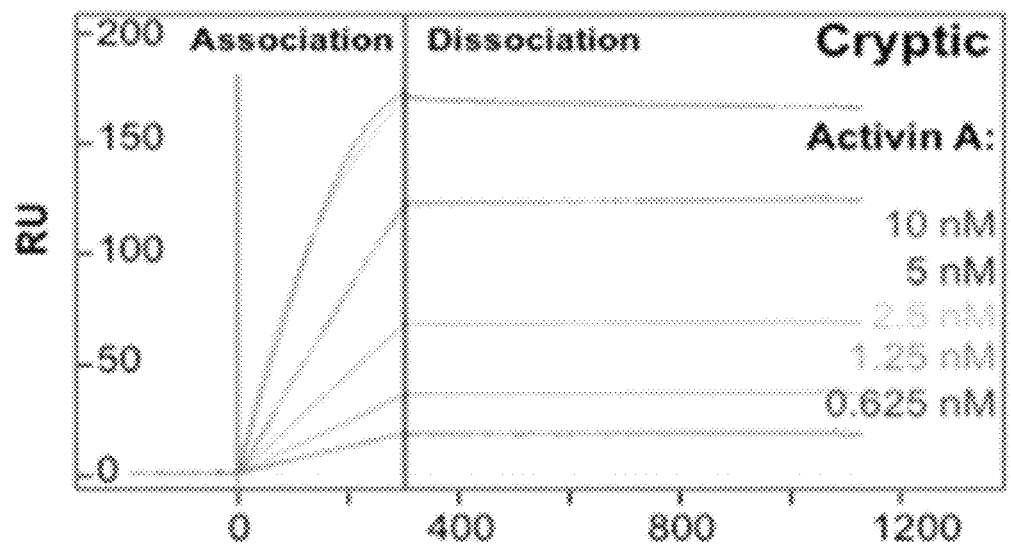
FIG. 2A to FIG. 2F.
Figure 2B:
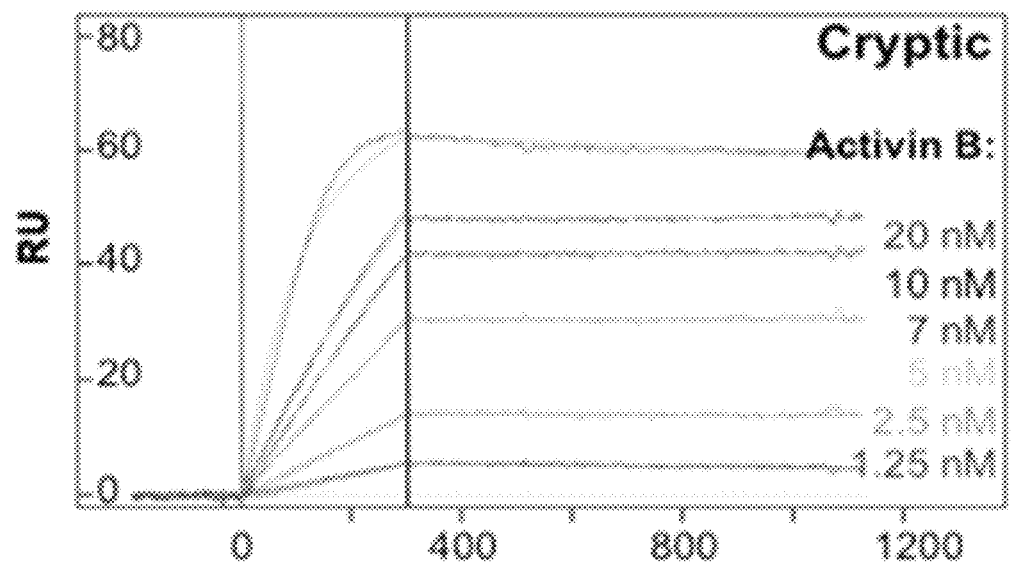
Figure 2C:
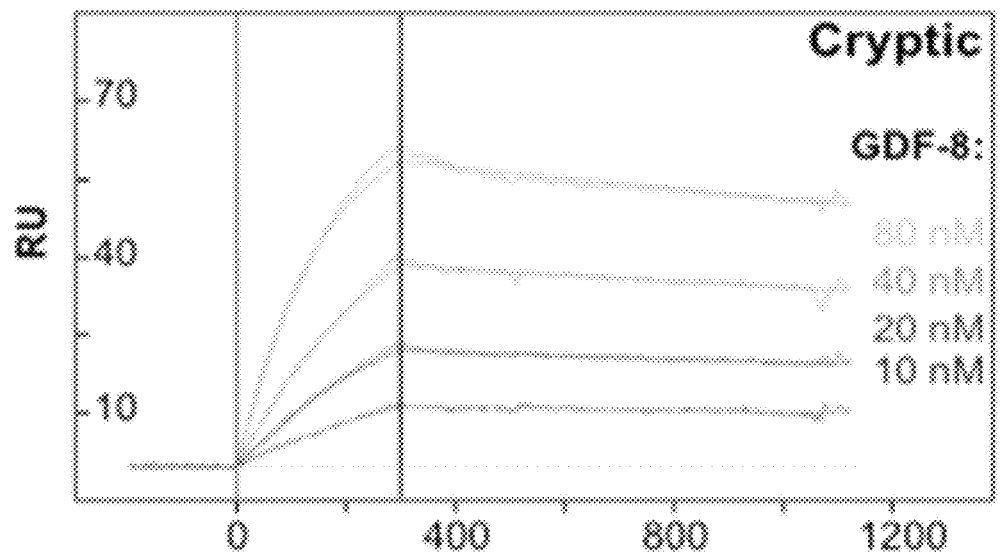
Figure 2D:
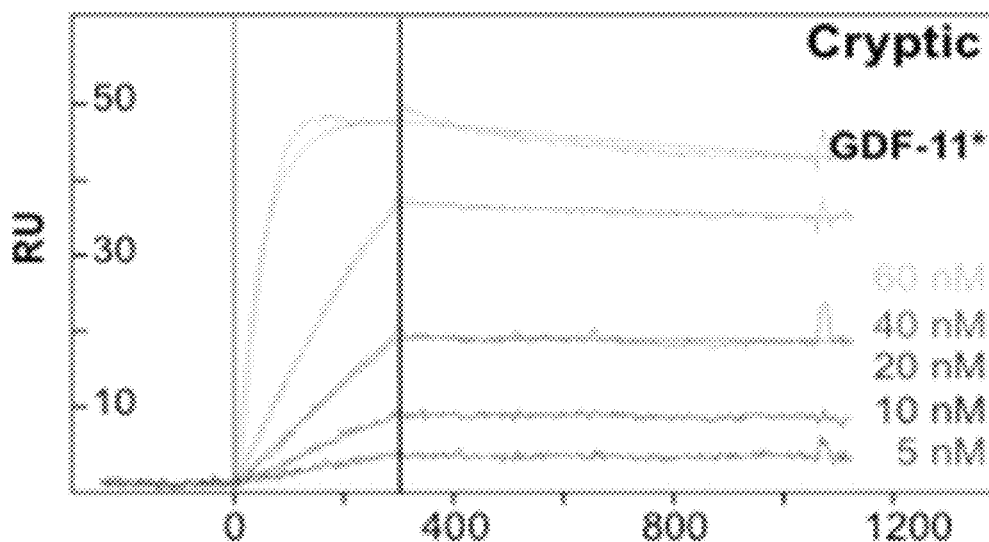
Figure 2E:
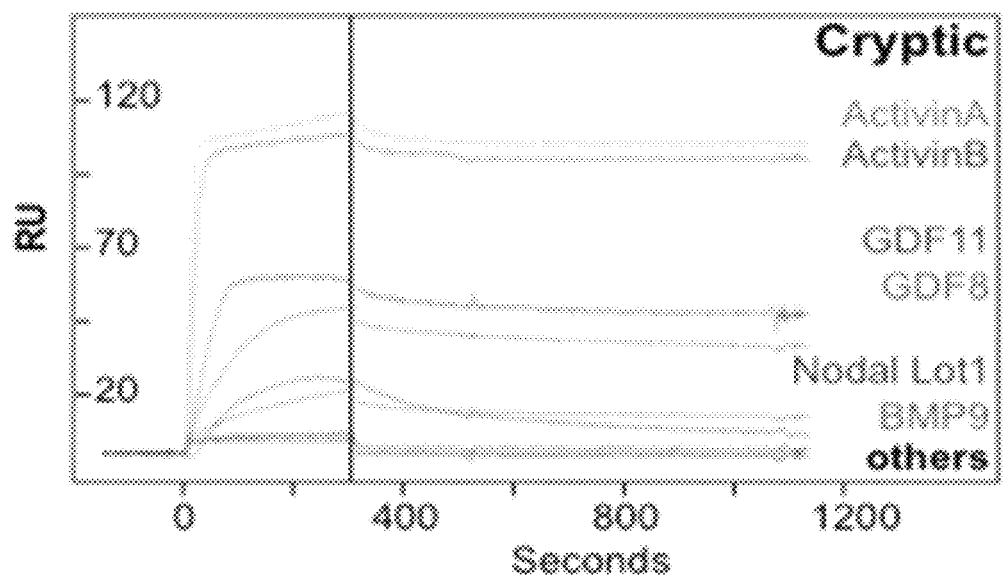
Figure 2F:
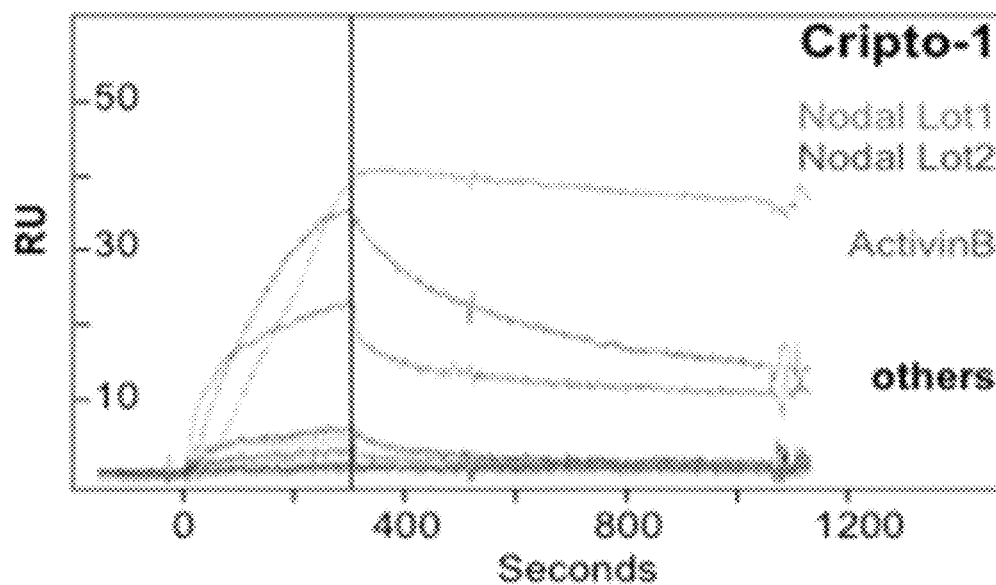

Surface Plasmon Resonance (SPR) was used to characterize the ligand-binding specificities of human Cryptic and Cripto-1. The purified Fc fusion proteins were captured on a CM5 sensor chip cross-linked with an anti-hFc antibody and subsequently injected different TGFβ family ligands over the captured Cryptic and Cripto-1 at various concentrations, including concentrations that far exceeded serum levels (45-47) (FIG. 2, Table 1). Cryptic was shown to bind Activin A and Activin B with very high affinities ($k_a$=3.1× $10^5$ ($M^{-1}s^{-1}$), $k_d$=4.6×$10^{-5}$ ($s^{-1}$), $K_d$=0.15 nM and $k_a$=3.1× $10^5$ ($M^{-1}s^{-1}$), $k_d$=4.6×$10^{-5}$ ($s^{-1}$), $K_d$=0.15 nM), respectively) (FIG. 2A and FIG. 2B). In addition, Cryptic also bound GDF-8 and GDF-11, albeit with much lower affinity than Activin A and Activin B (FIG. 2C and FIG. 2D). Nevertheless, the interaction between Cryptic and GDF-8 or GDF-11 is relatively stable, as indicated by slow dissociation rates ($k_d$=4.6×$10^{-4}$ and 4.6×$10^{-4}$($s^{-1}$), respectively. Cryptic also bound Nodal; however, the Cryptic-Nodal interaction was several orders of magnitude weaker than the Nodal-Cripto-1 interaction (FIG. 2E and FIG. 2F). Cryptic did not bind appreciably to any other tested TGF-ß family ligand, such as TGF-ß-1, GDF-1, GDF-3, BMP-2, BMP-4 and BMP-9 (FIG. 2E). These findings indicate that Activin A and Activin B are the principal ligands that are regulated by Cryptic in humans, and that Cryptic could also play a role in the regulation of GDF-8 and GDF-11 signaling.

A similar experiment was performed with human Cripto-1, which revealed that its ligand binding specificity is clearly distinct from that of Cryptic. Of all tested ligands only Nodal bound to human Cripto-1 with appreciable affinity (FIG. 2F). Activin B also bound Cripto-1, however this interaction is unstable as reflected by its fast dissociation rates ($k_d$=4.6× $10^{-5}$ ($s^{-1}$)). Binding of Cripto-1 to any other tested TGF-ß family ligand, including Activin A, was not observed. These findings therefore indicate that Cripto-1 is very specific for Nodal.

Example 4. Cryptic does not Regulate Ligand Binding to ALK4

Figure 3A:
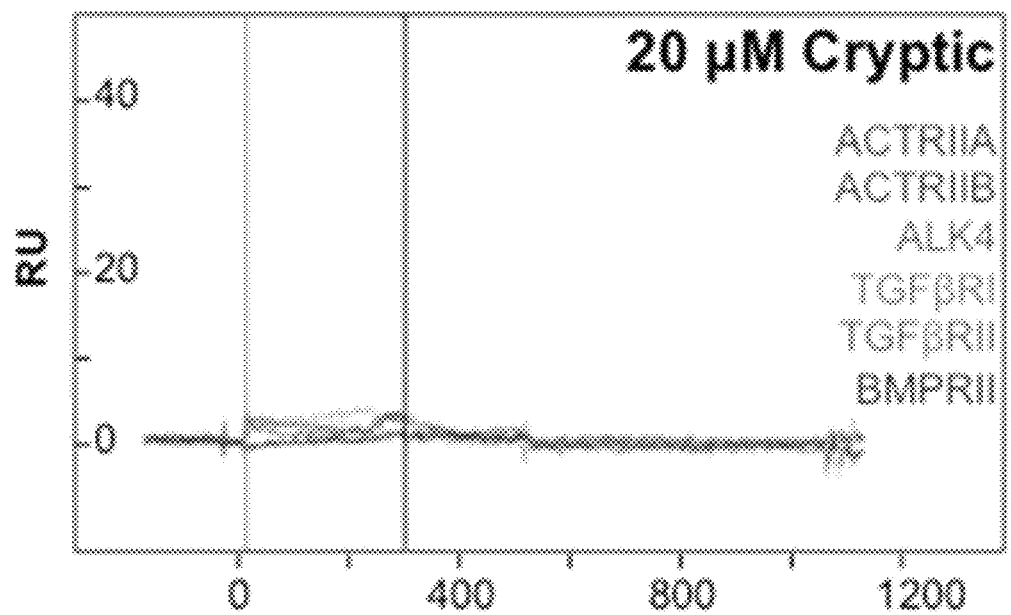
FIG. 3A depicts the binding of Cryptic to TGF-β family receptors. Type I receptors ALK4-Fc, and ALK5-Fc, and type II receptors ACTRIIA-Fc, ACTRIIB-Fc, BMPRII-Fc, and TGF-βRII-Fc were captured on the sensor chip. Fc free Cryptic was injected at a concentration of 20 µM.

To establish the role of Cryptic in the ligand-ALK4 interaction, human ALK4-Fc was captured on a sensor chip. To determine whether Cryptic binds ALK4, Fc-free Cryptic was injected at various concentrations. In the absence of ligand and other factors, no binding of Cryptic to ALK4 was detected, even at concentrations that far exceeded physiological levels (e.g. 20 µM) (FIG. 3A). These findings demonstrate that Cryptic does not interact with ALK4 in the absence of other factors.

Figure 3B:
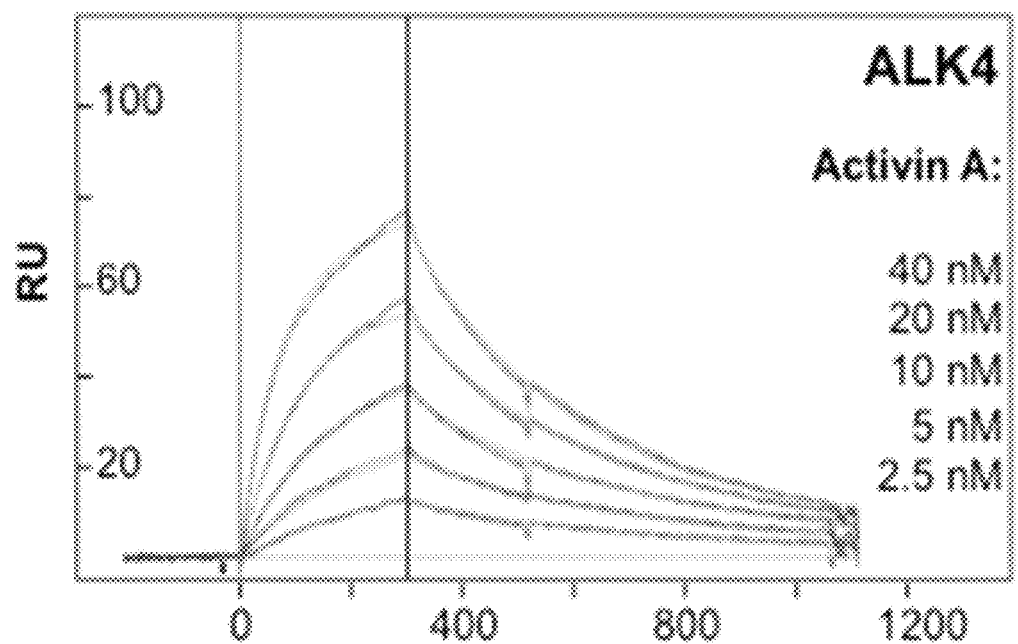
FIG. 3B depicts the binding of Activin A to ALK4. ALK4-Fc was captured on the sensor chip and different concentrations of Activin A as shown were injected. Curve fit of kinetic analysis is shown as orange lines.
Figure 3C:
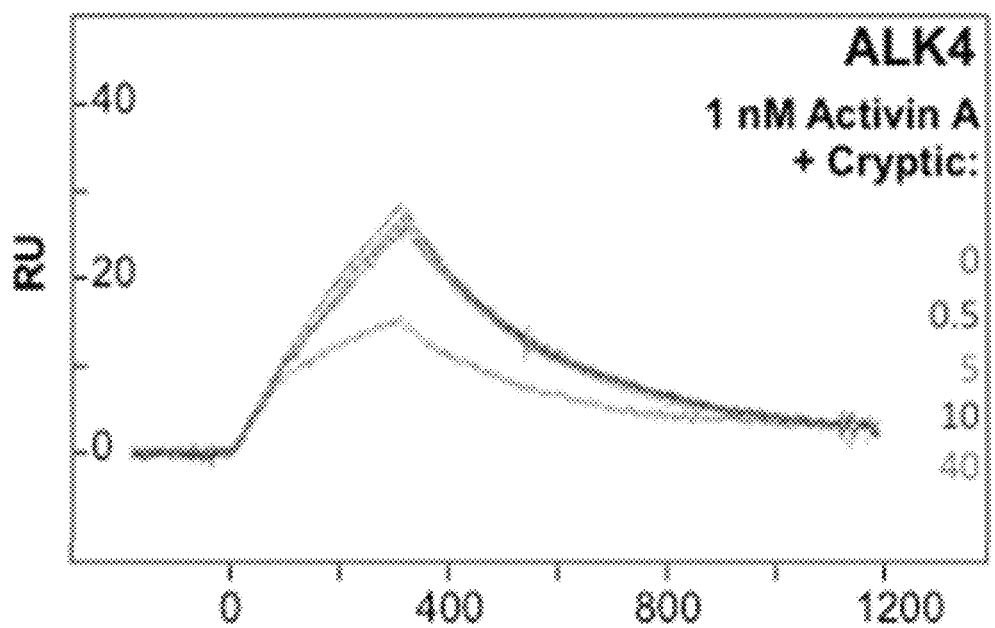
FIG. 3C depicts the binding of Activin A/Cryptic complexes to ALK4. ALK4-Fc was captured on the sensor chip and 10 nM Activin A preincubated with Fc free Cryptic (0-40 nM) were injected. The increase in response units when binding Cryptic is caused by a higher molecular weight of the Activin A-Cryptic complex. Saturation is dependent only on the concentration of Activin A.
Figure 3D:
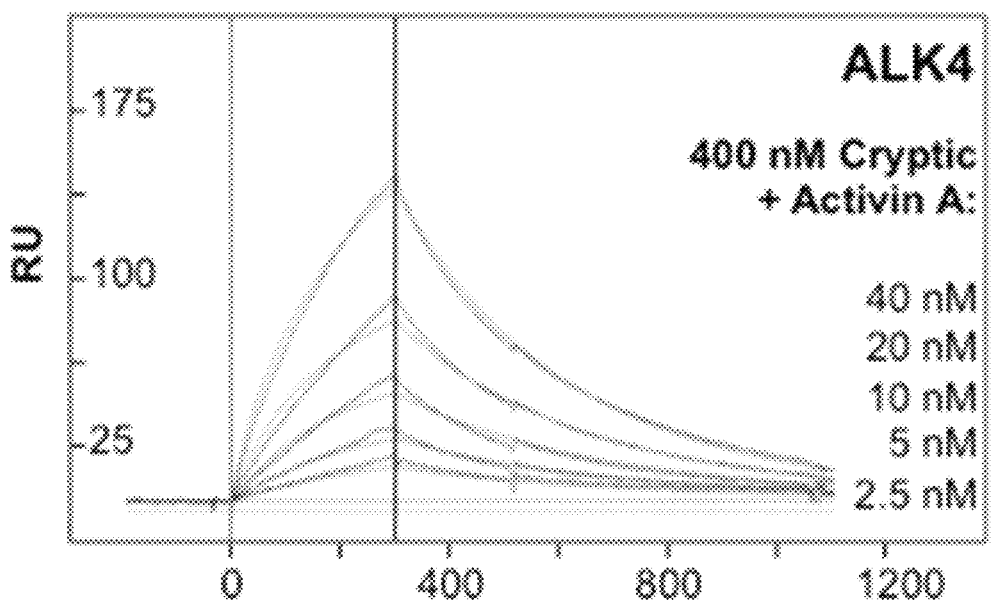
FIG. 3D depicts the binding of Activin A/Cryptic complexes to ALK4. ALK4-Fc was captured on the sensor chip and different concentrations of Activin A as shown preincubated with a constant amount of Fc free Cryptic (400 nM) were injected.

To determine whether Cryptic enhances or facilitates ligand binding to type I receptors, the effect of Cryptic on the interaction between Activin A and ALK4 was studied (FIG. 3B, FIG. 3C and FIG. 3D). Human ALK4-Fc was captured on a sensor chip and contacted with a constant amount of Activin A (1 nM) titrated with Cryptic (0-40 nM) (FIG. 3B) or titrated Activin A (0-40 nM) in the presence of excess Cryptic (400 nM) (FIG. 3D). Human Cryptic did not alter the interaction between Activin A and ALK4. Indeed, the kinetic model for free Activin A binding to ALK4 is virtually indistinguishable from that of Activin A binding to ALK4 in the presence of excess human Cryptic ($k_a=3.1\times10^5$ ($M^{-1}s^{-1}$), $k_d=4.6\times10^{-5}$ ($s^{-1}$), $K_d=0.15$ nM) (Table 1). Taken together, these findings demonstrate that Cryptic does not play a role in Activin A binding to ALK4.

TABLE 1

| Equilibrium binding and rate constants | | | | |
|---|---|---|---|---|
| Ligand | Analyte | $k_a$ ($M^{-1}s^{-1}$) | $k_d$ ($s^{-1}$) | $K_d$ (nM) |
| Cryptic-Fc | Activin A | $2.0 \times 10^4$ | $2.0 \times 10^{-3}$ | 0.001 |
| | Activin B | $9.5 \times 10^4$ | $4.7 \times 10^{-5}$ | 0.5 |
| | GDF-8 | $5.8 \times 10^4$ | $1.77 \times 10^{-4}$ | 3.0 |
| | GDF-11* | $2.9 \times 10^4$ | $1.1 \times 10^{-4}$ | 3.8 |
| BMPRII | Activin B | $5.1 \times 10^5$ | $4.2 \times 10^{-4}$ | 0.8 |
| ALK4 | Activin A | $4.5 \times 10^5$ | $1.8 \times 10^{-3}$ | 4.0 |
| | Activin A + Cryptic | $6.2 \times 10^5$ | $1.6 \times 10^{-3}$ | 2.6 |

*GDF-11 produced by refolding from *E. coli* (RnD Systems) shows batch variability.

Example 5. Cryptic Inhibits Ligand Binding to Type II Receptors

Next, the effect of Cryptic on ligand binding to the type II receptors was studied (FIG. 4). Ligands Activin A, Activin B, and GDF-8 were selected for these studies (FIG. 2). To determine whether Cryptic interacts with type II receptors, human ACTRIIA, ACTRIIB or BMPRII was captured on a sensor chip, followed by passing Cryptic over the captured receptors. In the absence of ligand, Cryptic did not bind ACTRIIA, ACTRIIB or BMPRII at concentrations that far exceeded physiological levels (e.g. 20 µM) (FIG. 3A).

Figure 4A:
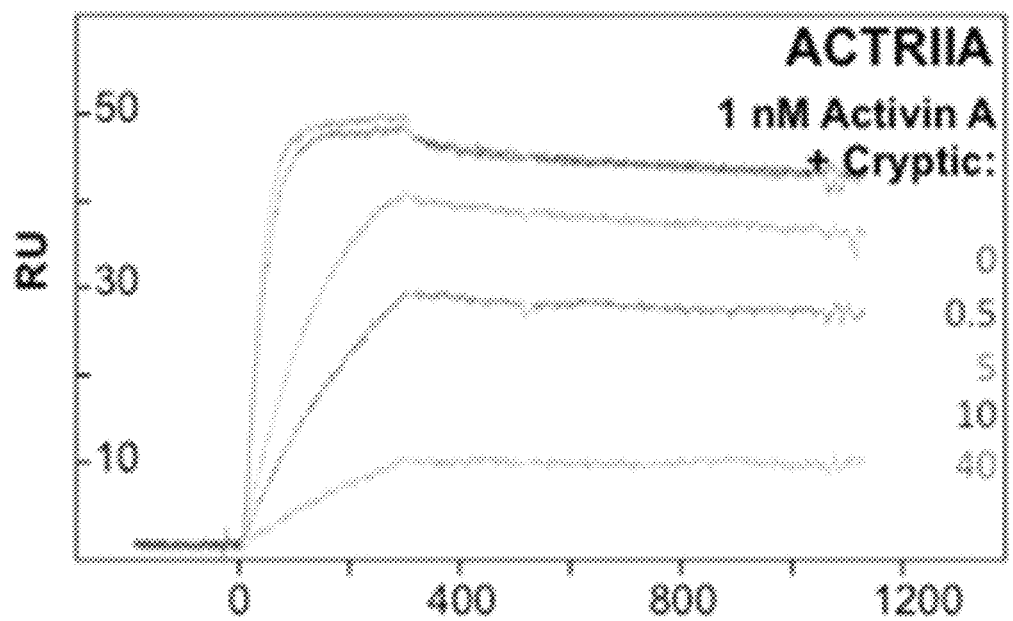
FIG. 4A depicts inhibition of Activin A binding to ACTRIIA by Cryptic.
Figure 4B:
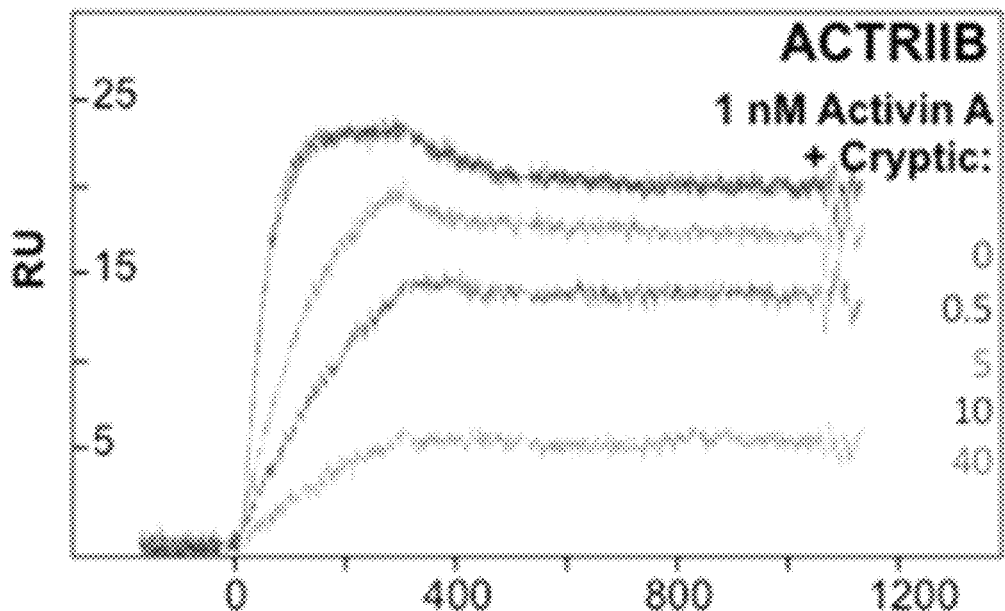
FIG. 4B depicts inhibition of Activin A binding to ACTRIIB by Cryptic.
Figure 4C:
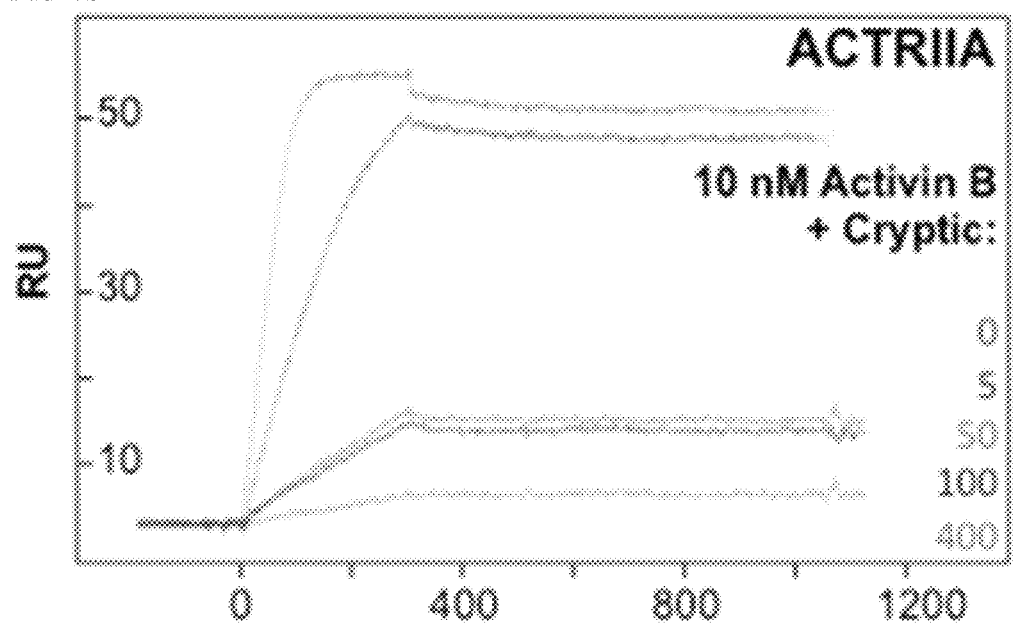
FIG. 4C depicts the inhibition of Activin B binding to ACTRIIA by Cryptic.
Figure 4D:
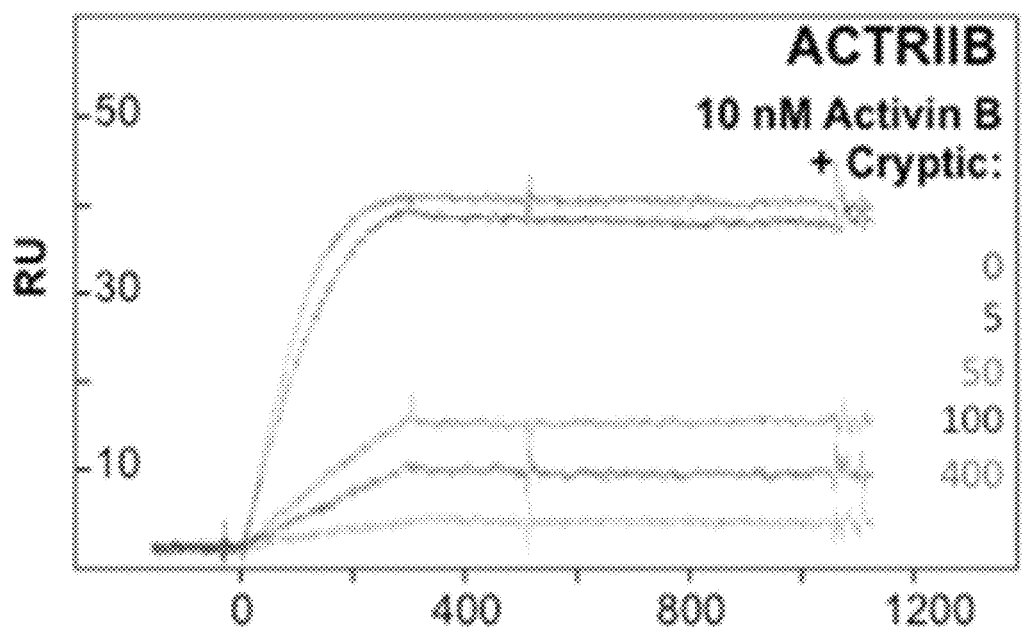
FIG. 4D depicts the inhibition of Activin B binding to ACTRIIB by Cryptic.
Figure 4E:
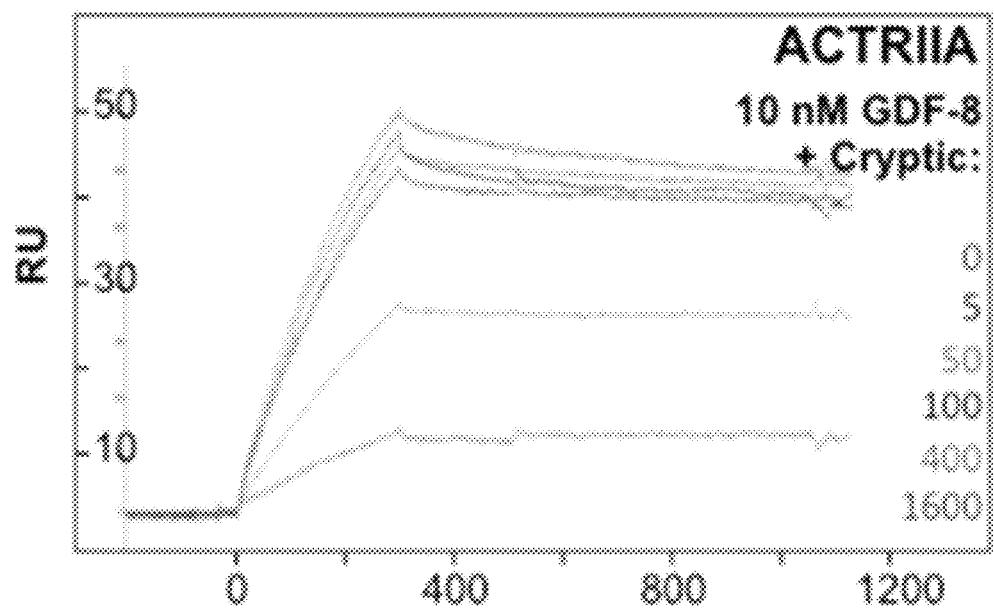
FIG. 4E depicts inhibition by Cryptic of GDF-8 binding to ACTRIIA.
Figure 4F:
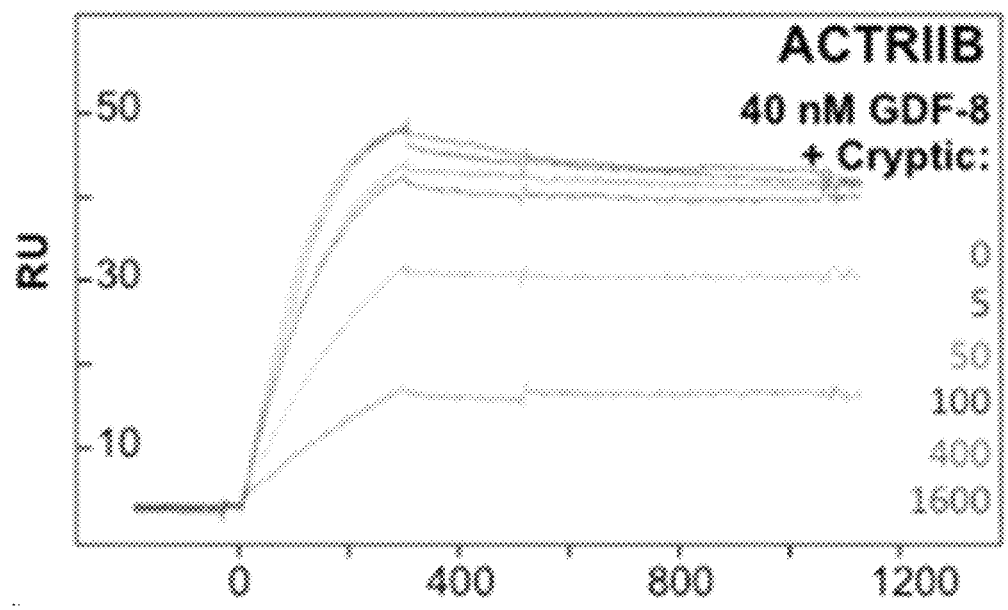
FIG. 4F depicts the inhibition of GDF-8 binding to ACTRIIB by Cryptic.
Figure 4G:
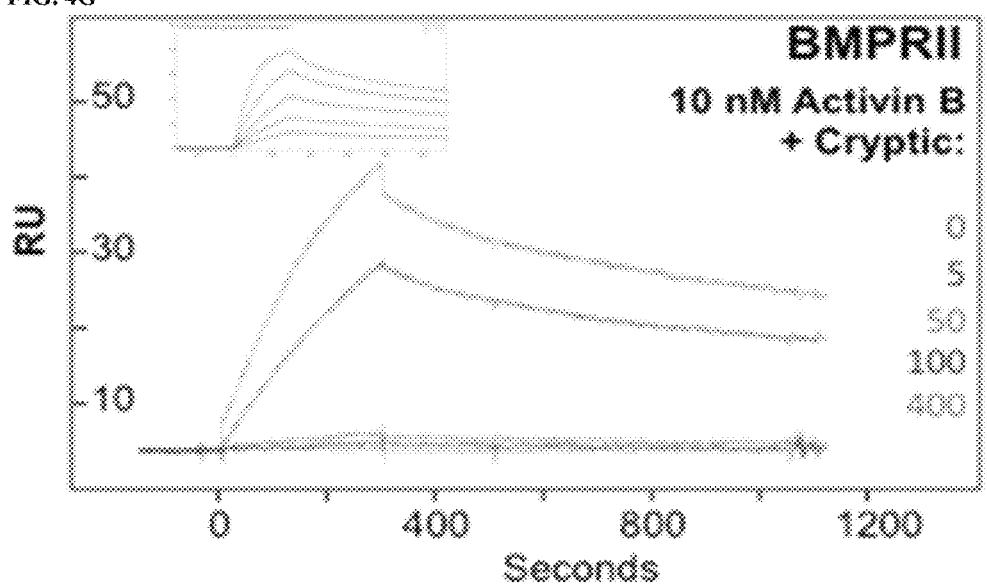
FIG. 4G depicts the inhibition by Cryptic of Activin B binding to BMPRII. BMPRII-Fc was captured on the sensor chip and 10 nM Activin B preincubated with 0 nM, 5 nM, 50 nM 100 nM or 400 nM Fc-free Cryptic was injected. The small insert shows the sensogram of Activin B binding to BMPRII with superimposed curve fit.
Figure 4H:
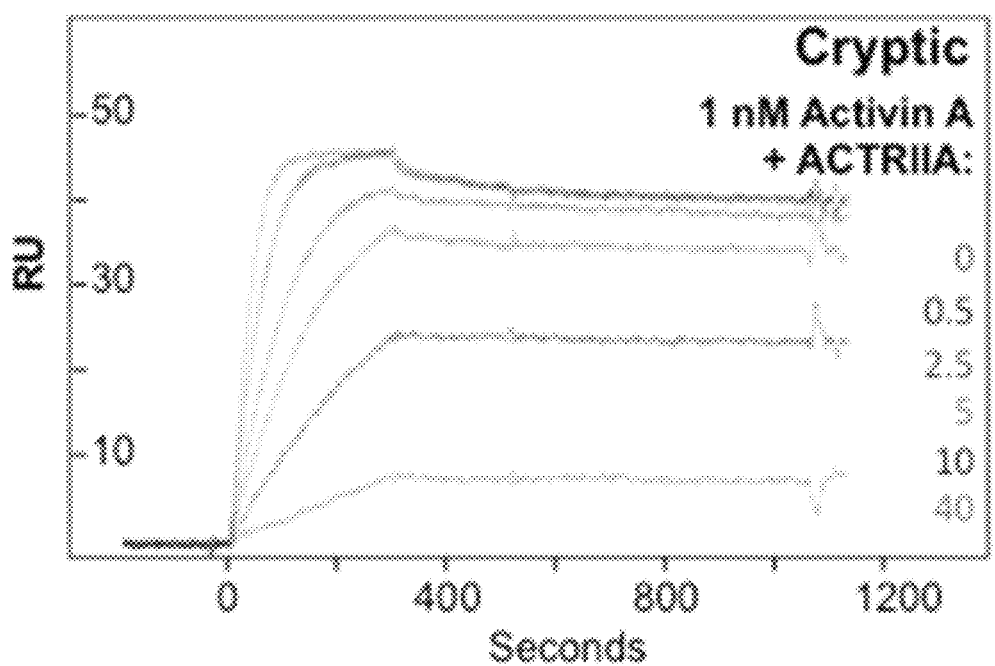
FIG. 4H depicts the inhibition by ACTRIIA of Activin A binding to Cryptic. Cryptic-Fc was captured on the sensor chip and 10 nM Activin A preincubated with 0 nM, 5 nM, 50 nM 100 nM or 400 nM Fc-free Cryptic was injected.

To determine whether Cryptic has an effect on ligand binding to ACTRIIA, ACTRIIB or BMPRII, these receptors were captured on a sensor chip, and Activin A (1 nM), Activin B (10 nM) or GDF-8 (40 nM), preincubated with Cryptic at concentrations between 0 and 1600 nM, were passed over the sensor chip. Cryptic inhibited ligand binding to high affinity receptors in a concentration-dependent manner. The inhibition was observed in the reversed geometry, i.e., with Cryptic-Fc captured on the sensor chip and Activin A, in the presence of varying amounts of ACTRIIA, passed over the sensor chip (FIG. 4H). Cryptic was further found to competitively inhibit the ligand-type II receptor interaction. These findings support the conclusion that human Cryptic binds Activin A, Activin B, and GDF-8 at same site that is bound by the type II receptors ACTRIIA, ACTRIIB and BMPRII.

Example 6. Cryptic Inhibits Activin Signaling

Figure 5A:
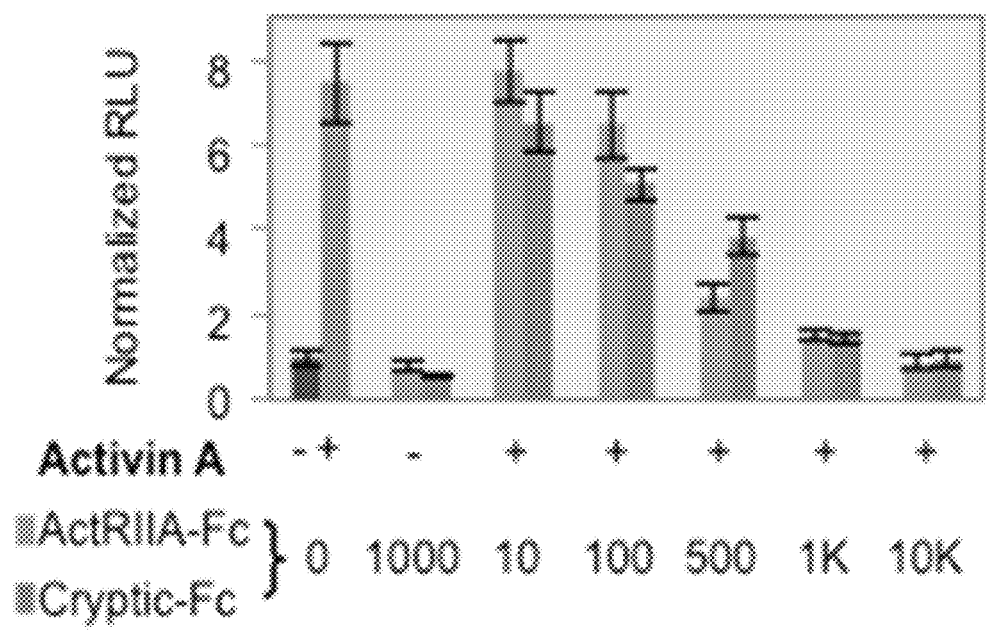
FIG. 5A depicts Cryptic-Fc's suppression of Activin A-mediated gene expression. 10 ng/ml Activin A induces expression of a Smad-2/3-responsive reporter. ACTRIIA-Fc and Cryptic-Fc equivalently inhibit the Activin A dependent luciferase signal in a concentration dependent manner (shown in ng/ml).
Figure 5B:
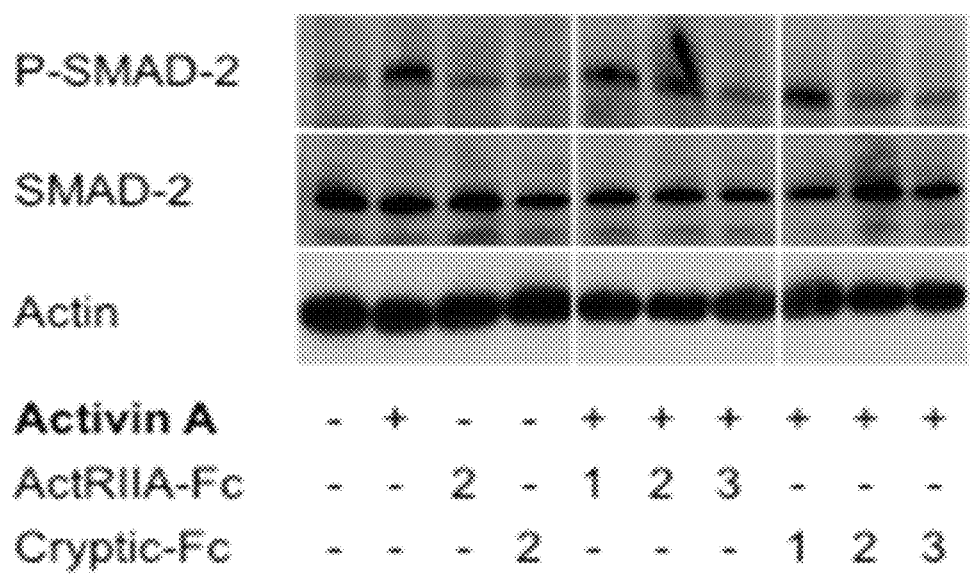
FIG. 5B is a Western blot depicting the detection of Smad2 phosphorylation. Activin A (10 ng/ml) induces Smad2 phosphorylation. ACTRIIA-Fc and Cryptic-Fc prevent Activin A mediated Smad-2 phosphorylation equivalently in a concentration dependent manner (1: 10, 2: 500, 3: 10,000 ng/ml).
Figure 5C:
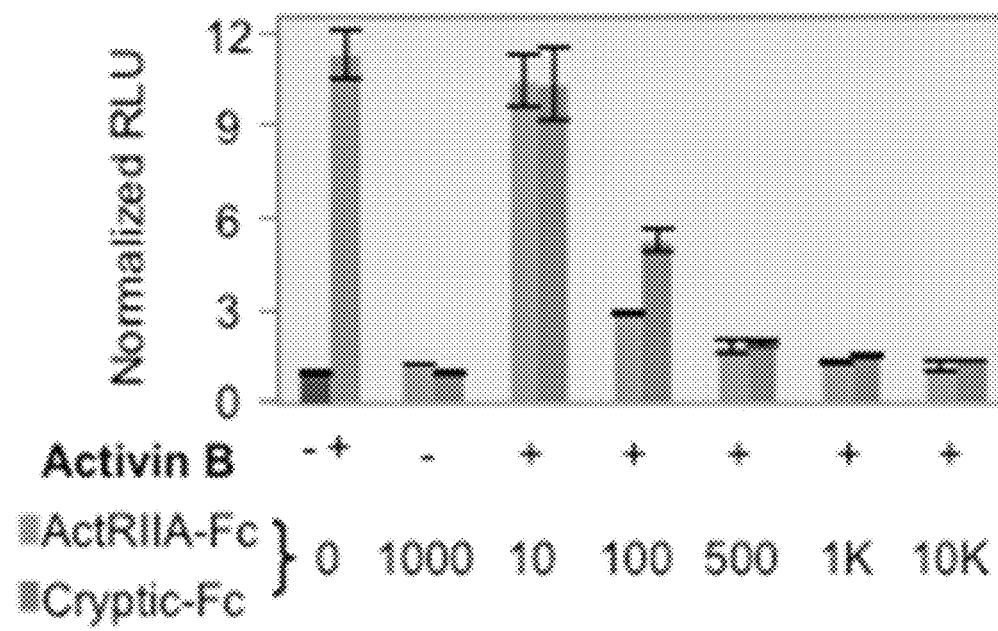
FIG. 5C depicts Cryptic-Fc suppression of Activin B-mediated gene expression. 10 ng/ml Activin A induces expression of a Smad-2/3-responsive reporter. ACTRIIA-Fc and Cryptic-Fc equivalently inhibit the Activin B dependent luciferase signal in a concentration dependent manner (shown in ng/ml).
Figure 5D:
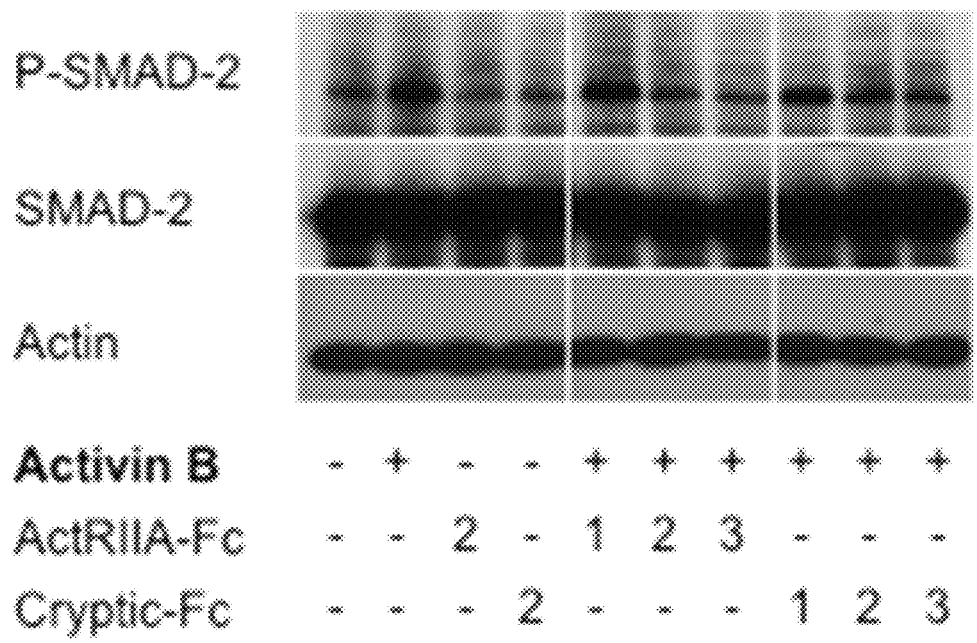
FIG. 5D is a Western blot depicting the detection of Smad2 phosphorylation. Activin B (10 ng/ml) induces Smad2 phosphorylation. ACTRIIA-Fc and Cryptic-Fc prevent Activin B mediated Smad-2 phosphorylation equivalently in a concentration dependent manner (1: 10, 2: 500, 3: 10,000 ng/ml).

As noted above, the data provided herein show that Cryptic competitively inhibits the ligand-type II receptor interaction. While the disclosure is not limited by any particular theory or mechanism of action, Cryptic might also inhibit ligand mediated signal transduction and gene expression. To examine the potential effect of Cryptic on ligand-dependent gene expression, A-204 rhabdomyosarcoma cells were transfected with pSBE4-luc, a Smad-2/3-responsive reporter, and pRL-CMV-luc as control (Zawal et al. (1998) *Mol Cell* 1:611-617). The transfected cells were treated with 10 nM Activin A or Activin B and different concentrations of Cryptic-Fc (FIG. 5A and FIG. 5C). Both ligands strongly induced Luciferase reporter activity (approximately 8 fold relative to control) and that Cryptic-Fc inhibited the ligand dependent luciferase signal in a concentration dependent manner (FIG. 5A and FIG. 5C). Indeed, Cryptic-Fc inhibited Activin A and Activin B induced Luciferase reporter activity with as well as the bone fide Activin inhibitor ACTRIIA-Fc (FIG. 5B and FIG. 5D). For signal transduction, a phospho-Smad2 Western blot was performed (FIG. 5B and FIG. 5D). A-204 cells were also treated with 10 nM ligand and titrated Cryptic-Fc. Activin A and Activin B induced and Cryptic-Fc inhibited Smad-2 phosphorylation. Indeed, Cryptic-Fc inhibited Smad-2 phosphorylation with similar potency as ACTRIIA-Fc (FIG. 5B and FIG. 5D).

Figure 5E:
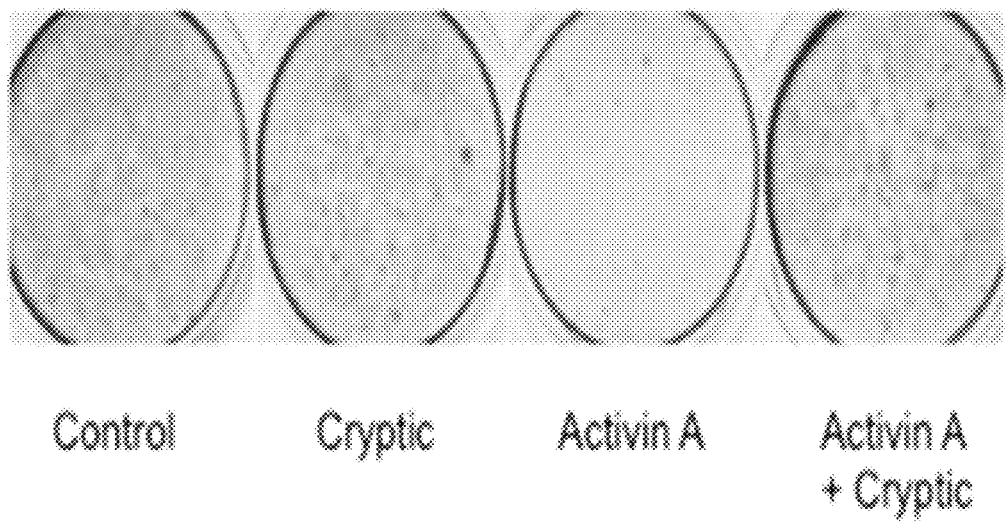
FIG. 5E depicts the effect of Cryptic on Activin A inhibition of osteoblast mineralization. HOS cells were cultured in the presence of osteogenic medium with and without Activin A and Cryptic-Fc. Mineralization was visualized by Alizarin Red S staining.
Figure 5F:
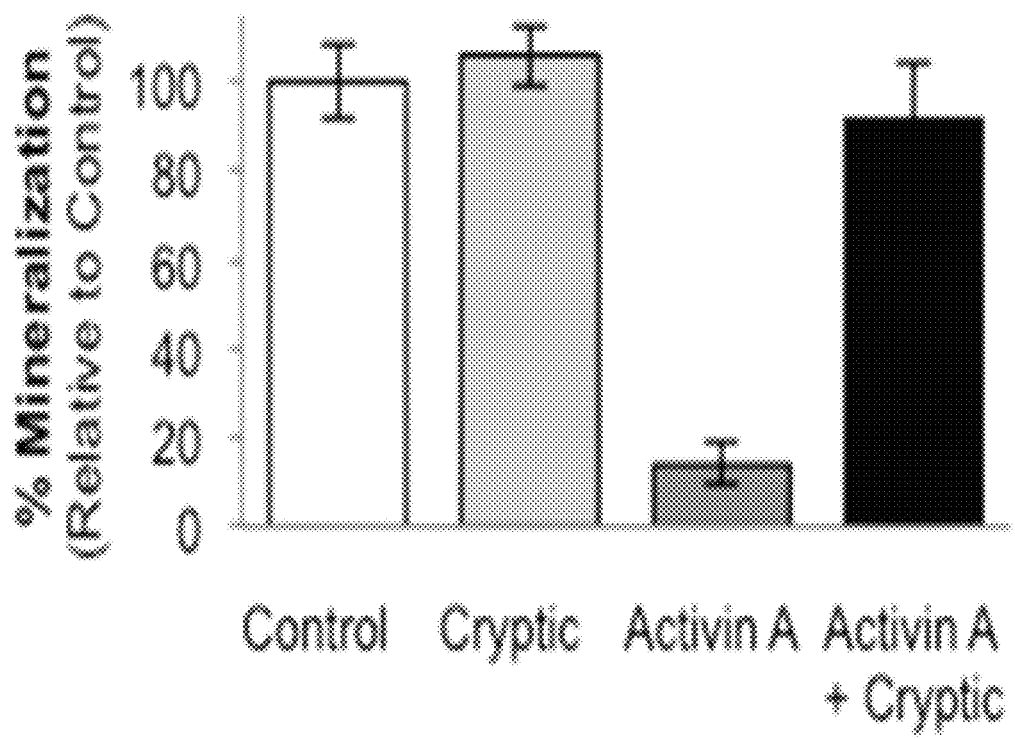
FIG. 5F depicts quantification of mineralization. Values are expressed as a % of mineralization in control wells.
Figure 6A:
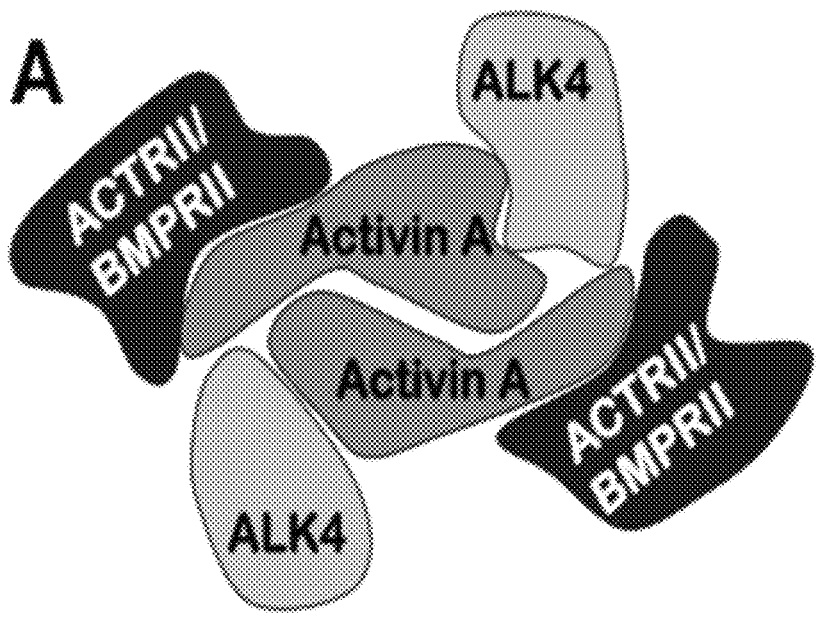
FIG. 6A is a model of ligand-receptor interactions based on the BMP-9-ALK1-ACTRIIB structure. The disulfide linked homodimeric ligand (center, orange) binds the extracellular domains of type I Activin receptor-like kinases (light blue) and type II Activin and BMP receptors (dark blue).
Figure 6B:
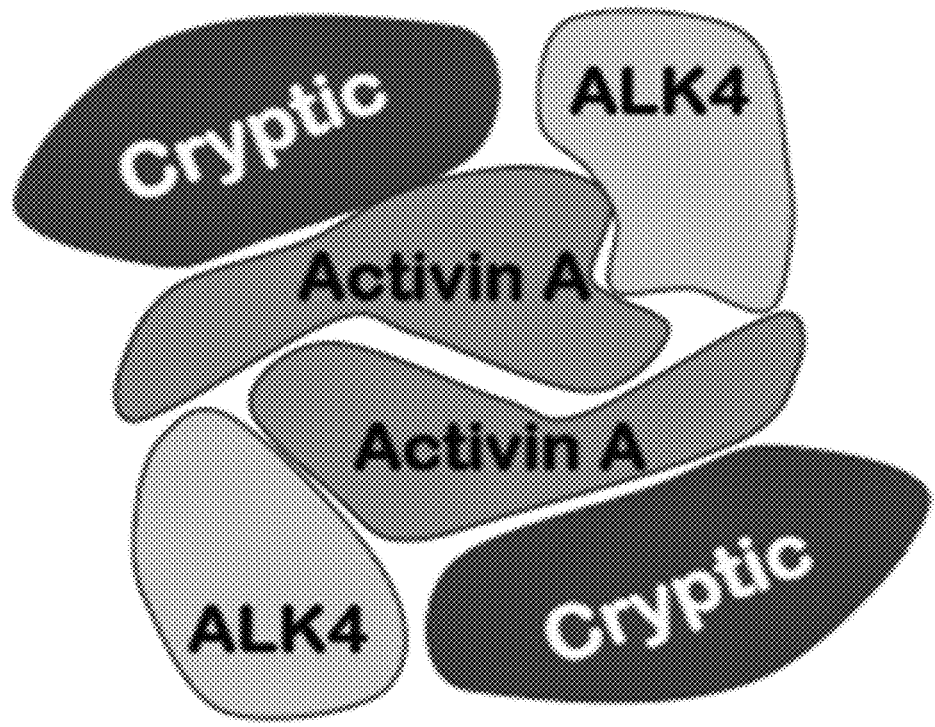
FIG. 6B is a model of Cripto-1/Cryptic ligand interactions. Cripto-1 and Cryptic are competitive inhibitors of the type II Activin and BMP receptor interaction, indicating that the binding site for Cripto-1 and Cryptic on the ligand is the same as that the binding site for ACTRIIA, ACTRIIB and BMPRII.
Figure 7A:
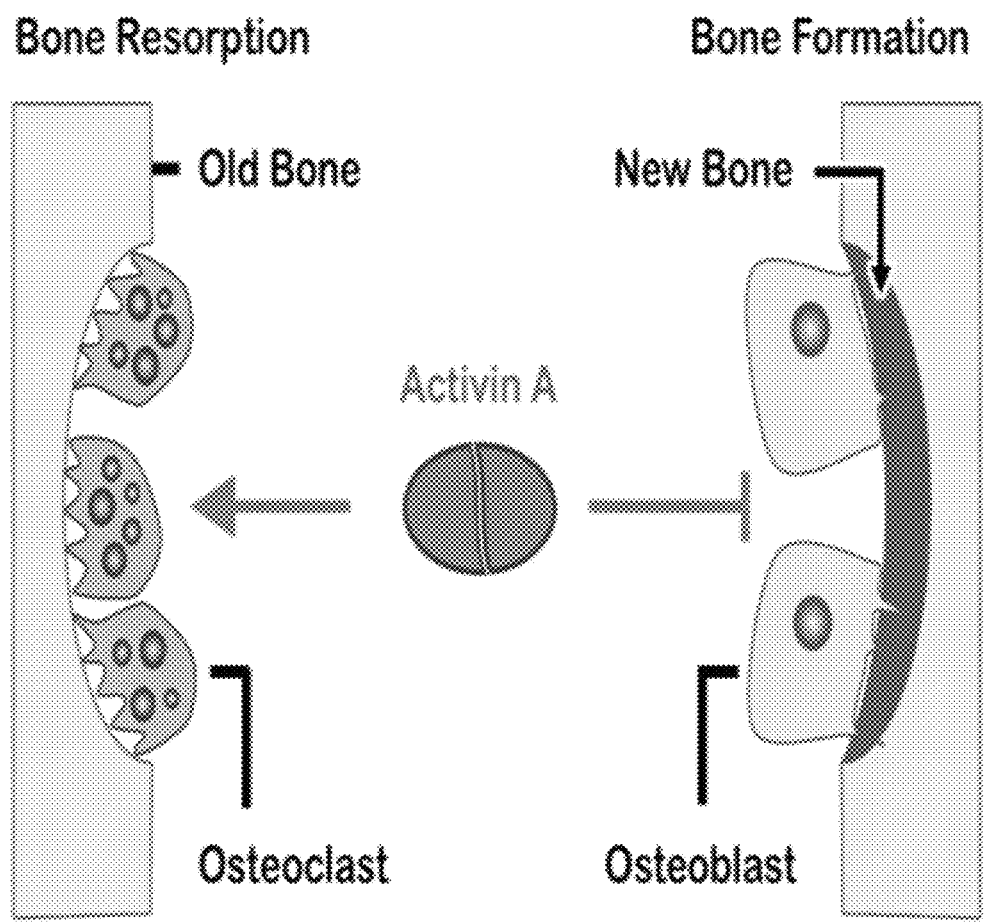
FIG. 7, contains two panels, FIG. 7A and FIG. 7B, and depicts a model of Cryptic-Fc (a Cryptic polypeptide fused to an Ig Fc region) inhibition of Activin A in bone remodeling (FIG. 7A).
FIG. 7B depicts that Activin A signals by binding type II Activin receptors (ActRIIA and ActRIIB). Cryptic-Fc prevents binding of Activin A to type II Activin receptors, and thus inhibits Activin A signaling, releasing the osteoinhibitory effect of Activin A and enabling osteoinduction by other TGFβ family signaling molecules.
Figure 7B:
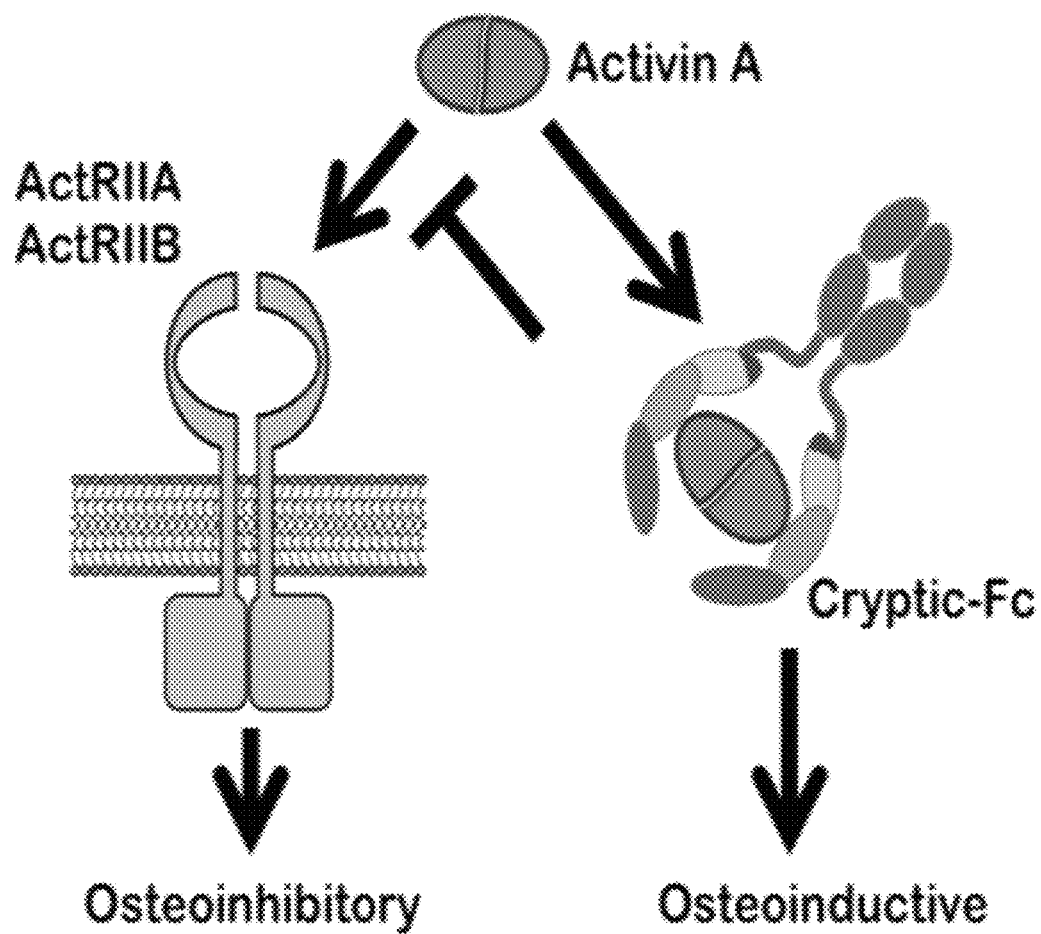
Figure 8A:
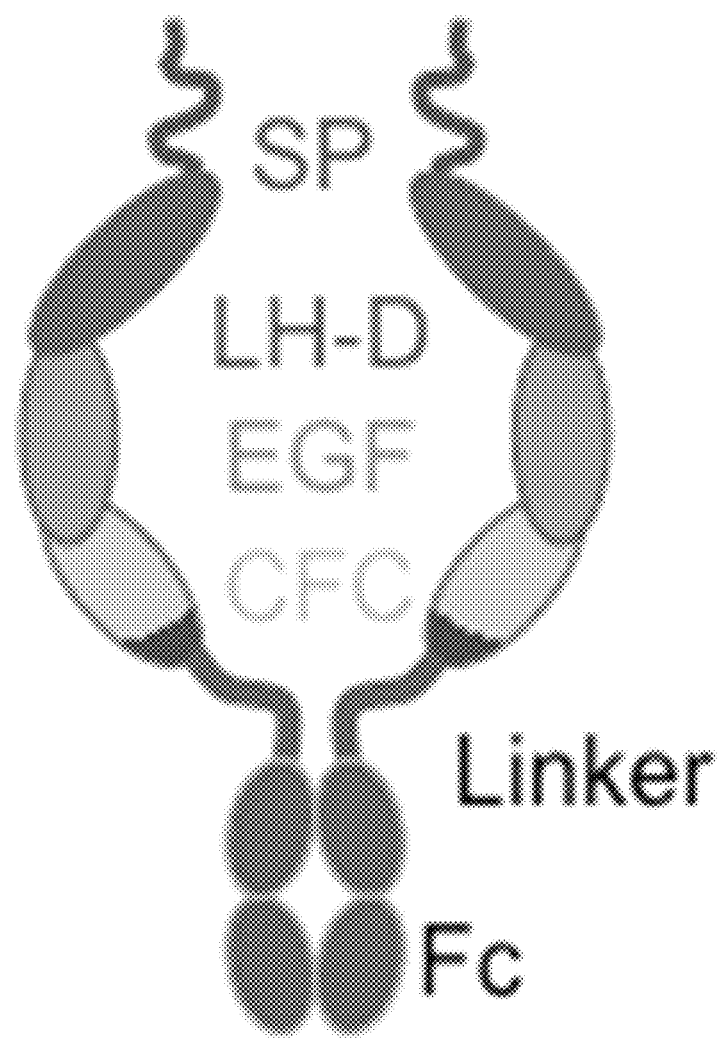
FIG. 8, contains five panels, FIG. 8A-FIG. 8E, and depicts a series of fusion protein constructs, each comprising all or a portion of Cryptic protein and highlighted the domain composition of Cryptic. Cryptic consists of a signal peptide for secretion (SP), a Low homology domain (LH-D), an EGF domain (EGF), a canonical CFC-domain (CFC) and a carboxy-terminal GPI signal. For Cryptic-Fc, the extracellular domain of Cryptic lacking the GPI signal peptide is fused to the Fc portion from human IgG1 via a 22 amino acid linker.
Figure 8B:
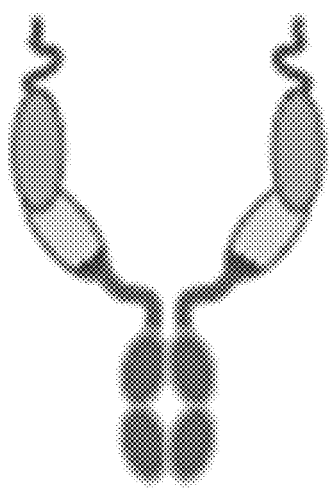
Figure 8C:
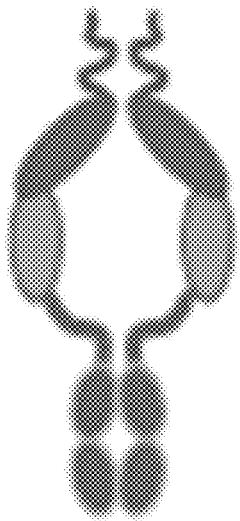
Figure 8D:
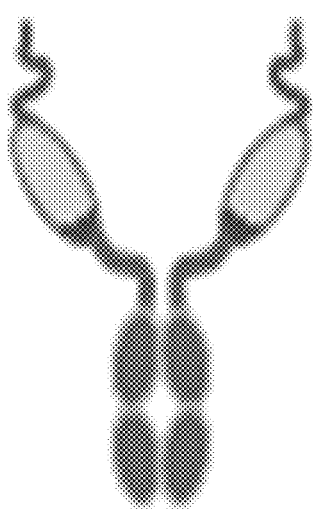
Figure 8E:
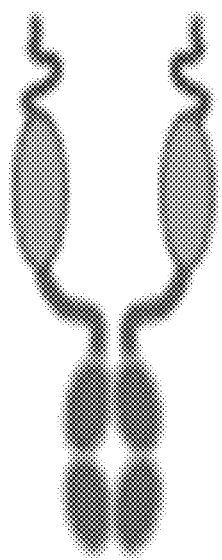

Given that Activin A inhibits and Activin A inhibitors promote osteoblast mineralization (see, e.g., Pear, Cryptic-Fc has an effect on osteoblast mineralization in the presence of Activin A. Human HOS cells were grown to confluence and induced to differentiate (by addition of phosphate and vitamin C) in the presence or absence of Activin A (50 ng/ml) with or without Cryptic. As expected, addition of Activin A prevents osteoblast mineralization (FIG. 5E and FIG. 5F). Strikingly, 10 µg/ml Cryptic-Fc prevented the Activin A suppression of mineralization (FIG. 5E and FIG. 5F). In summary, our results from three different in vitro experiments demonstrate that Cryptic-Fc efficiently inhibits Activin A mediated signaling with physiologically relevant outcomes, including the restoration of osteoblast mineralization (FIG. 5).

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A fusion polypeptide, comprising
an amino-terminal region wherein the amino-terminal region comprises an amino acid sequence that comprises SEQ ID NO: 19; and
a carboxy-terminal heterologous moiety, wherein the carboxy-terminal heterologous moiety provides for an increase in serum half-life of the fusion polypeptide compared to a peptide comprising the amino-terminal region without the carboxy-terminal heterologous moiety.

2. The fusion polypeptide of claim 1, wherein the carboxy-terminal heterologous moiety comprises all or a portion of an albumin protein, or all or a portion of an immunoglobulin constant region, or polyethylene glycol.

3. The fusion polypeptide of claim 2, wherein the immunoglobulin constant region is a carboxy-terminal immunoglobulin G Fc domain.

4. The fusion polypeptide of claim 3, wherein the carboxy-terminal immunoglobulin G Fc domain comprises an amino acid sequence that is SEQ ID NO: 17, SEQ ID NO: 21, or a functional fragment thereof.

5. The fusion polypeptide of claim 1, wherein the amino-terminal region and the carboxy-terminal heterologous moiety are separated by a linker region.

6. The fusion polypeptide of claim 5, wherein the linker region comprises 22 amino acids in length.

7. The fusion polypeptide of claim 5, wherein the linker region comprises an amino acid sequence that is SEQ ID NO: 18, or a functional fragment thereof.

8. The fusion polypeptide of claim 1, wherein the carboxy-terminal heterologous moiety is fused at or between amino acids in the fusion polypeptide corresponding to 165 to 175 of the amino-terminal region.

9. The fusion polypeptide of claim 1, wherein the fusion polypeptide lacks a glycosylphosphatidylinositol (GPI) domain.

10. The fusion polypeptide of claim 1, wherein the fusion polypeptide further comprises a functional signal domain for secretion.

11. The fusion polypeptide of claim 1, wherein the amino acid sequence of the amino-terminal region is SEQ ID NO: 19.

12. A fusion polypeptide, comprising:
an amino-terminal region, wherein the amino acid sequence of the amino-terminal region comprises SEQ ID NO: 20; and
a carboxy-terminal heterologous moiety, wherein the carboxy-terminal heterologous moiety provides for an increase in serum half-life of the fusion polypeptide compared to a peptide comprising the amino-terminal region without the carboxy-terminal heterologous moiety.

13. The fusion polypeptide of claim 12, wherein the amino acid sequence of the amino-terminal region is SEQ ID NO: 20.

14. A fusion polypeptide comprising an amino acid sequence that comprises SEQ ID NO: 22.

15. The fusion polypeptide of claim 14, wherein the fusion polypeptide comprises an amino acid sequence that is SEQ ID NO: 22.

16. A fusion polypeptide comprising an amino acid sequence that comprises SEQ ID NO: 10.

17. The fusion polypeptide of claim 16, wherein the fusion polypeptide comprises an amino acid sequence that is SEQ ID NO: 10.

18. The fusion polypeptide of claim 12, wherein the carboxy-terminal heterologous moiety comprises all or a portion of an albumin protein, or all or a portion of an immunoglobulin constant region, or polyethylene glycol.

19. The fusion polypeptide of claim 18, wherein the immunoglobulin constant region is a carboxy-terminal immunoglobulin G Fc domain.

20. The fusion polypeptide of claim 19, wherein the carboxy-terminal immunoglobulin G Fc domain comprises an amino acid sequence that is SEQ ID NO: 17, SEQ ID NO: 21, or a functional fragment thereof.

21. The fusion polypeptide of claim 12, wherein the amino-terminal region and the carboxy-terminal heterologous moiety are separated by a linker region.

22. The fusion polypeptide of claim 21, wherein the linker region comprises an amino acid sequence that is SEQ ID NO: 18, or a functional fragment thereof.

* * * * *